(12) United States Patent
Cameron et al.

(10) Patent No.: US 11,952,576 B1
(45) Date of Patent: Apr. 9, 2024

(54) METHODS FOR MEASURING AND OPTIMIZING THE STRUCTURE, LOCATION, AND ACTIVITY OF NATURAL AND ENGINEERED MICROCOMPARMENTS, ORGANELLES, AND MACROMOLECULES

(71) Applicant: The Regents of the University of Colorado, a body, Denver, CO (US)

(72) Inventors: Jeffrey Carlyle Cameron, Erie, CO (US); Nicholas C. Hill, Boulder, CO (US); Jian Wei Tay, Boulder, CO (US); Sabina Altus, Denver, CO (US); David Matthew Bortz, Boulder, CO (US); Kristin Ann Moore, Broomfield, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 442 days.

(21) Appl. No.: 17/099,205

(22) Filed: Nov. 16, 2020

Related U.S. Application Data

(60) Provisional application No. 62/935,738, filed on Nov. 15, 2019.

(51) Int. Cl.
*C12N 15/72* (2006.01)
*C12N 1/20* (2006.01)
*C12N 15/10* (2006.01)

(52) U.S. Cl.
CPC ............... *C12N 15/72* (2013.01); *C12N 1/20* (2013.01); *C12N 15/102* (2013.01); *C12Y 401/01039* (2013.01)

(58) Field of Classification Search
None
See application file for complete search history.

(56) References Cited

PUBLICATIONS

Arjes HA, Kriel A, Sorto NA, Shaw JT, Wang JD, Levin PA. Failsafe mechanisms couple division and DNA replication in bacteria. Curr Biol. Sep. 22, 2014;24(18):2149-2155. doi: 10.1016/j.cub.2014.07.055. Epub Aug. 28, 2014. PMID: 25176632; PMCID: PMC4175050.
Bernard R, Marquis KA, Rudner DZ. Nucleoid occlusion prevents cell division during replication fork arrest in Bacillus subtilis. Mol Microbiol. Nov. 2010;78(4):866-82. doi: 10.1111/j.1365-2958.2010.07369.x. Epub Sep. 23, 2010. PMID: 20807205; PMCID: PMC2978284.
Blin K, Pedersen LE, Weber T, Lee SY. CRISPy-web: An online resource to design sgRNAs for CRISPR applications. Synth Syst Biotechnol. Feb. 12, 2016;1(2):118-121. doi: 10.1016/j.synbio.2016.01.003. PMID: 29062934; PMCID: PMC5640694.
Blinkova A, Hervas C, Stukenberg PT, Onrust R, O'Donnell ME, Walker JR. The *Escherichia coli* DNA polymerase III holoenzyme contains both products of the dnaX gene, tau and gamma, but only tau is essential. J Bacteriol. Sep. 1993;175(18):6018-27. doi: 10.1128/jb.175.18.6018-6027.1993. PMID: 8376347; PMCID: PMC206684.
Bryant JA, Sellars LE, Busby SJ, Lee DJ. Chromosome position effects on gene expression in *Escherichia coli* K-12. Nucleic Acids Res. Oct. 2014;42(18):11383-92. doi: 10.1093/nar/gku828. Epub Sep. 10, 2014. PMID: 25209233; PMCID: PMC4191405.
Chen AH, Afonso B, Silver PA, Savage DF. Spatial and temporal organization of chromosome duplication and segregation in the cyanobacterium *Synechococcus elongatus* PCC 7942. PLoS One. 2012;7(10):e47837. doi: 10.1371/journal.pone.0047837. Epub Oct. 24, 2012. PMID: 23112856; PMCID: PMC3480399.
Clark RL, McGinley LL, Purdy HM, Korosh TC, Reed JL, Root TW, Pfleger BF. Light-optimized growth of cyanobacterial cultures: Growth phases and productivity of biomass and secreted molecules in light-limited batch growth. Metab Eng. May 2018;47:230-242. doi: 10.1016/j.ymben.2018.03.017. Epub Mar. 27, 2018. PMID: 29601856; PMCID: PMC5984190.
Clay Montier LL, Deng JJ, Bai Y. Number matters: control of mammalian mitochondrial DNA copy number. J Genet Genomics. Mar. 2009;36(3):125-31. doi: 10.1016/S1673-8527(08)60099-5. PMID: 19302968; PMCID: PMC4706993.
Davies FK, Work VH, Beliaev AS, Posewitz MC. Engineering Limonene and Bisabolene Production in Wild Type and a Glycogen-Deficient Mutant of *Synechococcus* sp. PCC 7002. Front Bioeng Biotechnol. Jun. 19, 2014;2:21. doi: 10.3389/fbioe.2014.00021. PMID: 25152894; PMCID: PMC4126464.
Donachie WD, Begg KJ. Cell length, nucleoid separation, and cell division of rod-shaped and spherical cells of *Escherichia coli*. J Bacteriol. Sep. 1989;171(9):4633-9. doi: 10.1128/jb.171.9.4633-4639.1989. PMID: 2670889; PMCID: PMC210261.
Gehring AM, Astling DP, Matsumi R, Burkhart BW, Kelman Z, Reeve JN, Jones KL, Santangelo TJ. Genome Replication in *Thermococcus kodakarensis* Independent of Cdc6 and an Origin of Replication. Front Microbiol. Oct. 27, 2017;8:2084. doi: 10.3389/fmicb.2017.02084. PMID: 29163389; PMCID: PMC5663688.
Jain IH, Vijayan V, O'Shea EK. Spatial ordering of chromosomes enhances the fidelity of chromosome partitioning in cyanobacteria. Proc Natl Acad Sci U S A. Aug. 21, 2012;109(34):13638-43. doi: 10.1073/pnas.1211144109. Epub Aug. 6, 2012. PMID: 22869746; PMCID: PMC3427121.

(Continued)

*Primary Examiner* — Brian Gangle
(74) *Attorney, Agent, or Firm* — Michael M. McGaw; McGaw Law, P.C.

(57) ABSTRACT

A novel method of diluting the structures in the cell population, such that individual cells, dependent on the activity of the structures, become single measurement devices. This can be applied to all Bacterial Microcomparments ("BMCs"), organelles, and macromolecules, and could provide a universal method for the design of novel ones and understanding of the diverse structures. In one aspect the present invention provides A method of creating a bacterial strain with inducible and detectable carboxysomes. The method includes the steps of incorporating a labeled carbon-fixation enzyme into the genome of a bacterium; deleting all or a portion of the ccm operon from the bacterium; and reintroducing a ccm operon comprising an inducible promoter to create a Δccm+ strain.

14 Claims, 35 Drawing Sheets

Specification includes a Sequence Listing.

(56) References Cited

PUBLICATIONS

Klumpp S, Zhang Z, Hwa T. Growth rate-dependent global effects on gene expression in bacteria. Cell. Dec. 24, 2009;139(7):1366-75. doi: 10.1016/j.cell.2009.12.001. PMID: 20064380; PMCID: PMC2818994.

Lin, J., & Amir, A. (2018). Homeostasis of protein and mRNA concentrations in growing cells. Nature Communications, 9(1), 4496.

Locey KJ, Lennon JT. Scaling laws predict global microbial diversity. Proc Natl Acad Sci U S A. May 24, 2016;113(21):5970-5. doi: 10.1073/pnas.1521291113. Epub May 2, 2016. PMID: 27140646; PMCID: PMC4889364.

Kate Maxwell, Giles N. Johnson, Chlorophyll fluorescence—a practical guide, Journal of Experimental Botany, vol. 51, Issue 345, Apr. 2000, pp. 659-668, https://doi.org/10.1093/jxb/51.345.659.

Michaelis, C., Ciosk, R., & Nasmyth, K. (1997). Cohesins: chromosomal proteins that prevent premature separation of sister chromatids. Cell, 91(1), 35-45. https://doi.org/10.1016/s0092-8674(01)80007-6.

O'Donnell, M., Langston, L., & Stillman, B. (2013). Principles and concepts of DNA replication in bacteria, archaea, and eukarya. Cold Spring Harbor perspectives in biology, 5(7), a010108. https://doi.org/10.1101/cshperspect.a010108.

Ohbayashi, R., Hirooka, S., Onuma, R., Kanesaki, Y., Hirose, Y., Kobayashi, Y., Fujiwara, T., Furusawa, C., & Miyagishima, S. Y. (2020). Evolutionary Changes in DnaA-Dependent Chromosomal Replication in Cyanobacteria. Frontiers in microbiology, 11, 786. https://doi.org/10.3389/fmicb.2020.00786.

Ohbayashi, R., Nakamachi, A., Hatakeyama, T. S., Watanabe, S., Kanesaki, Y., Chibazakura, T., Yoshikawa, H., & Miyagishima, S. Y. (2019). Coordination of Polyploid Chromosome Replication with Cell Size and Growth in a Cyanobacterium. mBio, 10(2), e00510-19. https://doi.org/10.1128/mBio.00510-19.

Ohbayashi, R., Watanabe, S., Ehira, S., Kanesaki, Y., Chibazakura, T., & Yoshikawa, H. (2016). Diversification of DnaA dependency for DNA replication in cyanobacterial evolution. The ISME journal, 10(5), 1113-1121. https://doi.org/10.1038/ismej.2015.194.

Pecoraro, V., Zerulla, K., Lange, C., & Soppa, J. (2011). Quantification of ploidy in proteobacteria revealed the existence of monoploid, (mero-)oligoploid and polyploid species. PloS one, 6(1), e16392. https://doi.org/10.1371/journal.pone.0016392.

Richter, S., Hagemann, M., & Messer, W. (1998). Transcriptional analysis and mutation of a dnaA-like gene in Synechocystis sp. strain PCC 6803. Journal of bacteriology, 180(18), 4946-4949. https://doi.org/10.1128/JB.180.18.4946-4949.1998.

Sakamoto, W., & Takami, T. (2018). Chloroplast DNA Dynamics: Copy Number, Quality Control and Degradation. Plant and Cell Physiology, 59(6), 1120-1127.

Selmecki, A. M., Maruvka, Y. E., Richmond, P. A., Guillet, M., Shoresh, N., Sorenson, A. L., De, S., Kishony, R., Michor, F., Dowell, R., & Pellman, D. (2015). Polyploidy can drive rapid adaptation in yeast. Nature, 519(7543), 349-352. https://doi.org/10.1038/nature14187.

Zerulla, K., Chimileski, S., Näther, D., Gophna, U., Papke, R. T., & Soppa, J. (2014). DNA as a phosphate storage polymer and the alternative advantages of polyploidy for growth or survival. PloS one, 9(4), e94819. https://doi.org/10.1371/journal.pone.0094819.

Zheng, X. Y., & O'Shea, E. K. (2017). Cyanobacteria Maintain Constant Protein Concentration despite Genome Copy-Number Variation. Cell reports, 19(3), 497-504. https://doi.org/10.1016/j.celrep.2017.03.067.

Axen SD, Erbilgin O, Kerfeld CA. A taxonomy of bacterial microcompartment loci constructed by a novel scoring method. PLoS Comput Biol. Oct. 23, 2014;10(10):e1003898. doi: 10.1371/journal.pcbi.1003898. PMID: 25340524; PMCID: PMC4207490.

Rae BD, Long BM, Badger MR, Price GD. Functions, compositions, and evolution of the two types of carboxysomes: polyhedral microcompartments that facilitate CO2 fixation in cyanobacteria and some proteobacteria. Microbiol Mol Biol Rev. Sep. 2013;77(3):357-79. doi: 10.1128/MMBR.00061-12. PMID: 24006469; PMCID: PMC3811607.

A. Turmo, C. R. Gonzalez-Esquer, C. A. Kerfeld, Carboxysomes: metabolic modules for CO2 fixation. FEMS Microbiol. Lett. 364 (2017), doi:10.1093/femsle/fnx176.

Price GD, Badger MR, Woodger FJ, Long BM. Advances in understanding the cyanobacterial CO2-concentrating-mechanism (CCM): functional components, Ci transporters, diversity, genetic regulation and prospects for engineering into plants. J Exp Bot. 2008;59(7):1441-61. doi: 10.1093/jxb/erm112. Epub Jun. 19, 2007. PMID: 17578868.

Gonzalez-Esquer CR, Newnham SE, Kerfeld CA. Bacterial microcompartments as metabolic modules for plant synthetic biology. Plant J. Jul. 2016;87(1):66-75. doi: 10.1111/tpj.13166. Epub Jun. 20, 2016. PMID: 26991644.

Long BM, Hee WY, Sharwood RE, Rae BD, Kaines S, Lim YL, Nguyen ND, Massey B, Bala S, von Caemmerer S, Badger MR, Price GD. Carboxysome encapsulation of the CO2-fixing enzyme Rubisco in tobacco chloroplasts. Nat Commun. Sep. 3, 2018;9(1):3570. doi: 10.1038/s41467-018-06044-0. PMID: 30177711; PMCID: PMC6120970.

Cameron JC, Wilson SC, Bernstein SL, Kerfeld CA. Biogenesis of a bacterial organelle: the carboxysome assembly pathway. Cell. Nov. 21, 2013;155(5):1131-40. doi: 10.1016/j.cell.2013.10.044. PMID: 24267892.

Bernstein HC, McClure RS, Hill EA, Markillie LM, Chrisler WB, Romine MF, McDermott JE, Posewitz MC, Bryant DA, Konopka AE, Fredrickson JK, Beliaev AS. Unlocking the Constraints of Cyanobacterial Productivity: Acclimations Enabling Ultrafast Growth. mBio. Jul. 26, 2016;7(4):e00949-16. doi: 10.1128/mBio.00949-16. PMID: 27460798; PMCID: PMC4981716.

Ruffing AM, Jensen TJ, Strickland LM. Genetic tools for advancement of Synechococcus sp. PCC 7002 as a cyanobacterial chassis. Microb Cell Fact. Nov. 10, 2016;15(1):190. doi: 10.1186/s12934-016-0584-6. PMID: 27832791; PMCID: PMC5105302.

Gordon GC, Korosh TC, Cameron JC, Markley AL, Begemann MB, Pfleger BF. CRISPR interference as a titratable, trans-acting regulatory tool for metabolic engineering in the cyanobacterium Synechococcus sp. strain PCC 7002. Metab Eng. Nov. 2016;38:170-179. doi: 10.1016/j.ymben.2016.07.007. Epub Jul. 29, 2016. PMID: 27481676; PMCID: PMC5107151.

Markley AL, Begemann MB, Clarke RE, Gordon GC, Pfleger BF. Synthetic biology toolbox for controlling gene expression in the cyanobacterium Synechococcus sp. strain PCC 7002. ACS Synth Biol. May 15, 2015;4(5):595-603. doi: 10.1021/sb500260k. Epub Sep. 25, 2014. PMID: 25216157; PMCID: PMC4431953.

MacCready JS, Hakim P, Young EJ, Hu L, Liu J, Osteryoung KW, Vecchiarelli AG, Ducat DC. Protein gradients on the nucleoid position the carbon-fixing organelles of cyanobacteria. Elife. Dec. 6, 2018;7:e39723. doi: 10.7554/eLife.39723. PMID: 30520729; PMCID: PMC6328274.

Jakobson CM, Tullman-Ercek D. Dumpster Diving in the Gut: Bacterial Microcompartments as Part of a Host-Associated Lifestyle. PLoS Pathog. May 12, 2016;12(5):e1005558. doi: 10.1371/journal.ppat.1005558. PMID: 27171216; PMCID: PMC4865037.

Campos M, Surovtsev IV, Kato S, Paintdakhi A, Beltran B, Ebmeier SE, Jacobs-Wagner C. A constant size extension drives bacterial cell size homeostasis. Cell. Dec. 4, 2014;159(6):1433-46. doi: 10.1016/j.cell.2014.11.022. PMID: 25480302; PMCID: PMC4258233.

Chowdhury C, Sinha S, Chun S, Yeates TO, Bobik TA. Diverse bacterial microcompartment organelles. Microbiol Mol Biol Rev. Sep. 2014;78(3):438-68. doi: 10.1128/MMBR.00009-14. PMID: 25184561; PMCID: PMC4187681.

Jaqaman K, Loerke D, Mettlen M, Kuwata H, Grinstein S, Schmid SL, Danuser G. Robust single-particle tracking in live-cell time-lapse sequences. Nat Methods. Aug. 2008;5(8):695-702. doi: 10.1038/nmeth.1237. Epub Jul. 20, 2008. PMID: 18641657; PMCID: PMC2747604.

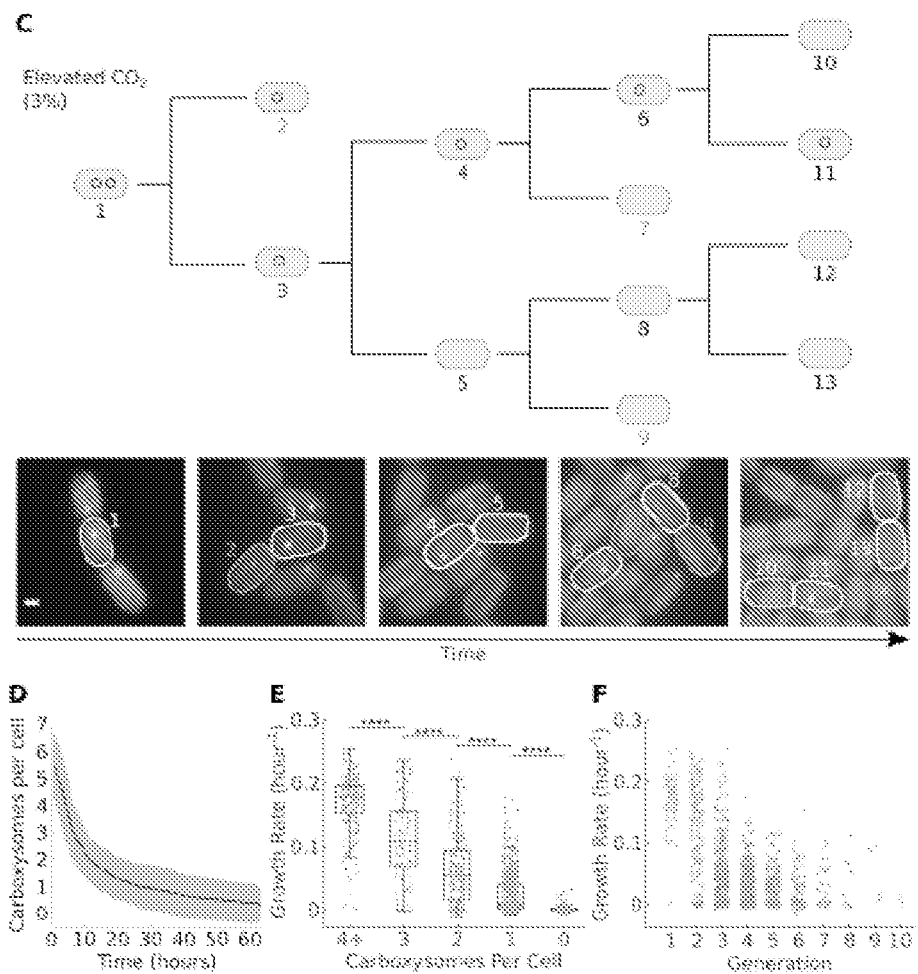
FIG. 1 - continued

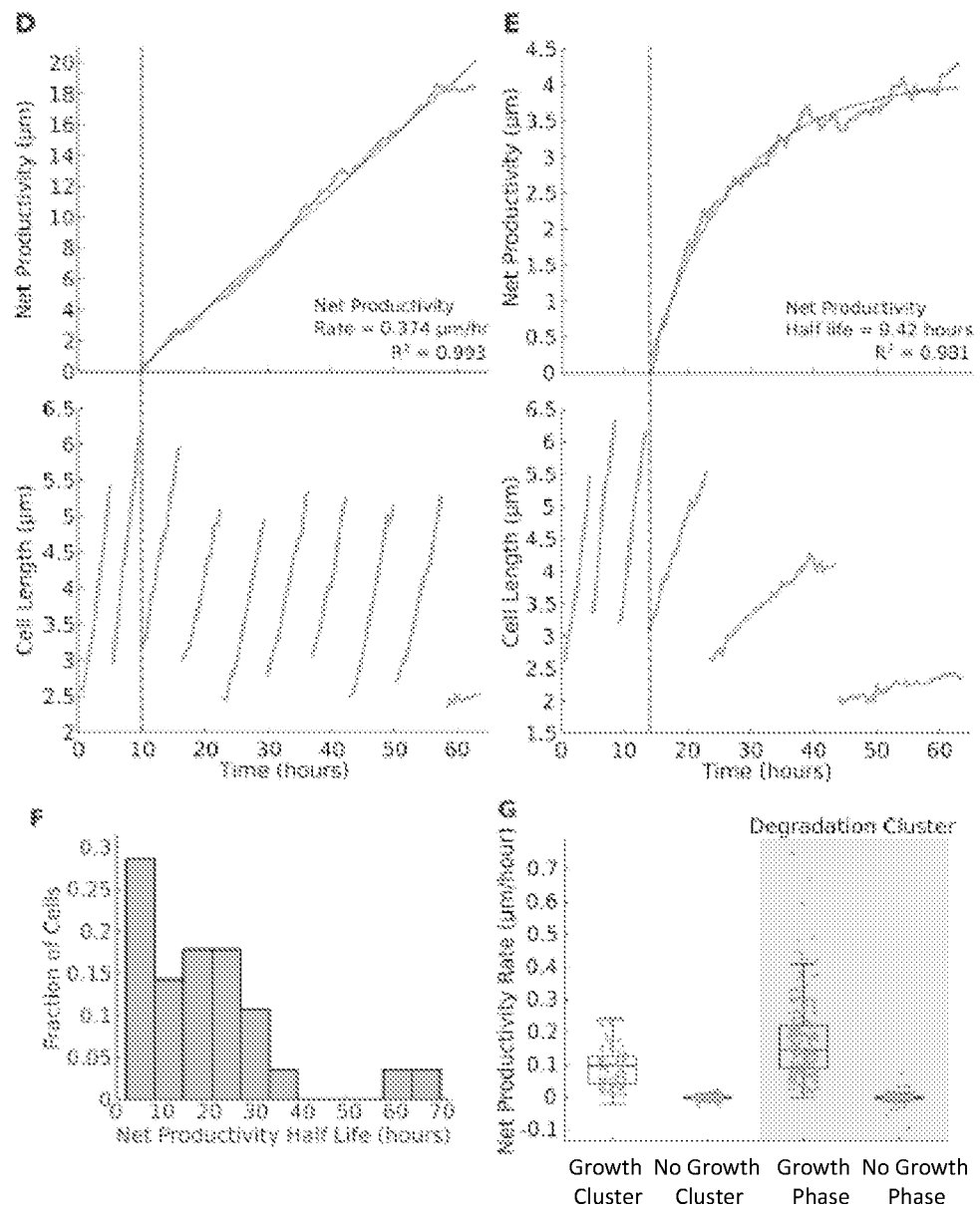
FIG. 2 - continued

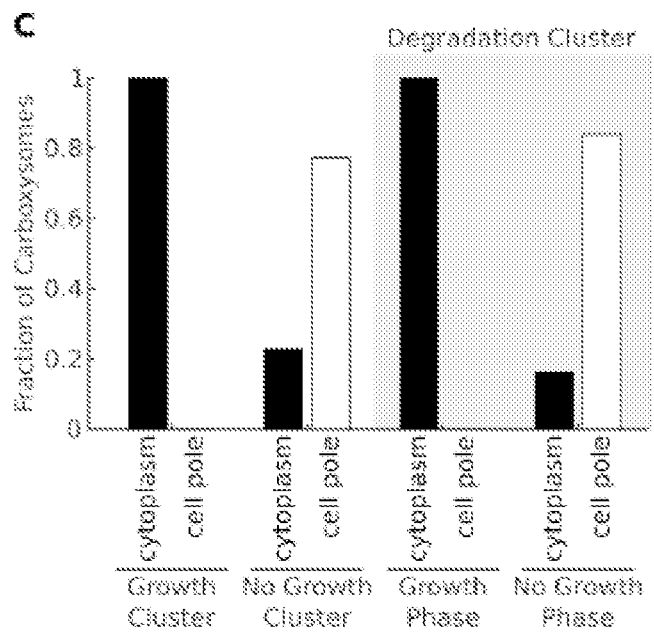
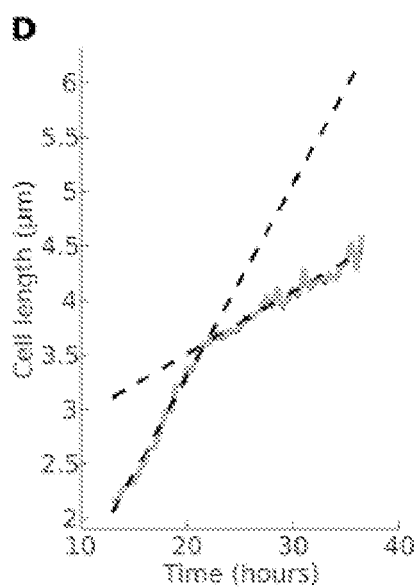
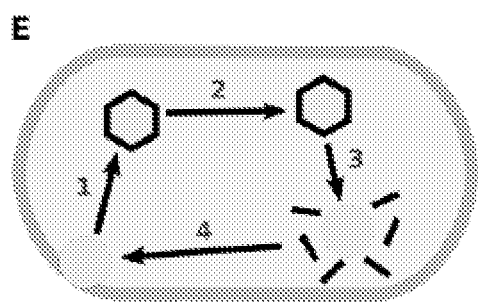
*FIG. 4 - continued*

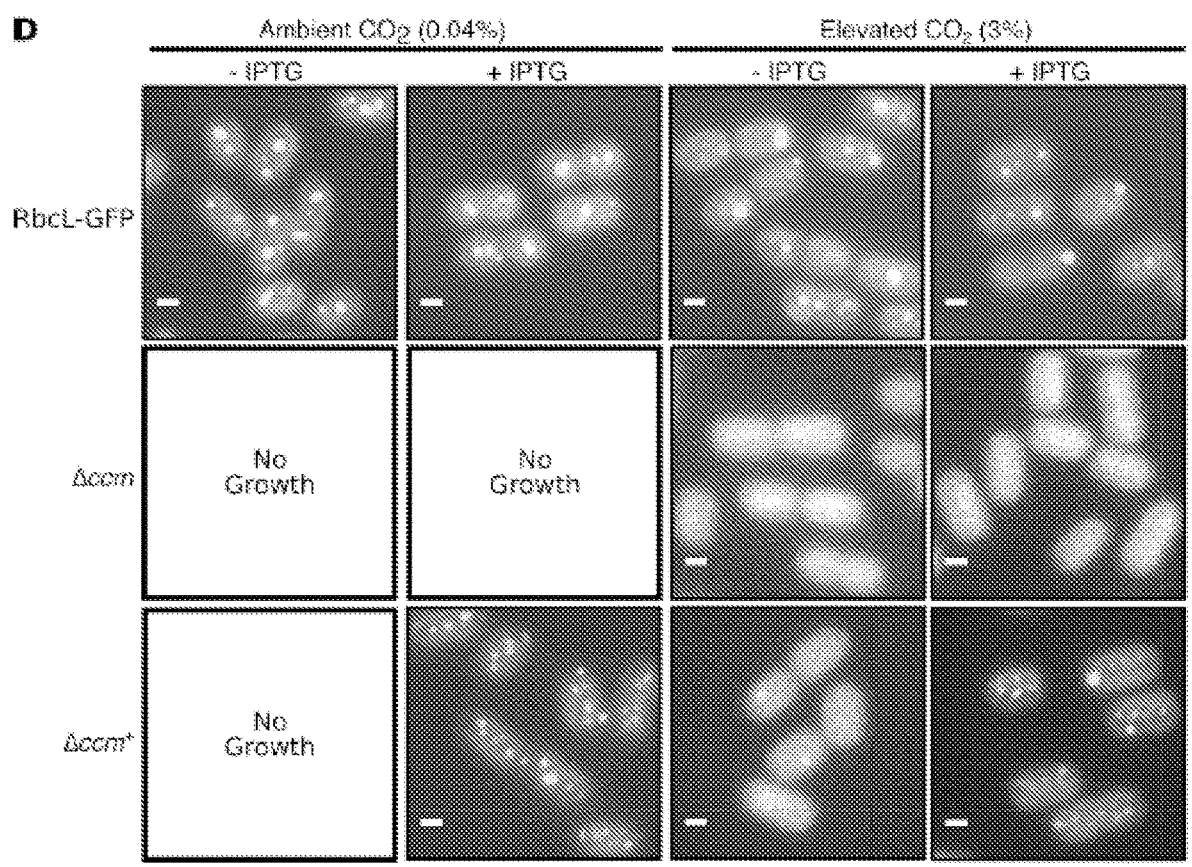
FIG. 5 - continued

A

B

C

D
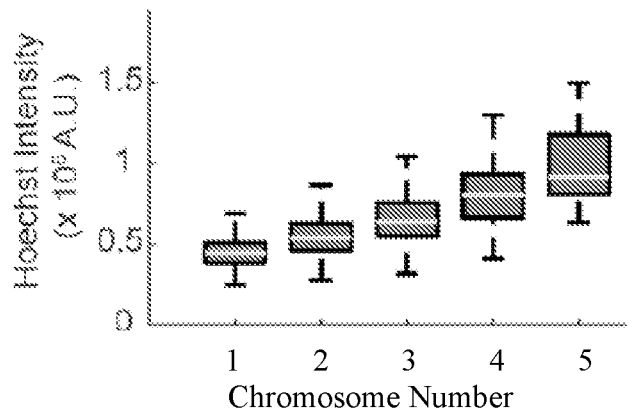
E
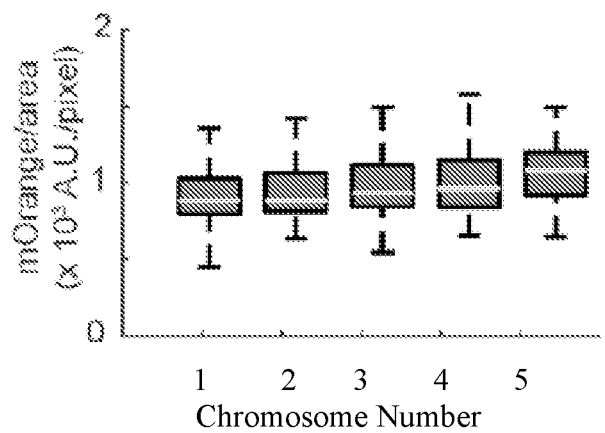
F
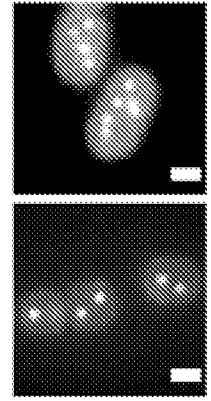
*FIG. 10 - continued*

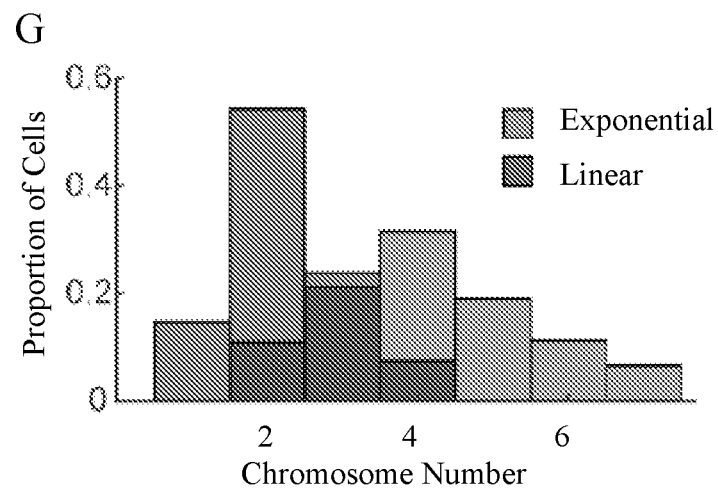
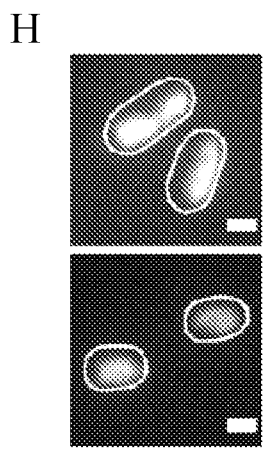
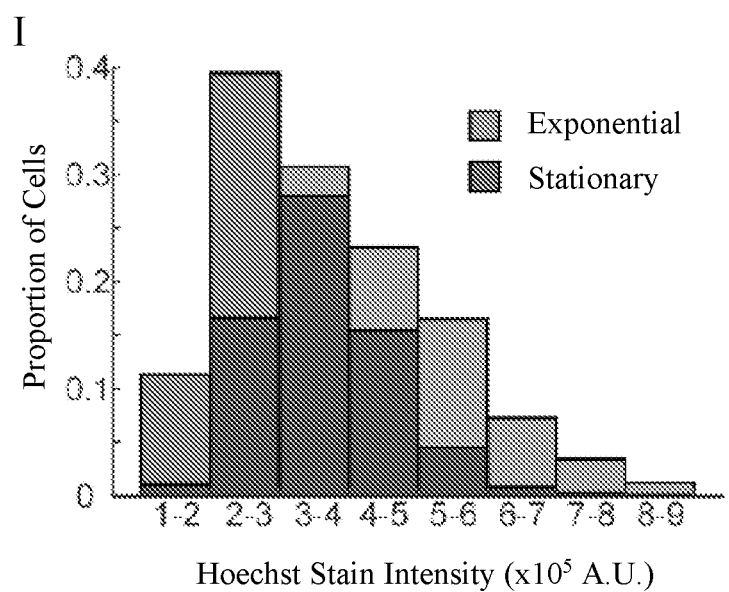
*FIG. 10 - continued*

A

B

C

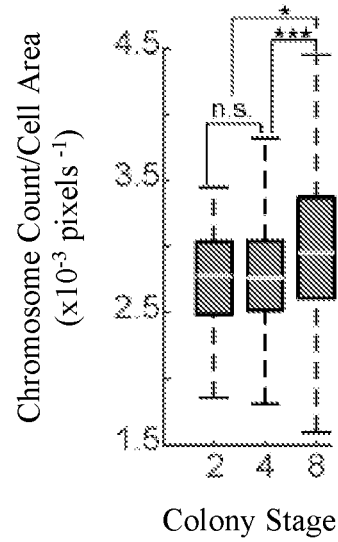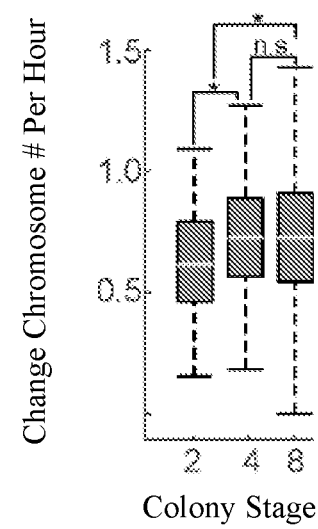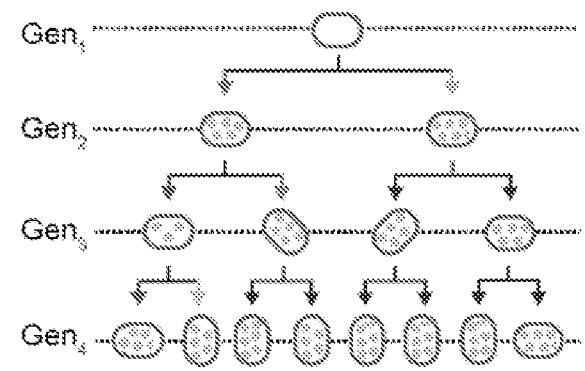
FIG. 11 - continued

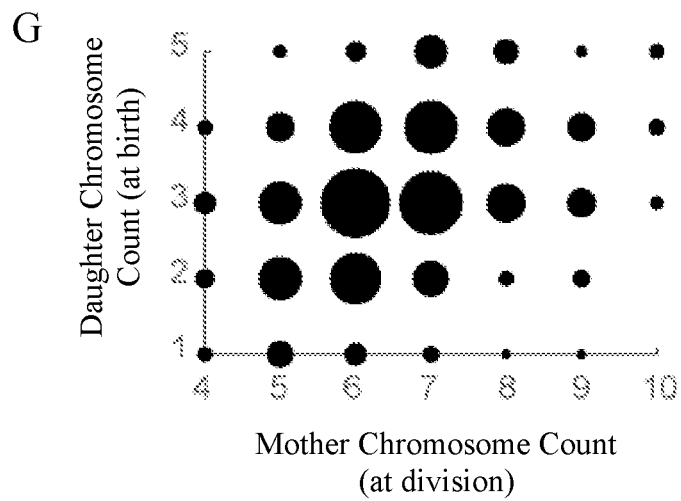
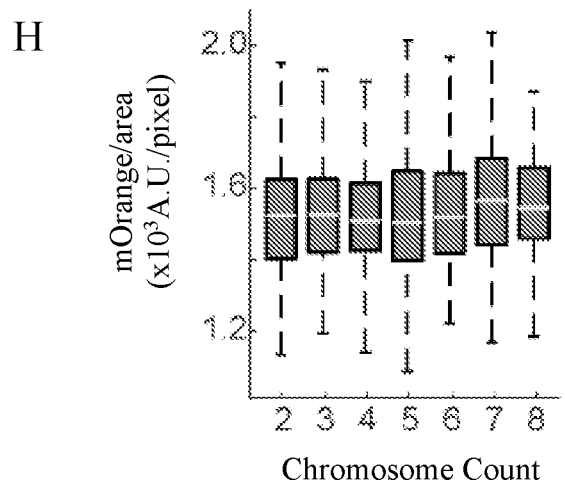
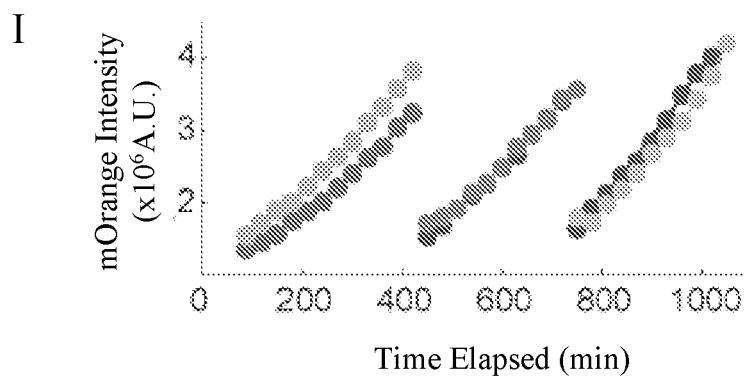
FIG. 11 - continued

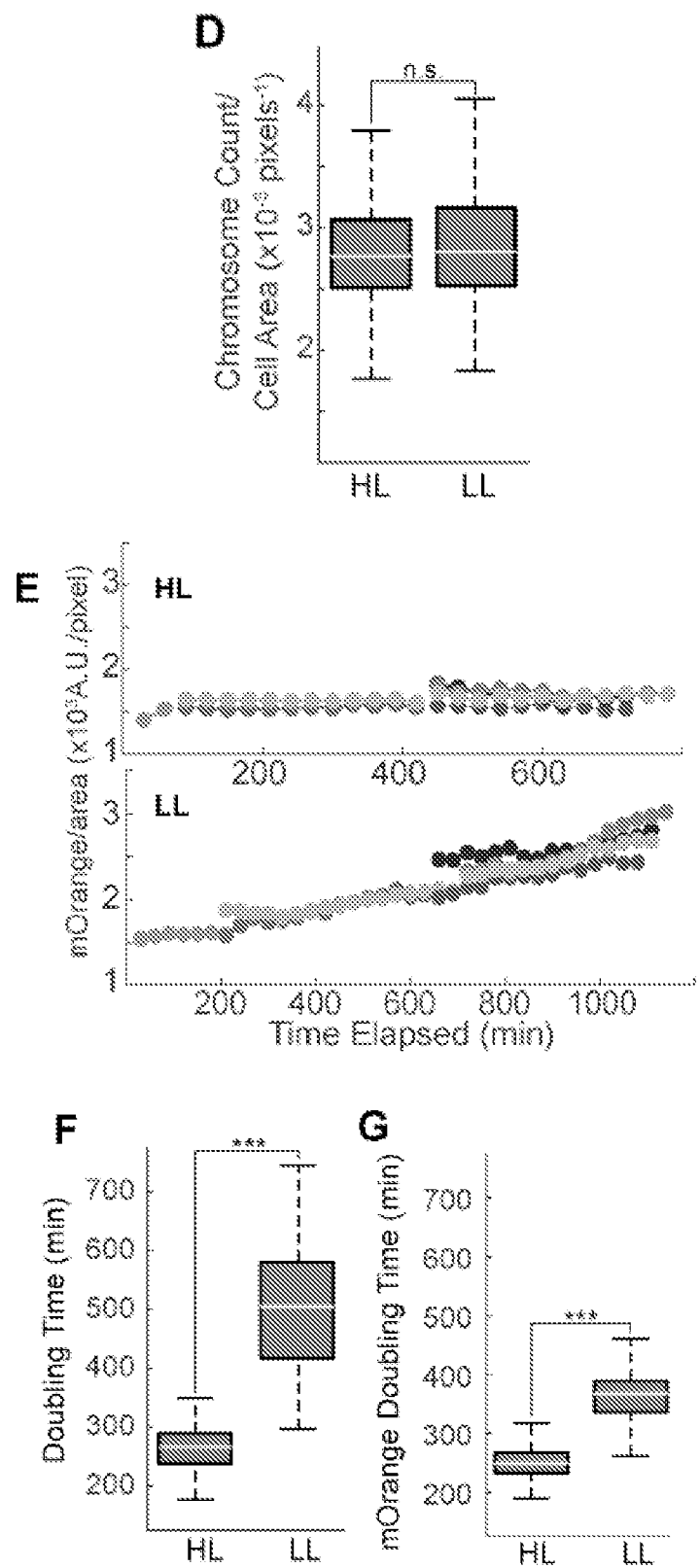
FIG. 12 - continued

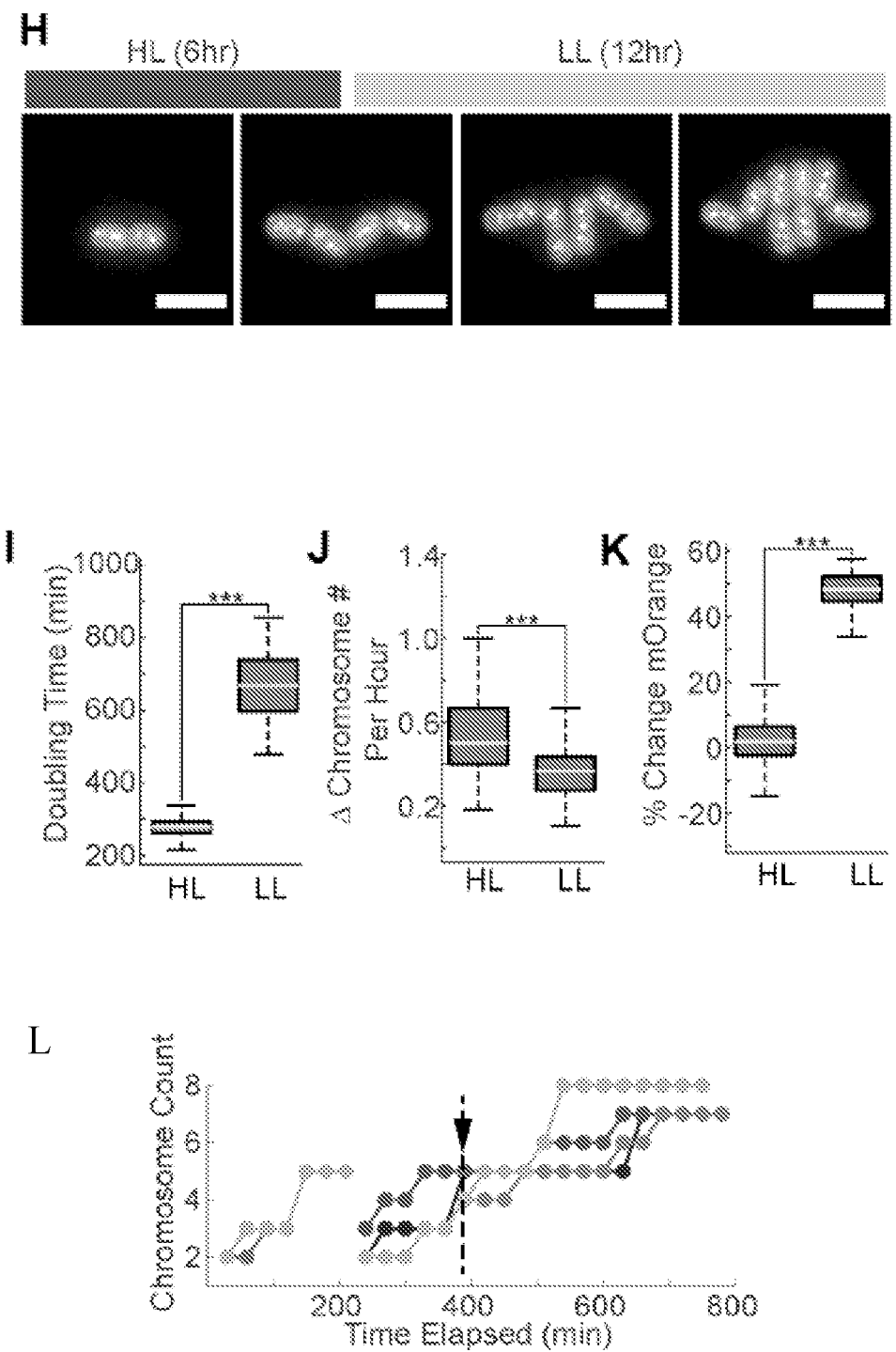
FIG. 12 - continued

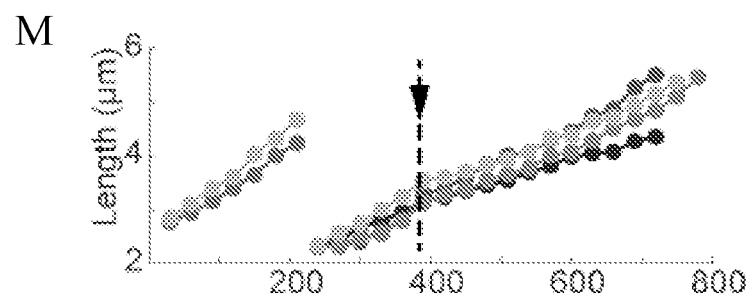
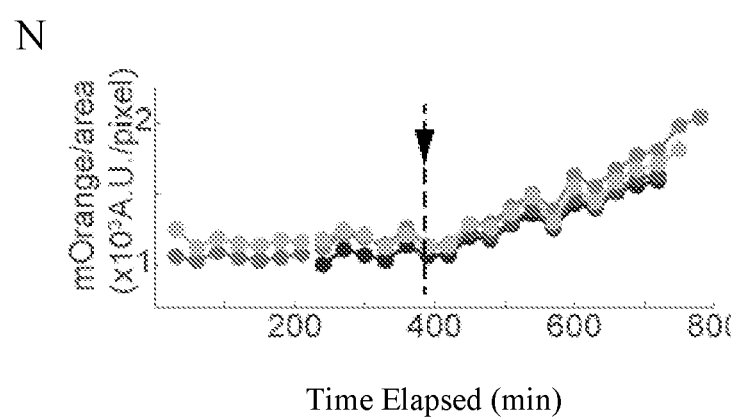
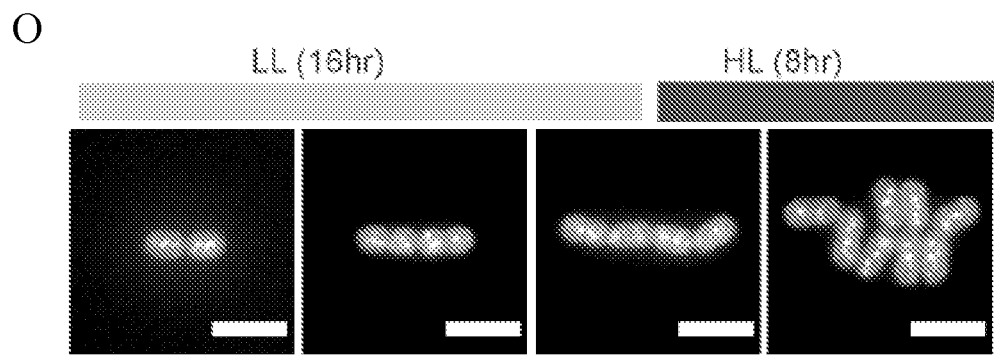
FIG. 12 - continued

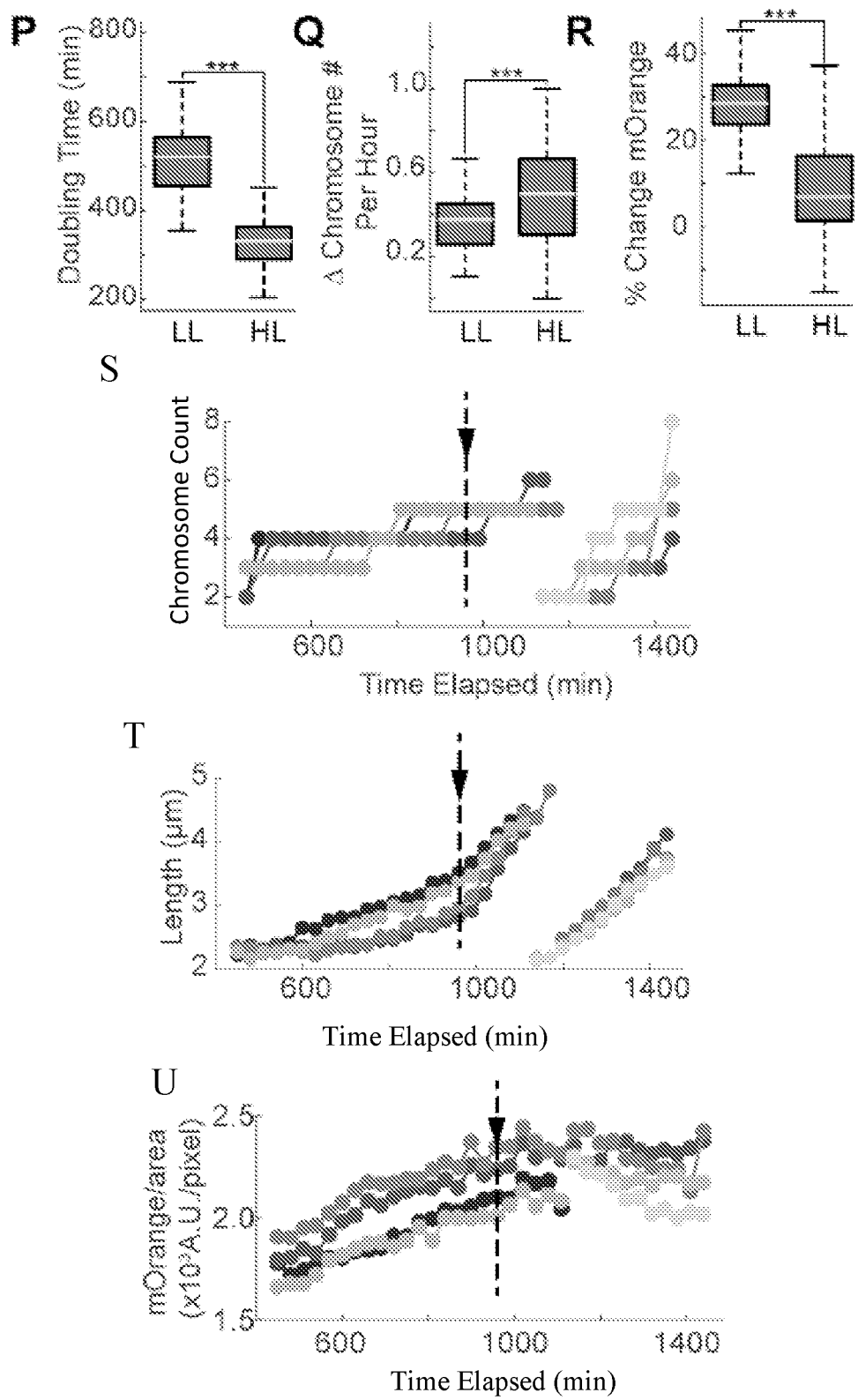
FIG. 12 - continued

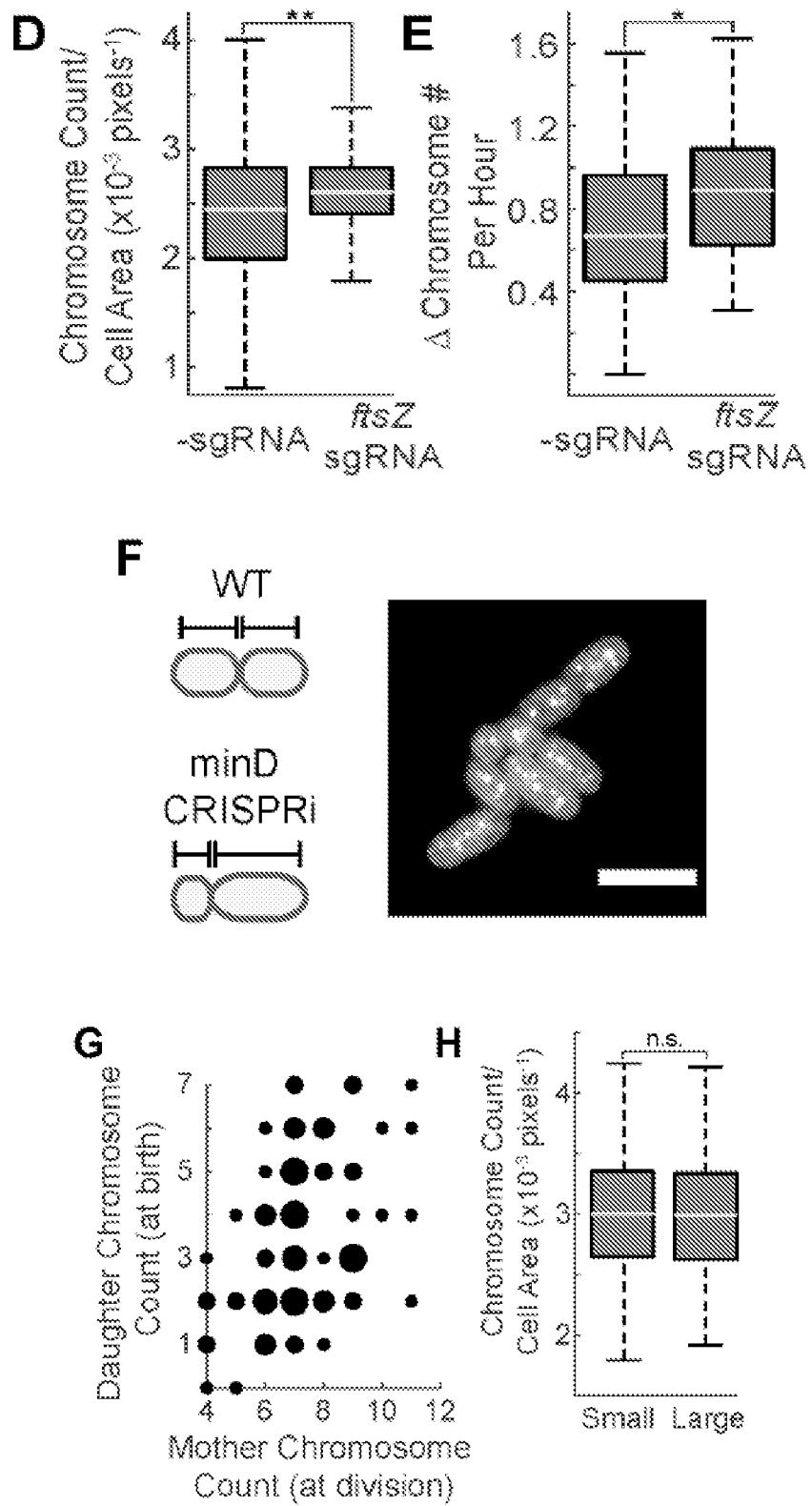
FIG. 13 - continued

E
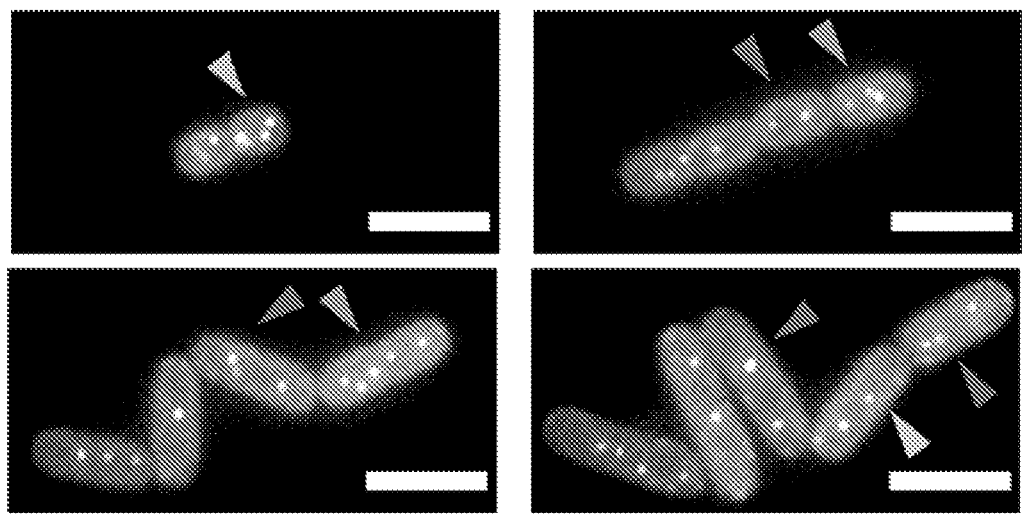
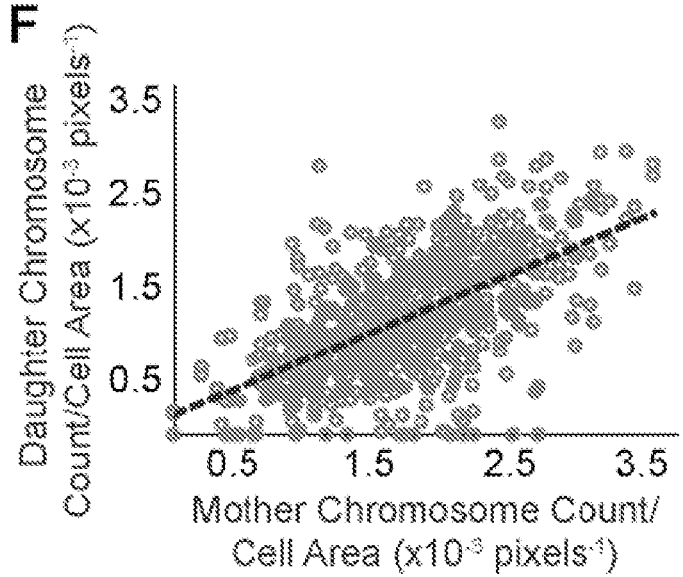
*FIG. 14 - continued*

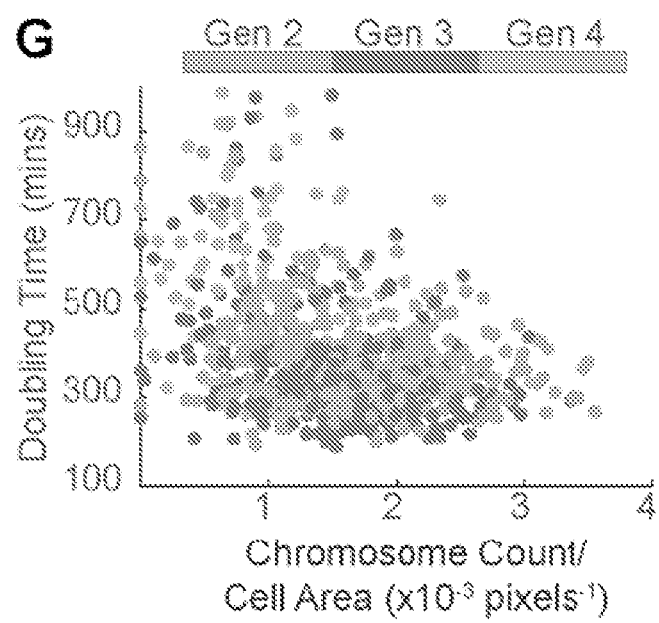
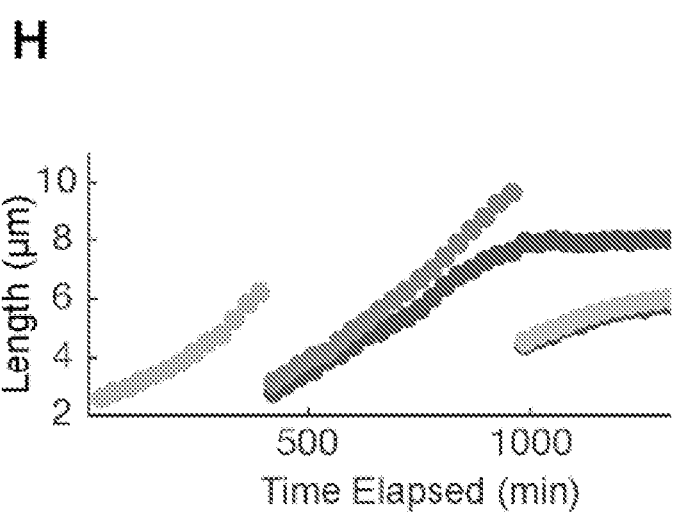
*FIG. 14 - continued*

I
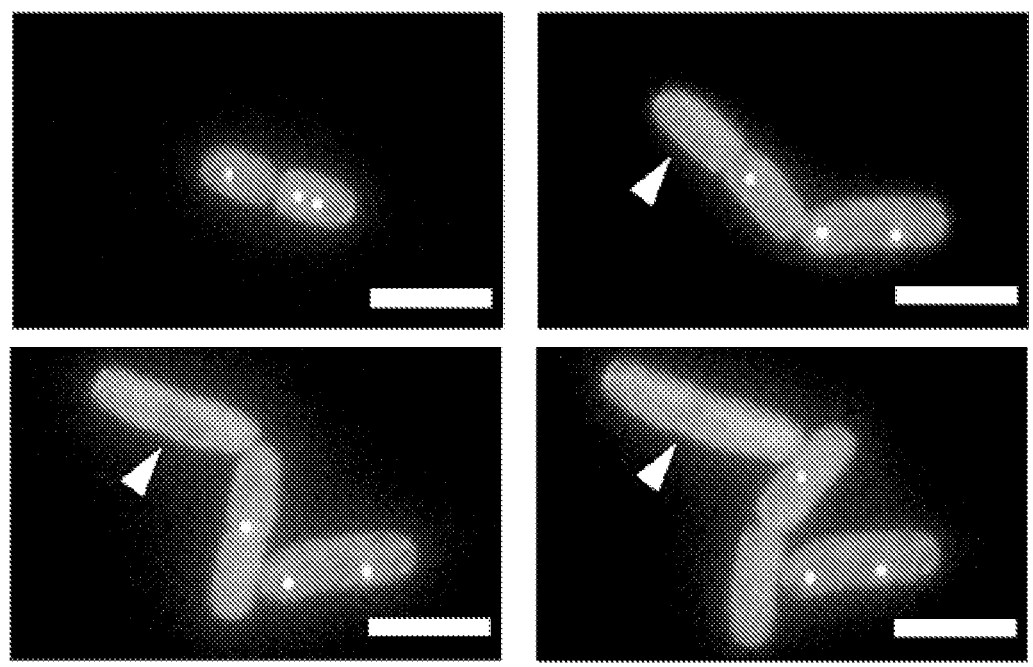
FIG. 14 - continued

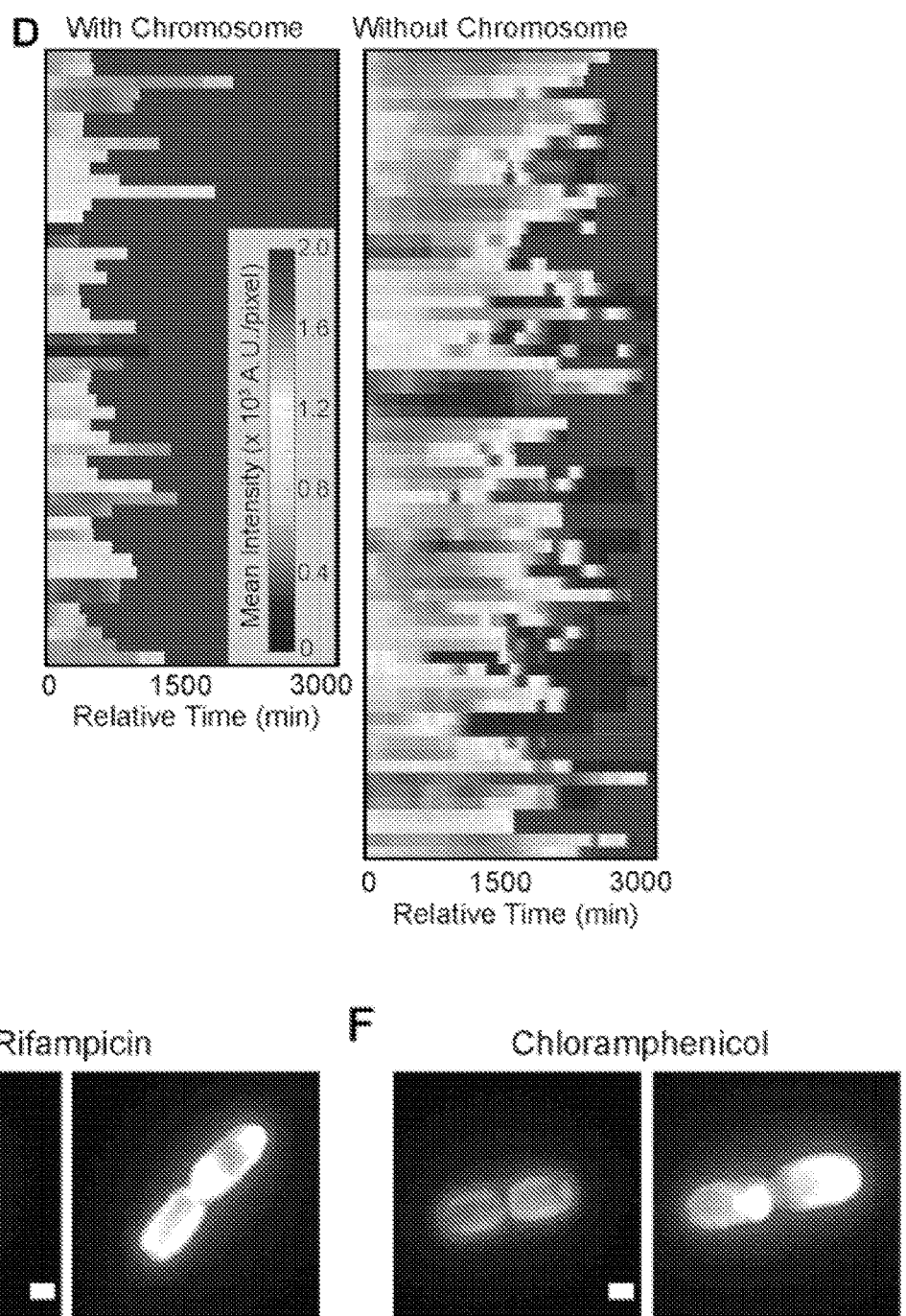
FIG. 15 - continued

METHODS FOR MEASURING AND OPTIMIZING THE STRUCTURE, LOCATION, AND ACTIVITY OF NATURAL AND ENGINEERED MICROCOMPARMENTS, ORGANELLES, AND MACROMOLECULES

CROSS-REFERENCE TO RELATED APPLICATIONS

This application claims the benefit of U.S. Provisional Application No. 62/935,738, filed Nov. 15, 2019.

STATEMENT OF GOVERNMENT INTEREST

This invention was made with government support under grant number GM008759 awarded by the National Institutes of Health, and grant number DE-SC0019306 awarded by the U.S. Department of Energy. The government has certain rights in the invention.

REFERENCE TO AN ELECTRONIC SEQUENCE LISTING

The contents of the electronic sequence listing (17-099-205-SEQ-CU-CAMERON_ST25.txt; Size: 7,402 bytes; Date of Creation: Dec. 25, 2020; and Date of Modification: Dec. 28, 2020) is herein incorporated by reference in its entirety.

FIELD OF INVENTION

This invention relates to methods and devices for measuring and optimizing the structure, location, and activity of natural and engineered microcompartments, organelles, chromosomes, and macromolecules.

BACKGROUND OF THE INVENTION

Bacteria encapsulate metabolic enzymes inside protein shells to modulate activity. These structures, termed "bacterial microcompartments" ("BMCs"), provide a competitive advantage to the bacterium and diverse, but structurally related structures perform important reactions. Carboxysomes, BMCs found in cyanobacteria, fix ~35% of global carbon and are being used to improve crops; homologous structures are critical in pathogenesis and could be novel targets for antibiotics; engineered versions can be used as nano-reactors for tailored biochemical reactions. A major limitation in the application of BMCs is that there is currently no way to measure the activity of the individual structures, which is critical for understanding their functions and optimizing them for enhanced carbon fixation for example.

SUMMARY OF THE INVENTION

The present invention provides novel method of diluting the structures in the cell population, such that individual cells, dependent on the activity of the structures, become single measurement devices. The approaches and techniques taught herein can be applied to all BMCs, organelles, and macromolecules, and could provide a universal method for the design and optimization of novel ones and understanding of the diverse structures and functions.

Essential structures linked to bacterial growth and disease and templates for biotechnological engineering and carbon fixation have not been harnessed because of a lack of a way to measure their activity. The present invention provides a way to overcome these hurdles and find a high throughput method to measure the activities of thousands of individual BMCs. The technologies taught herein can be used to in numerous applications including as a screen for increased/novel activities and target/screen for antibiotics.

Metabolic engineering of fuels/chemicals suffered from low flux from substrate to product; these structures concentrate substrates and enzymes to promote reactivity through metabolic channeling. They are general protein structures that can be loaded with cargo, but importantly, the shells are selectively permeable to small molecules and enable the generation of a unique biochemical environment within the cell cytoplasm for optimal enzyme activity.

In a first aspect the present invention provides a method of creating a bacterial strain with inducible and detectable carboxysomes. The method can include the steps of incorporating a labeled carbon-fixation enzyme into the genome of a bacterium, deleting all or a portion of the ccm operon from the bacterium, and reintroducing a ccm operon comprising an inducible promoter to create a Δccm+ strain.

In an advantageous embodiment the bacterium is a cyanobacteria. The labeled carbon-fixation enzyme can be a GFP-labeled carbon-fixation enzyme. The GFP-labeled carbon-fixation enzyme can be green fluorescent protein (GFP)-labeled Rubisco.

In an advantageous embodiment the inducible promoter is an isopropyl β-D-1-thiogalactopyranoside (IPTG)-inducible promoter. The carbon-fixation enzyme can be a carboxysome-associated protein.

The method according to the first aspect can include the step of growing the Δccm+ strain in ambient $CO_2$ in the presence of IPTG to initiate carboxysome expression. In further embodiments the method according to the first aspect can include the steps of growing the Δccm+ strain in ambient $CO_2$ in the presence of IPTG to initiate carboxysome expression and removing IPTG in the resulting cells to prevent formation of new carboxysomes.

In a second aspect the present invention provides a second method of creating a bacterial strain with inducible and detectable carboxysomes. The method can include the steps of incorporating a labeled carboxysome-associated protein into the genome of a bacterium, and modifying the ccm operon of the bacterial strain to be under the control of an inducible promoter.

In a third aspect the present invention provides a method of creating a bacterial strain with inducible and detectable bacterial microcompartments (BMCs). The method can include the steps of incorporating one or more labeled BMC enzymes into the genome of a bacterium, deleting all or a portion of the operon or gene responsible BMC functionality from the bacterium and reintroducing the gene or operon comprising an inducible promoter into the bacterium to create a bacterial strain with a controllable BMC expression or production. In an advantageous embodiment the bacterium is a cyanobacteria. The labeled BMC enzyme can be a GFP-labeled enzyme. The inducible promoter can be an isopropyl β-D-1-thiogalactopyranoside (IPTG)-inducible promoter In a fourth aspect the present invention provides a second method of creating a bacterial strain with inducible and detectable BMCs. The method can include the steps of incorporating a labeled BMC-associated protein into the genome of a bacterium and modifying BMC-associated gene or operon of the bacterial strain to be under the control of an inducible promoter.

In a fifth aspect the present invention provides a method of controlling carboxysome number, growth, or expression in a bacterial strain. The method can include the steps of providing a bacterial strain having a ccm operon under the control of an inducible promoter, maintaining the bacterial strain in ambient $CO_2$ or other concentration wherein carboxysome expression is inhibited, and exposing the bacterial strain to the agent that induces the promoter, whereby inducing the promoter increases carboxysome number, growth, or expression.

The method of controlling carboxysome number, growth, or expression in a bacterial strain according to the fifth aspect can further include the steps of removing the agent from the bacterial strain and maintaining the bacterial strain in ambient $CO_2$ or other concentration wherein carboxysome expression is inhibited, whereby continued growth and division of the bacterial strain results in a decrease on the number of carboxysomes in progeny cells.

In a sixth aspect the present invention provides a second method of controlling carboxysome number, growth, or expression in a bacterial strain. The method can include the steps of providing a bacterial strain having a BMC gene or operon under the control of an inducible promoter and exposing the bacterial strain to an agent that induces the promoter, whereby inducing the promoter increases the BMC number, growth, or expression.

In a seventh aspect the present invention provides a method of selectively inhibiting chromosome replication in a cell. The method can include the steps of providing a cell strain with an inducible guide RNA providing CRISPRi of dnaX where the strain is engineered to express dCas9 and contacting the cell with an induction agent of the inducible guide RNA thereby inhibiting transcription of dnaX. The inducible guide RNA (sgRNA) is an IPTG inducible guide RNA. In an advantageous embodiment the bacterium is a cyanobacteria. In further advantageous embodiments the cell is a polyploid bacteria.

In an eighth seventh aspect the present invention provides a method of selectively inhibiting cell division or increasing chromosome number in a cell. The method can include the steps of performing CRISPRi of ftsZ or an ftsZ analog by contacting the cell with an induction agent of the inducible ftsZ guide RNA.

In a ninth aspect the present invention provides a method of selectively generating uneven division of a cell comprising the step of performing CRISPRi of minD or a minD analog by contacting the cell with an induction agent of the inducible minD guide RNA.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
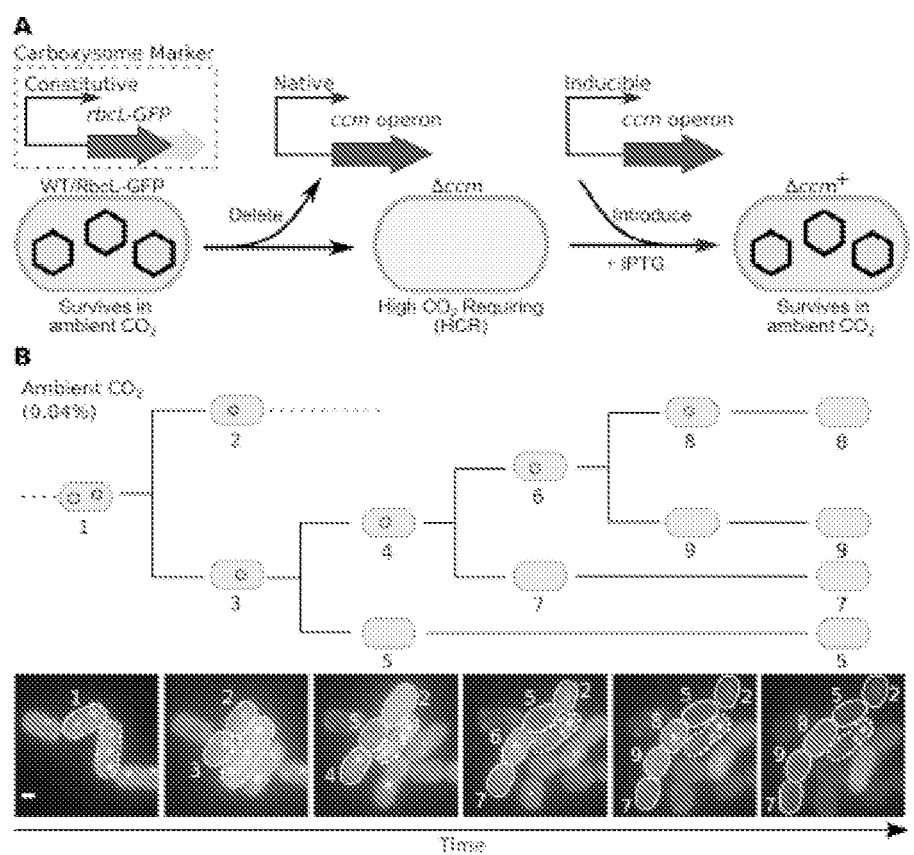
FIG. 1 is a set of illustrations, images and graphs depicting control carboxysome expression. (A) Constitutively expressed RbcL-GFP allows for Rubisco visualization. The native ccm operon was knocked out, producing the HCR strain Δccm. An IPTG-inducible version of the ccm operon was reintroduced to create the Δccm+ strain, resulting in IPTG-dependent carboxysome expression and growth rescue in ambient $CO_2$. (B) Family tree of Δccm+ cells after IPTG removal in ambient $CO_2$. A dying cell is indicated with a dashed white outline. Carboxysomes in this cell remain static and brightly fluorescent throughout the experiment, indicating that photobleaching has a negligible effect on GFP intensity within the timespan of the experiment. (C) Family tree of Δccm+ cells after IPTG removal in elevated $CO_2$. (D-F) Population-level characterization of growth of the Δccm+ strain upon IPTG removal in ambient $CO_2$. (D) Average number of carboxysomes per cell decreases as cells divide, diluting pre-existing carboxysomes among the growing population. (E) Growth rate is proportional to average number of carboxysomes within a cell. n=191, 108, 207, 604, and 259 for 4+, 3, 2, 1, and 0 carboxysomes, respectively. One-way ANOVA with Tukey-Kramer multiple comparison test was used for statistics (see Methods). ****$p<0.0001$. (F) Growth rate versus generation number. Cells with 3+, 2, 1, and 0 carboxysomes are indicated in the figure. See FIGS. 7A to 7D for individual plots.

Carboxysomes, prototypical bacterial microcompartments (BMCs) found in cyanobacteria, are large (~1 GDa) and essential protein complexes that enhance $CO_2$ fixation. While carboxysome biogenesis has been elucidated, their activity dynamics, lifetime, and degradation have been unstudied due to an inability to analyze individual BMCs over time in vivo. Here, a fluorescence-imaging platform has been developed and is reported herein to simultaneously measure carboxysome number, position, and activity over time in a growing cyanobacterial population, allowing individual carboxysomes to be clustered based on activity and spatial dynamics. We discover BMC degradation, characterized by abrupt activity loss followed by polar recruitment of the deactivated complex, and a sub-class of ultra-productive carboxysomes. Altogether, the results uncover the BMC lifecycle post-biogenesis, and describe an important method for measuring activity of single macromolecular complexes in vivo.

Bacterial microcompartments (BMCs) are a widespread class of protein-based organelles found in at least 23 bacterial phyla (1). Comprised of a protein shell encapsulating an enzymatic interior, they increase catalytic efficiency of luminal enzymes while preventing the escape of toxic or volatile intermediates into the cytoplasm. The carboxysome, an essential BMC in cyanobacteria, encapsulates the enzymes ribulose 1,5-bisphosphate carboxylase/oxygenase (Rubisco) and carbonic anhydrase (2, 3). The carboxysome functions in the $CO_2$ concentrating mechanism (CCM) by sequestering $CO_2$ in its interior, thereby maximizing Rubisco's carboxylation rate, while minimizing its oxygenation side reaction. The CCM of cyanobacteria is largely responsible for their efficient $CO_2$ fixation; cyanobacteria perform more than 35% of global $CO_2$ fixation, despite comprising less than 0.2% of photosynthetic biomass. The efficient CCM has inspired recent efforts to incorporate carboxysomes into plants for increased crop yields. Other BMCs are involved in metabolism of 1,2-propanediol, ethanolamine, and plant-derived polysaccharides. The shell proteins are evolutionarily conserved and targeting them could be used to modulate function. This includes homologs of BMC-hexamer, BMC-pentamer, and BMC-tandem domain shell proteins. Many BMCs are critical for pathogenesis (e.g Pdu Metabolosome in Salmonella sp.) and can thus be targets of novel antibiotics if their activity can be screened such as with the techniques taught herein.

Previous studies of cyanobacterial carboxysomes revealed that the interior is formed first through a series of protein-protein interactions, followed by encapsulation through assembly of the protein shell. However, carboxysome functionality post-biogenesis, including $CO_2$ fixation dynamics, lifetime, and turnover, has not been analyzed. To address this, a method for assessing carboxysome functionality at the single protein complex level in vivo was developed. Time-lapse fluorescence microscopy was employed to track fluorescently labeled carboxysomes in single Synechococcus sp. PCC 7002 (hereafter PCC 7002) cells, chosen for their fast growth rate and industrial. Unlike bulk culture techniques, microscopy enables analysis of individual carboxysomes, and has been used to describe carboxysome organization within the cell. However, previous studies were unable to assess carboxysome activity and its relation to cell growth.

Here, individual carboxysomes were tracked over 63.5 hours as they were passed from mother to daughter cells until their eventual disappearance. As WT PCC 7002 cells generally contain 4-6 carboxysomes, a system for controlling carboxysome expression was developed to minimize the number of carboxysomes in each cell. Importantly, this system allows for determination of carboxysome activity; in a cell with only one carboxysome, under ambient (~0.04%) $CO_2$ levels, all $CO_2$ fixation and cell growth can be attributed to the catalytic activity of a single carboxysome, making growth rate an indicator of carboxysome activity over time.

Figure 5:
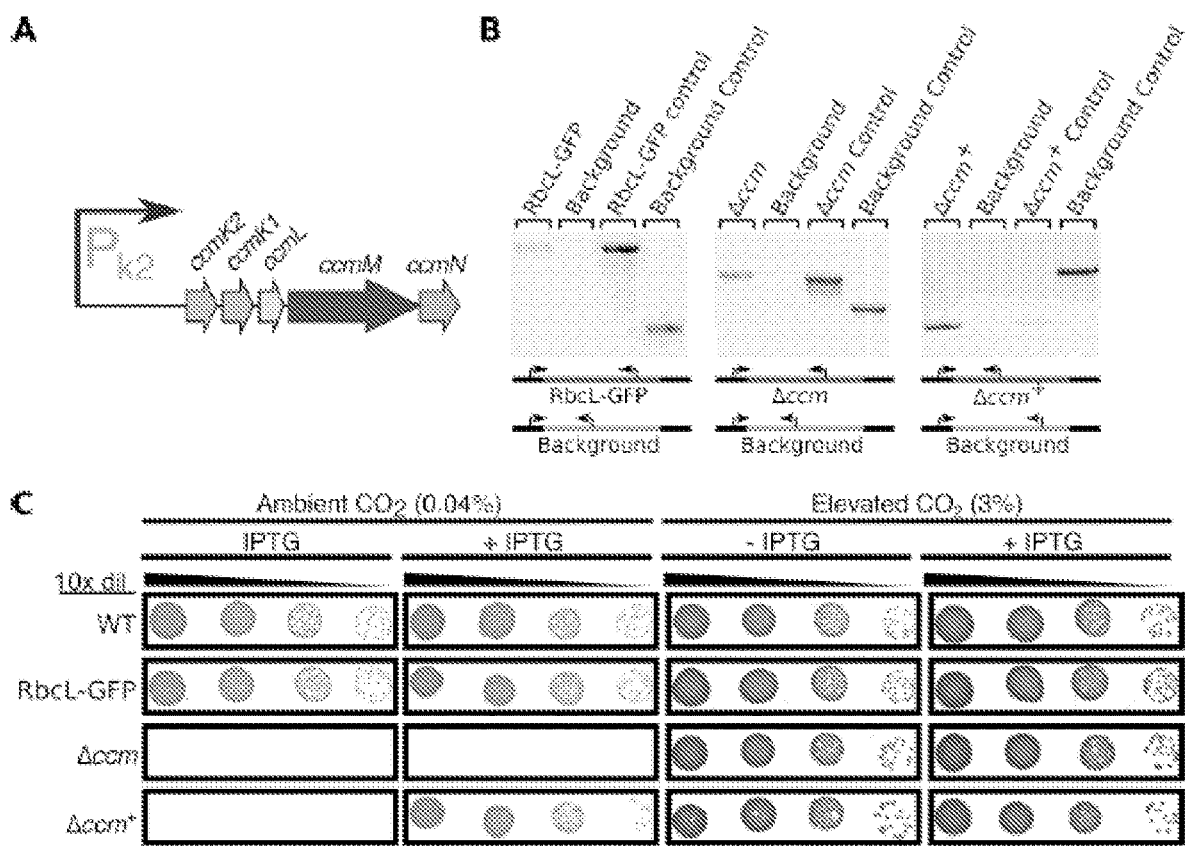
FIG. 5 is a set of illustrations and images depicting strain construction and characterization. (A) Gene diagram of ccm operon in PCC 7002, controlled by the constitutive pK2 promoter. (B) Colony PCR was used to confirm complete segregation of all strains used in this study. Presence of the insert band and absence of the background band indicated complete segregation. Arrows represent primers described in Table 3. (C) Spot plates used to assess growth in different conditions. (D) Fluorescence images show presence or absence of carboxysomes. Chlorophyll, dark gray; RbcL-GFP, light gray. Scale bars are 1 µm.

To create a strain with inducible and fluorescent carboxysomes, a green fluorescent protein (GFP)-labeled Rubisco (named RbcL-GFP) was incorporated into the PCC 7002 genome for carboxysome visualization. The ccm operon, which contains the majority of carboxysome-associated genes (FIG. 5A), was then knocked out resulting in the high $CO_2$ requiring (HCR) Δccm strain. The ccm operon was then reintroduced under an isopropyl β-D-1-thiogalactopyranoside (IPTG)-inducible promoter, creating the Δccm$^+$ strain (FIG. 1A). Segregation of all strains was confirmed via PCR (FIG. 5C). The Δccm$^+$ strain is capable of growth (FIG. 5) and carboxysome expression (FIG. 5D) in ambient $CO_2$ only in the presence of IPTG. Cells cultured in elevated (3%) $CO_2$ without IPTG followed by transfer to ambient $CO_2$ with IPTG exhibited growth only after a lag phase allowing for initial carboxysome formation. The Δccm$^+$ strain exhibits controllable carboxysome expression, and induced carboxysomes are indistinguishable from carboxysomes in the control strain, RbcL-GFP. It is contemplated that other means could be used as an alternative to the (IPTG)-inducible promoter, including induction using nickel, copper, aTc, or controlled through environment (light inducible) or nutrient stress (nblA). Alternative methods including nutrient depletion can be used to turn off and turn on carboxysome biogenesis-starve cells with nitrogen and then add nitrogen back.

Once expected behavior of the Δccm$^+$ strain was confirmed, Δccm$^+$ cells were grown in air with 1 mM IPTG to initiate carboxysome expression. IPTG was then removed to prevent formation of new carboxysomes, and individual cells were imaged over time in ambient or elevated $CO_2$. Family trees of representative cell lineages were created for each condition (FIGS. 1B and 1C). In both ambient and elevated $CO_2$, carboxysomes were passed from mother to daughter cell, resulting in a decrease in number of carboxysomes per cell from generation to generation. In ambient $CO_2$, daughter cells that did not receive a carboxysome immediately stopped growing (cells 5, 7, and 9 in FIG. 1B), while daughter cells that did receive a carboxysome (cells 3, 4, 6, and 8 in FIG. 1B) continued growing until disappearance of the carboxysome punctum (cell 8, FIG. 1B). In contrast, growth of Δccm$^+$ in elevated $CO_2$ was not dependent on the presence of carboxysomes; all cells exhibited growth regardless of carboxysome number (FIG. 1). These results demonstrate that growth in ambient $CO_2$ is dependent on the presence of at least one functional carboxysome in the cell.

Figure 6:
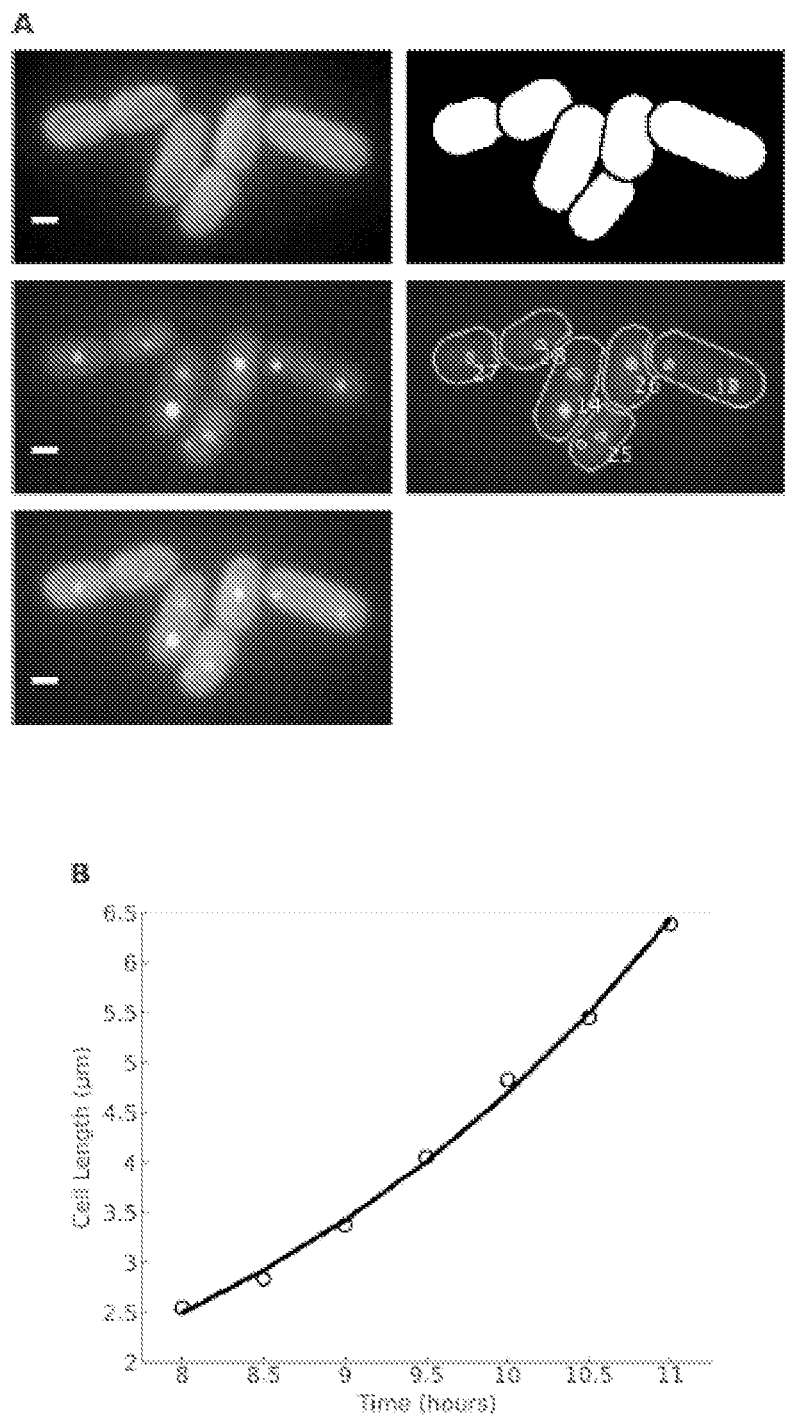
FIG. 6 is a set of images and a graph depicting computational analysis of carboxysomes and growth parameters. (A) Fluorescence images of PCC 7002. Chlorophyll fluorescence, RbcL-GFP, merge, (left, top to bottom, respectively) and computed cell masks and carboxysome positions with cell IDs labeled (right, top and bottom, respectively). Scale bars are 1 µm. (B) Representative WT cell growth. Open circles indicate actual data, and line is exponential curve fit to the data.

Custom MATLAB scripts were used to count the number and position of GFP puncta per cell, measure single-cell growth rates based on change in cell length over time, and track individual carboxysome inheritance patterns across the population (see Methods, below and FIGS. 6A and 6B). Upon IPTG removal in ambient $CO_2$, the number of carboxysomes per cell decreased rapidly within the growing Δccm$^+$ population, reaching an average of one carboxysome per cell by 26.5 hours (FIG. 1D). Growth rates correlated with the average number of carboxysomes in each cell (FIG. 1E), indicating that in ambient $CO_2$, cell growth is directly proportional to carboxysome-associated $CO_2$ fixation.

The growth rate of the Δccm$^+$ population gradually decreased from generation to generation, as carboxysomes were diluted across the population over time (FIG. 1F and FIGS. 7A to 7D). As expected, all daughter cells that did not inherit a carboxysome, regardless of generation, immediately stopped growing. This sudden halt of growth indicates that alternative carbon sources, such as glycogen, are incapable of maintaining cell growth in the absence of carboxysomes.

Figure 7:
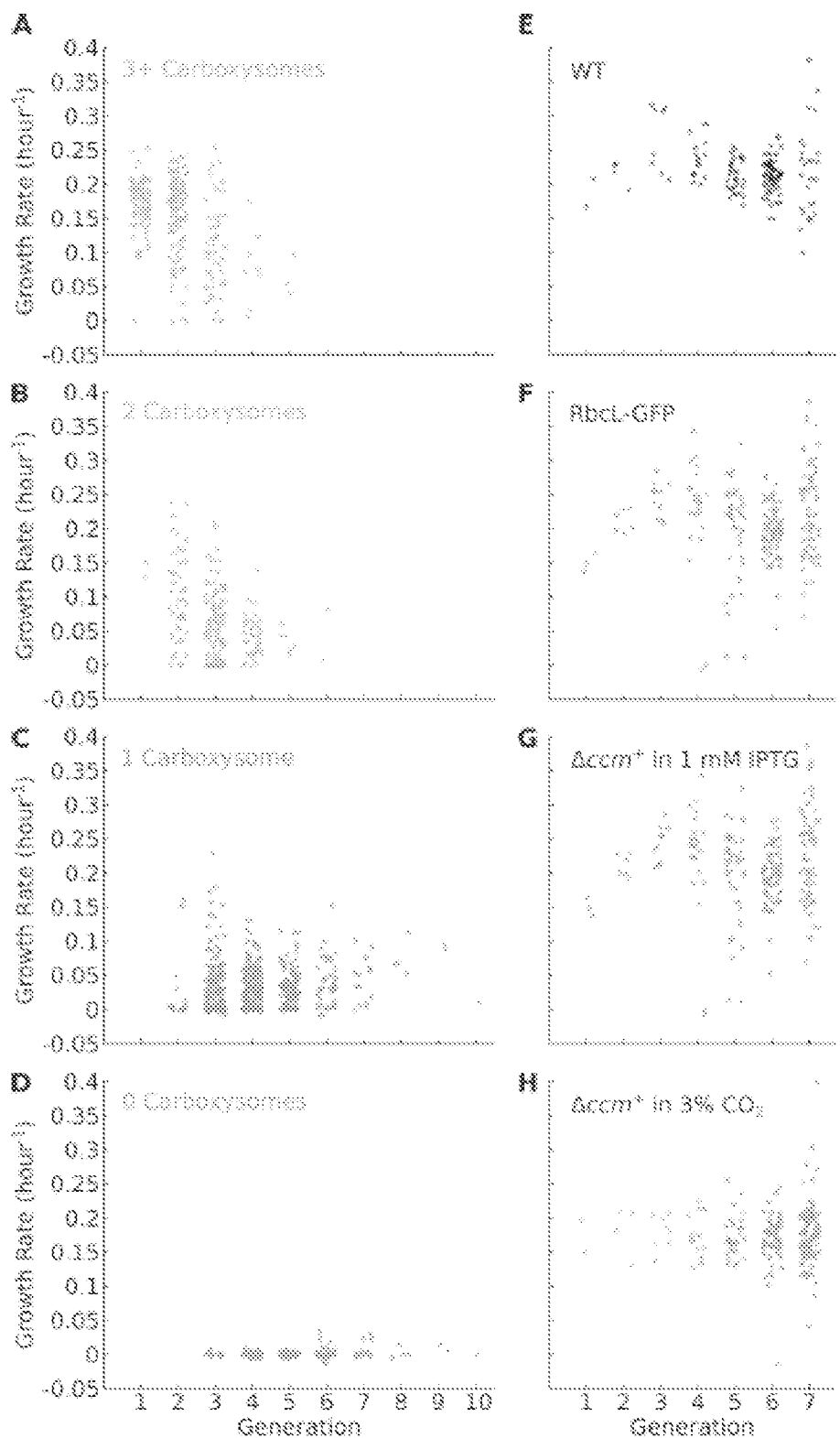
FIG. 7 is a set of graphs depicting IPTG washout in ambient $CO_2$ causes gradual decrease in growth rate in $\Delta ccm+$ population. (A-D) Growth rate versus generation number for $\Delta ccm^+$ cells with an average of 3+(A), 2 (B), 1 (C), or 0 (D) carboxysomes after IPTG removal in ambient $CO_2$. Growth rate versus generation number for WT (E), RbcL-GFP (F), $\Delta ccm^+$ with 1 mM IPTG (G), and $\Delta ccm^+$ in elevated $CO_2$ (H), where points indicates average number of carboxysomes in the cell, as in FIGS. S3A to S3D.
Figure 8:
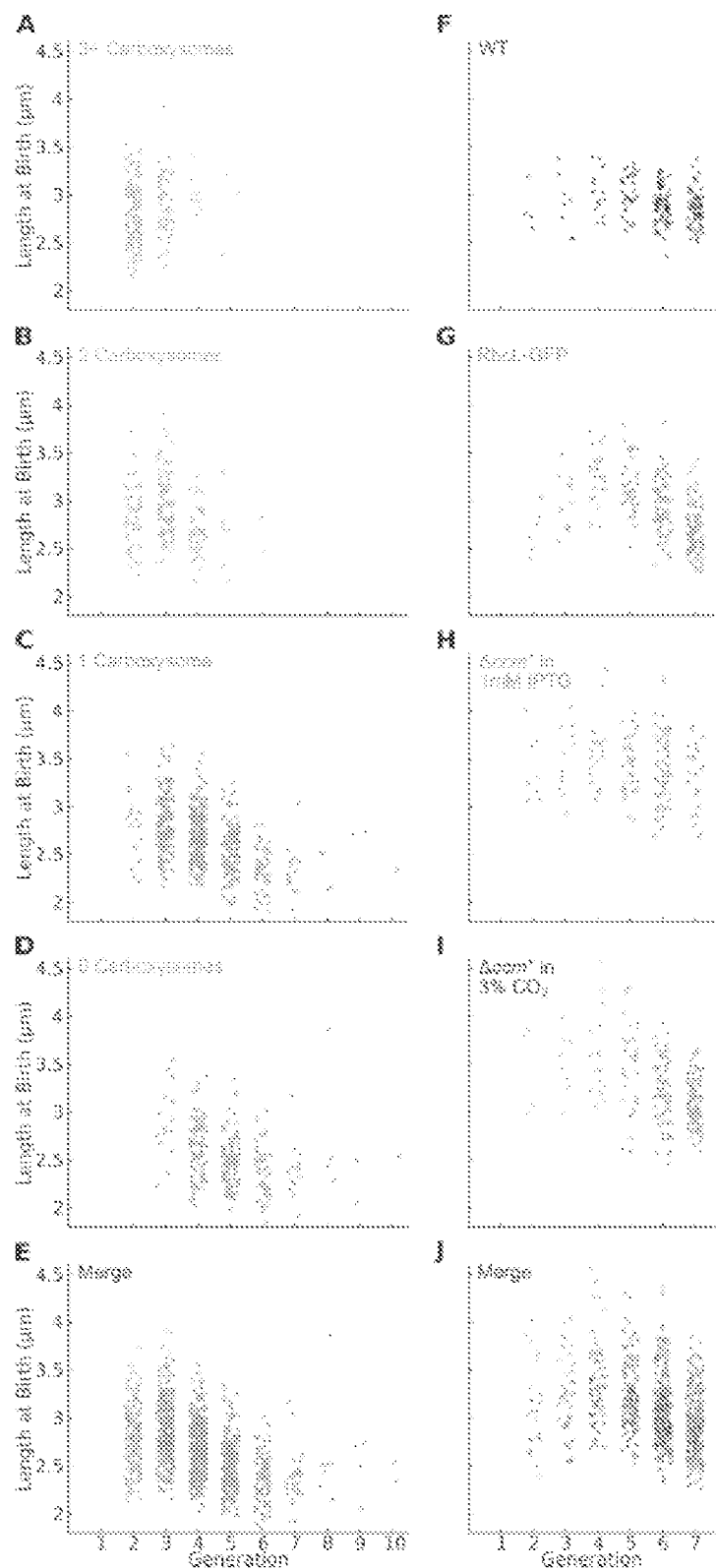
FIG. 8 is a set of graphs depicting that the length at birth decreases in $\Delta ccm^+$ population upon IPTG washout in ambient $CO_2$. (A-E) Length at birth versus generation number for $\Delta ccm^+$ cells with an average of 3+(A), 2 (B), 1 (C), or 0 (D) carboxysomes after IPTG removal. (E) Merge of FIG. 4A to 4D. (F-J) Length at birth versus generation number for WT (F), RbcL-GFP (G), $\Delta ccm^+$ with 1 mM IPTG (H), and $\Delta ccm^+$ in elevated $CO_2$ (I), where a point indicates average number of carboxysomes in the cell, as in 4A-4D. (J) Merge of FIG. 4F to 4I.

In contrast to the Δccm$^+$ strain, WT and RbcL-GFP control cells maintained a high and constant growth rate over multiple generations (FIGS. 7E and 7F). When Δccm$^+$ cells were grown in the presence of 1 mM IPTG, new carboxysomes were continuously produced, and multi-generational growth rates were identical to WT and RbcL-GFP cells (FIG. 7G). When IPTG was removed from Δccm$^+$ cells grown in elevated $CO_2$, the growth rate remained identical to the WT and RbcL-GFP controls, despite rapid dilution of carboxysomes in the population (FIG. 7H).

To further support the link between carboxysome activity and cell growth, changes in cell size from generation to generation were analyzed. Cell size has been shown to be a function of carbon uptake in E. coli. Similarly, cell size in PCC 7002 is regulated in response to light levels. Therefore cell size should gradually decrease with increasing generation number in the Δccm+ population, as loss of carboxysomes leads to a decreased ability to assimilate carbon. As expected, length at birth gradually decreased with increasing generation number in the Δccm+ strain in ambient $CO_2$ upon IPTG removal (FIGS. 8A to 8E), whereas lengths at birth for WT, RbcL-GFP, Δccm+ in the presence of 1 mM IPTG, and Δccm+ in elevated $CO_2$ remained constant over time (FIGS. 8F to 8J).

Single-cell data at single-carboxysome resolution was then analyzed to uncover differences in individual carboxysome activity profiles across the entire multi-generational population. The initial frame in which a cell contained one carboxysome was identified; from that frame onward, that cell and all of its descendants were grouped into a single-carboxysome tree. Cell lengths for each frame in the single-carboxysome tree were summed to obtain the length accumulation over time associated with that tree's carboxysome. Cell length provides a good proxy for biomass accumulation, as cell width remains constant in experimental conditions. This measurement, denoted 'net productivity', indicates the activity of a single carboxysome over time, as all biomass accumulation and cell growth can be attributed to a single carboxysome (FIG. 2A).

The net productivity profiles of single-carboxysome trees were clustered into 4 categories: 'Too short', 'No growth', 'Growth', and 'Degradation' (FIGS. 2B and 2C). The 'Too short' cluster consists of single-carboxysome trees where the carboxysome lasted less than 13 hours, and were excluded in downstream analyses. The 'No growth' cluster contained non-functional carboxysomes that were unable to support cell growth, as seen by a constant net productivity of zero. The 'Growth' cluster contained carboxysomes that exhibited a positive net productivity rate throughout the experiment, while the 'Degradation' cluster was categorized based on a positive net productivity rate decreasing to zero, resulting in sudden growth arrest (all clustered data in FIG. 9).

There was a large degree of heterogeneity in net productivity within the 'Growth' cluster. Approximately 67% of carboxysomes within this cluster maintained a constant rate of increase in net productivity throughout the experiment, and are therefore referred to as 'non-aging' (FIG. 2B). One remarkable carboxysome reached a net productivity of 18 μm in less than 50 hours (FIG. 2D, top), single-handedly supporting seven generations of growth (FIG. 2D, bottom). The remaining third of single-carboxysome trees in the 'Growth' cluster, the 'aging' trees, showed net productivity rates that decayed exponentially over time (FIG. 2E). Half-lives of net productivity rates for all 28 single-carboxysome trees in the 'aging' cluster were calculated (FIG. 2F). While it is unclear why a third of single-carboxysome trees undergo this exponential decrease in activity, the half lives are longer than the average WT doubling time (3.27 hours), indicating that even aging carboxysomes can contribute to cell growth for multiple generations.

Figure 2:
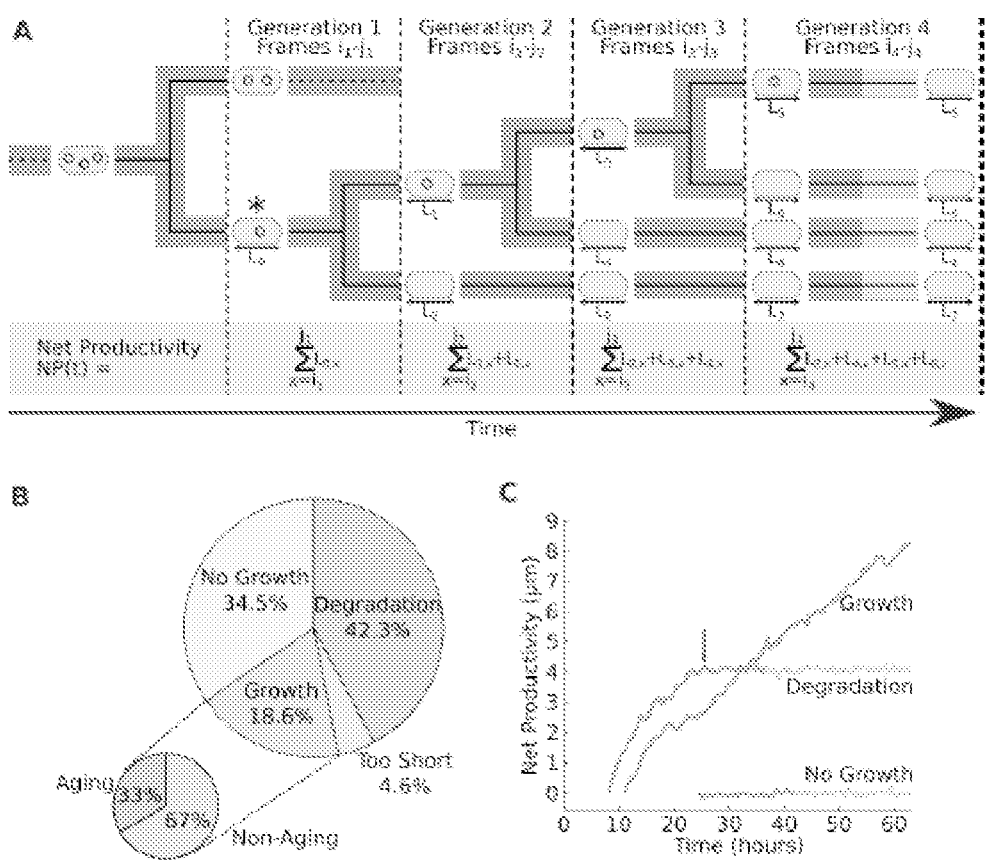
FIG. 2 is a set of illustrations and graphs depicting population-wide classification and activity dynamics of individual carboxysomes. (A) Diagram of a $\Delta ccm^+$ family tree. The single-carboxysome tree starts at the cell indicated with an asterisk. Net productivity is calculated for each frame of the single-carboxysome tree. Cells containing 2+, 1, or 0 carboxysomes, respectively, are shown in the context of the tree. (B) Breakdown of 452 single-carboxysome trees into clusters. The 'Growth' cluster was further split into 'aging' and 'non-aging'. (C) Netproductivity traces for single-carboxysome trees in the 'No growth', 'Growth', and 'Degradation' clusters. The arrow points to the frame in the 'Degradation' cluster trace that separates its 'growth' and 'no growth' phases. (D-E) Net productivity (top) and cell lengths (bottom) for an ultra-productive, 'non-aging' single-carboxysome tree (D), and an 'aging' single-carboxysome tree (E). The cell lengths correspond only to the lineage containing the carboxysome. The dotted line indicates the first frame of the single-carboxysome tree. Linear (D) and exponential decay (E) fits for net productivity. (F) Histogram of net productivity half lives for all 'aging' trees. mean=20.6 hours; standard deviation=±15.1 hours; median=16.8 hours. (G) Net productivity rates for cells in the 'Growth' cluster, 'No Growth' cluster, and the 'growth' and 'no growth' phases of cells in the 'Degradation' cluster.

In the 'Degradation' cluster, a sudden halt in the net productivity rate was observed, resulting in two distinct growth phases (FIG. 2C) denoted as the 'growth' phase and the 'no growth' phase, as net productivity rates for each of these phases independently resemble that of the 'Growth' cluster and 'No growth' cluster, respectively (FIG. 2G).

Figure 3:
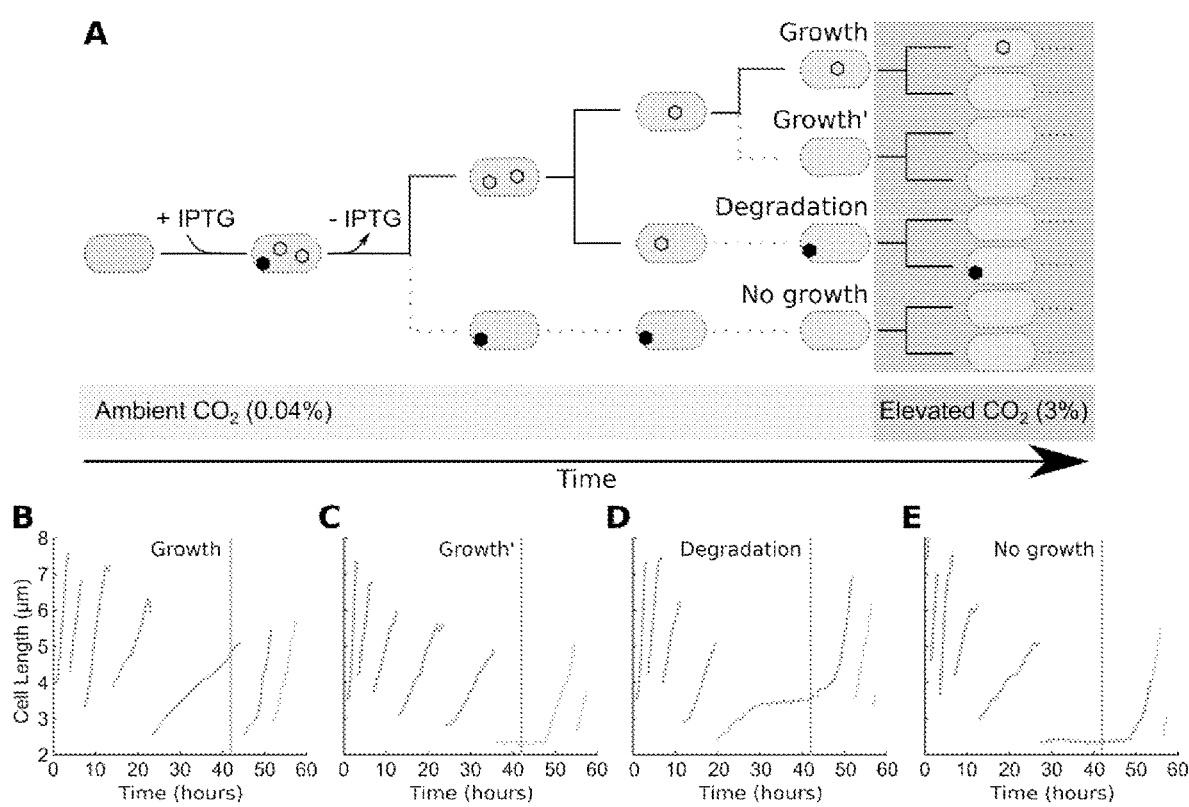
FIG. 3 is an of illustration and graph depicting that the loss of carboxysome-associated $CO_2$ fixation is the direct cause of growth arrest. (A) Diagram of $CO_2$ rescue after IPTG removal. Cyan carboxysomes located in the cytoplasm are functional, while black carboxysomes located at a cell pole are non-functional. Dashed lines indicate that a cell is not growing. The cluster of the single-carboxysome tree of each cell present during the $CO_2$ increase is indicated above the cell. The cell labeled 'Growth' belongs to the 'Growth' cluster, but did not inherit that single-carboxysome tree's carboxysome. (B-E) Cell lengths over time for a lineage in the 'Growth' cluster that contains (B) or does not contain (C) that single-carboxysome tree's carboxysome during the CO2 increase. Cell lengths over time for a lineage in the 'Degradation' cluster (D) and the 'No growth' cluster during the CO2 increase (E). Cell length traces indicate that 2+, 1, or 0 carboxysomes, respectively, are present at that time in the lineage. Vertical lines indicate the time (42 hours) at which the $CO_2$ concentration was increased.

To confirm that the sudden halt in cell growth observed in the 'Degradation' cluster is caused by loss of carboxysome functionality as opposed to a sudden cell death event, an identical IPTG-washout experiment was performed, but this time the $CO_2$ concentration was increased from ambient (0.04%) to elevated (3%) 42 hours after IPTG washout (FIG. 3A). Shortly after increasing the $CO_2$ concentration, growth of cells from the 'Growth' (FIGS. 3B and 3C), 'Degradation' (FIG. 3D) and 'No growth' (FIG. 3E) clusters were restored to WT levels. The fact that cells with either no carboxysomes or a non-functional carboxysome were capable of further growth and division after the $CO_2$ concentration increase suggests that cells enter a recoverable, quiescent-like state upon carboxysome loss and, importantly, implies causation between the sudden loss of carboxysome-associated $CO_2$ fixation and arrested cell growth.

Figure 4:
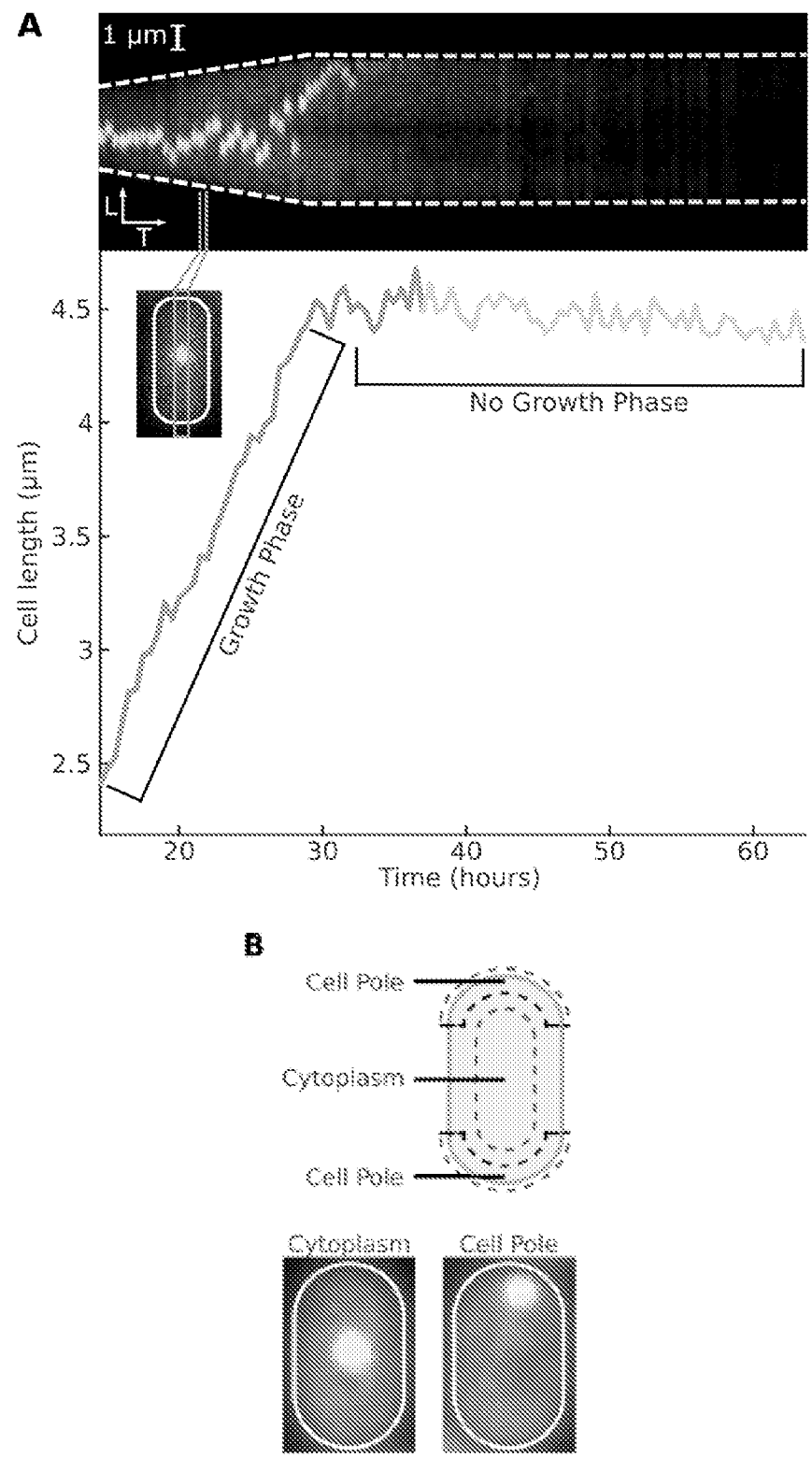
FIG. 4 is a set of illustrations, images and graphs depicting rubisco changes localization upon carboxysome inactivation. (A) Kymogram (top) with corresponding trace of cell length over time (bottom); dark gray and light gray lines indicate 1 or 0 carboxysomes in the cell, respectively. Inset picture indicates slice of cell shown for each time point in kymogram. Only the GFP channel (foci) is shown. (B) Diagram (top) and examples (bottom) of carboxysomes localized to either the cytoplasm or a cell pole. (C) Localization of carboxysomes from different clusters. (n=12, 'Growth' cluster; n=22, 'No growth' cluster; n=31, 'Degradation' cluster). (D) Cell length over time for a cell that starts with two carboxysomes, and ends with one. Dashed lines indicate predicted growth had the carboxysome not degraded (steep dashed line), or if the cell only had one carboxysome to start with (shallow dashed line). (E) Model of carboxysome lifecycle, including carboxysome formation (1), followed by functional carboxysomes supporting many generations of cell growth (2), shell breakage (3), and re-recruitment of Rubisco to a cell pole (4).

Loss of carboxysome activity in the 'Degradation' cluster was generally followed by a change in localization of the GFP punctum from the cytoplasm to a pole of the cell before disappearing completely (FIGS. 4A and 4B), highly suggestive of a carboxysome shell breakage event. Shell breakage would result in the rapid diffusion of $CO_2$ into the cytoplasm and abolishment of the CCM, explaining the immediate arrest in cell growth. Rubisco's change in localization further indicates that the carboxysome lumen is no longer distinct from the cytoplasm, as exposed Rubisco is free to be recruited to a cell pole, where procarboxysomes (carboxysome precursors) are formed. RbcL-GFP puncta were found to change localization from the cytoplasm to a cell pole in 84% of cells in the 'Degradation' cluster (FIG. 4C). For comparison, a similar percentage of cells in the 'No growth' cluster contained RbcL-GFP puncta at a cell pole, while 100% of cells in the 'Growth' cluster contained carboxysomes localized to the cytoplasm (FIG. 4C).

While a subtle phenotype, it was possible to detect carboxysome degradation events in cells with two carboxysomes, as seen by a sudden decrease in growth rate followed by loss of one carboxysome (FIG. 4D). In this example, a functional CCM and expected growth rate is still maintained following carboxysome degradation, due to the presence of another functional carboxysome. This demonstrates that cells are able to distinguish between functional and non-functional carboxysomes and specifically target inactive carboxysomes for degradation while leaving functional carboxysomes intact.

This study shows the continuation of the carboxysome lifecycle post-biogenesis and characterizes the population-level heterogeneity and activity dynamics of individual carboxysomes during $CO_2$-fixation. A small percentage (5%) of carboxysome in the 'Growth' cluster are considered ultra-productive, capable of supporting over 10 μm (~0.2 μm/hour), or ~5+ generations, of cell growth on their own, and should inspire future efforts aimed at maximizing carbon fixation. The results also reveal that inactive carboxysomes are degraded, ending their lifecycle (FIG. 4E), and suggest that shell breakage is the dominant mechanism of carboxysome activity loss. Engineering efforts aimed at increasing carboxysome-catalyzed carbon fixation should therefore focus on improving in vivo stability of the carboxysome shell in addition to improving Rubisco catalysis. A similar degradation mechanism may also apply to other related BMCs, such as the Eut and Pdu microcompartments. More broadly, shown herein is the first example of measuring the long-term activity and spatiotemporal dynamics of single macromolecular enzyme complexes in vivo. This technique is well suited to assess functionality and stability of diverse BMCs, including those that increase pathogenicity in the human gut, in addition to other organelles and macromolecules with measurable activity.

Materials and Methods:

Strain Cultivation

*Synechococcus* sp. PCC 7002 strains were cultivated in AL-41L4 Environmental Chambers (Percival Scientific, Perry, IA) at 37° C. under constant illumination (~150 μmol photons m$^{-2}$ s$^{-1}$) by cool white fluorescent lamps, in either ambient (air; 0.04%) or elevated (3%) $CO_2$ conditions. Cultures were grown in 25 mL A$^+$ media (20) in orbital shaking baffled flasks (125 mL) contained with foam stoppers (Jaece identi-plug), or on pH 8.2 A$^+$ media solidified with Bacto Agar (1%; w/v). For growth on plates in elevated $CO_2$, pH 11 A$^+$ plates were used instead. Antibiotics were added for routine growth of strains (kanamycin, 100 μg/mL; gentamycin, 30 μg/mL; spectinomycin, 100 μg/mL). Induction of the lac-controlled ccm operon was performed with 1 mM IPTG.

Plasmid and Strain Construction

All plasmids and strains used in this work are described in Tables 1 and 2. Plasmids were created through Gibson assembly of plasmid backbones (pUC19 or pALM179) and PCR amplified inserts, generated using Phusion polymerase (Thermo Scientific). Cyanobacterial strains were generated by transforming cells in exponential/early linear growth phase with 0.5 ng/mL-2 μg/mL of plasmid DNA, containing the insert of interest flanked by 500 bp homology arms for recombination into a specified genomic locus. After incubation at 30-37° C. in constant illumination (50-150 μmols photons m$^{-2}$ s$^{-1}$) for 24 hours, transformed cells were selected for with appropriate antibiotic either on plates in ambient $CO_2$, or in liquid A$^+$ in elevated $CO_2$, for non-HCR strains and HCR strains, respectively. From plates, individual colonies were patched onto new plates and tested for segregation. For liquid transformations, antibiotic concentration was slowly increased to up to 2× the standard concentration over the course of a couple days. The Δccm$^+$ strain was first passaged 16× in ambient $CO_2$ with 5 mM IPTG to ensure complete segregation and wild-type growth kinetics prior to experimentation. Upon segregation of the culture, cells were transferred to a pH 11 A$^+$ plate. Confirmation of segregation was confirmed by PCR, using primers specific for either the insert, or the WT genome (FIG. 5). Presence of the insert-specific PCR product and absence of the WT-specific PCR product was used as an indicator of full segregation. All primers are listed in Table S3.

Spot Plating

Indicated strains in FIG. 5C were grown in 6 well plates in ambient $CO_2$ (WT, RbcL-GFP, Δccm$^+$ with 1 mM IPTG) or elevated $CO_2$ (Accra). Cells were diluted to 0.05 $OD_{730\ nm}$ and serially diluted 3 times. 7 μL of each dilution was then spotted on 1% agar A$^+$ plates (pH 8.2 in ambient $CO_2$, pH 11 in elevated $CO_2$) and allowed to dry (5-10 mins) before incubation at standard conditions noted above. When colonies appeared, spot plates were back-lit on a Kaiser eVision light plate and imaged with a Nikon D7200 digital single-lens reflex (DSLR) camera.

Quantitative Microscopy

Fluorescence images were taken using a customized Nikon TiE inverted wide-field microscope with a Near-IR-based Perfect Focus system. Temperature and $CO_2$ concentrations were controlled with a Lexan environmental chamber, and growth light was controlled via a transilluminating red LED light source (Lida Light Engine, Lumincor, Beaverton, OR). A high-speed light source with custom filter sets was used for imaging (Spectra X Light Engine, Lumencor, Beverton, OR), along with a hardware-triggered and synchronized shutter for control of imaging and growth light. NIS Elements software with Jobs acquisition upgrade was used to control the microscope. Image acquisition was performed using an ORCA Flash4.0 V2+ Digital sCMOS camera (Hamamatsu) with a Nikon CF160 Plan Apochromat Lambda 100× oil immersion objective (1.45 N.A.).

For long-term time-lapse microscopy, cells in exponential or early linear phase were diluted to 0.04-0.07 $OD_{730\ nm}$, and 2 μL was spotted onto a 1% agarose A$^+$ pad that was pre-incubated at 37° C. for 1 hour. Cells were dried onto the pad and inverted onto a 35 mm glass bottom imaging dish (Ibidi), which was then wrapped in parafilm to keep the pad from drying out. No antibiotics were included on the agarose pad, but 1 mM IPTG was added when indicated. Cells were acclimated to microscope growth conditions (37° C. and 150 μmol photons m$^{-2}$ s$^{-1}$ 640 nm light) for 30 minutes before acquisition of images. Images were taken every 30 minutes using a 470 nm and 640 nm LED light source (Spectra X), and emission wavelengths were collected using standard YFP and Cy5 filters. Cells were constantly illuminated with red light except during fluorescent imaging.

Image Processing and Analysis

Cell Segmentation. Cell segmentation was performed using MATLAB version R2017b. To segment (identify) individual cells, we also captured images in brightfield, with the focal plane offset by 2 μm. From initial testing, this offset produced the most reliable segmentation results. To remove uneven background shading, the brightfield offset image was first morphologically opened using a 30-pixel disk-shaped structuring element to obtain the background. This image was then subtracted from the original image. A gaussian filter with a standard deviation of two was then used to remove noise. Note that these images were only used for cell segmentation—reported data was measured from the original images.

Cells were then identified by applying an intensity threshold. To obtain this threshold, the intensity histogram of the background was fit to a Gaussian curve. The mean of the Gaussian plus 4-5.5 times its standard deviation was then used as the threshold to create an initial mask. This initial mask often contained touching cells. To separate these cells, the watershed algorithm was used to create the final mask. Manual mask correction was then performed to correct for mistakes prior to data analysis.

Linking Data to Form Tracks. After segmenting each frame, the data was linked to create tracks of time series data for each individual cell, or object. A version of Jaqaman's tracking algorithm (21) was used to link data from a single object between frames, followed by computation of a cost matrix. Data for each object was then assigned between frames in a manner that minimized the total cost using the Jonker-Volgenant algorithm, thus linking cell tracks.

We defined a cost function as the inverse of the ratio of the number of intersecting pixels over the total number of pixels between objects in consecutive frames. The inverse was used as the Jonker-Volgenant algorithm minimizes total cost. If required, before calculating the cost matrix, image registration was performed to correct for drifts in x and y dimensions that sometimes occurred during time-lapse experiments. After registration, the cost matrix was created by calculating costs for each object in a given frame with each object in the next frame. As PCC 7002 cells are non-motile, a maximum linking distance was specified to avoid linking objects over physically impossible distances. Objects between frames that were separated by a distance larger than this maximum linking distance were assigned a cost of infinity. After computing all costs and assignments, some objects were left unassigned (e.g. if they were too far apart from other unlinked cells). In these instances, we checked for cell division by calculating the overlapping cost function between the unassigned object with all objects from the previous frame. If the cost fell between a set value (1 and 8), then cell division occurred and two daughter tracks were created.

Counting Carboxysomes. Puncta in the GFP channel, corresponding to labeled carboxysomes, were identified by computing the difference of Gaussians with standard deviations of 1.16 and 1.64 pixels. To eliminate invalid spots, only puncta brighter than 1.5 times the background were kept.

After raw carboxysome counts were calculated for each frame of every cell track for the $\Delta ccm^+$ strain after IPTG removal in ambient $CO_2$, counts were corrected to increase accuracy. Raw spot counts often fluctuated slightly due to carboxysomes drifting behind one another, or drifting slightly out of focus. Carboxysome counts were corrected, or smoothed, based on the assumption that carboxysome counts cannot increase over time within a cell track due to an inability to create new carboxysomes, and the following rules. If a cell is in the first generation, set the carboxysome count of every frame to the maximum raw carboxysome count for that cell trace. If the number of carboxysomes in the first frame of a daughter cell was larger than the carboxysome count in the final frame of its mother's cell trace, then the carboxysome counts for the first two frames of the daughter track were set to the carboxysome count of the final frame of the mother track. If the carboxysome count of a given frame is greater than the previous frame, it is set to the count of the previous frame to eliminate counting of spurious spots. If the carboxysome count of a given frame is less than the count of the previous frame and the carboxysome count of the next frame, then it is set to the carboxysome count of the previous frame to correct for spurious carboxysome disappearances. If the three frames after the current frame all have higher counts than the current frame, they are assumed to be real counts. In this case, all previous frames of the cell trace are set to the nearest integer of the average of the three frames, thus correcting the problem of a carboxysome artificially disappearing for more than one frame in a row. The reappearance of the carboxysome for three consecutive frames was considered an indication that the carboxysome was present throughout the trace, as three consecutive spurious carboxysome counts were extremely rare. Finally, carboxysome counts were not allowed to decrease in the final frame of the cell trace.

Manually correcting spot counts for 82 cell traces, consisting of 3961 individual frames, showed that corrected spot counts were more accurate than raw spot counts. Raw spot counts agreed with the manually corrected spot counts 87.4% of the time, whereas the corrected spot counts agreed with the manually corrected spot counts 91.1% of the time. Many of the disagreements in the corrected spot counts come from the first ten hours of the video, where it is most difficult to resolve 4+ carboxysomes in a single cell. As analysis focuses mostly on cells with a single carboxysome, these inaccuracies have a minimal negative impact. The rest of the disagreements arise due to slight variations in determining the precise frame in which a carboxysome degradation event occurred, as GFP puncta gradually disappeared over time during carboxysome degradation events. Generally, the MATLAB script lost track of a carboxysome before the human eye lost track of it. As the precise timing of the complete disappearance of a GFP punctum was unimportant in the analysis, the functional accuracy of carboxysome count correcting was ~99%.

Growth rate. The growth rate of each cell track was calculated by fitting the natural log of the cell length over time to a linear polynomial:

$$\ln(L(t)) = \alpha t + \ln(L_b)$$

where $L(t)$ is the length of the cell at time t, a is the growth rate, and $L_b$ is the length at birth. If a $\Delta ccm^+$ cell contained a carboxysome degradation event that split its growth into a 'growth' and 'no growth' phase, only the 'growth' phase was used to calculate the growth rate. It should be noted that exponential growth may not necessarily be the most accurate way to calculate growth rates of the $\Delta ccm^+$ population after IPTG washout in ambient $CO_2$, but this analysis was used in FIGS. 1E, 1F, and S3A-S3D for direct comparison with growth rates of the WT population, which does grow exponentially.

Single-carboxysome trees and net productivities. Single-carboxysome trees were defined as a sub-tree in a $\Delta ccm^+$ family tree that only contains one carboxysome. Net productivity of the tree was calculated at each frame by adding the lengths of all cells in the tree at that time point. The length of the cell at the first frame of the single-carboxysome tree was subtracted at each time point to normalize for differences in the starting length of each tree. All biomass generated by this carboxysome before the start of the single-carboxysome tree (i.e. when it was in other cells from previous generations with more carboxysomes) is not taken into account in the net productivity calculation. For aging trees, net productivity was fit to the following exponential decay function:

$$P(t) = A*(1-e^{-t/k})+b$$

where P(t) is net productivity at time t, A is the maximum net productivity, k is the time constant, and b is the Y offset. The half life of net productivity was then calculated by multiplying ln(2) by the time constant k.

All single-carboxysomes trees were manually clustered into the 'Growth', 'No growth', and 'Degradation' clusters based on their shape. If the carboxysome lasted less than 13 hours in the single-carboxysome tree, it was instead clustered into the 'Too short' cluster and ignored in all further analysis. Net productivity rates were calculated as the slope of the line of best fit to the data. For single-carboxysome trees in the 'Degradation' cluster, the 'growth' phase and the 'no growth' phase were separated to calculate a net productivity rate for each. For aging single-carboxysome trees, the initial ten frames were used to estimate their net productivity rates in FIG. 2G.

In FIG. 4C, the location of carboxysomes in each cluster were recorded manually. While the carboxysome position at each frame was computationally recorded, the GFP puncta often stopped being tracked in situ before it migrated to a cell pole, even though it was clearly still visible by eye.

Statistics

No statistical methods were used to pre-determine sample size. A one-way ANOVA with Tukey-Kramer multiple comparison test was used in FIG. 1E. F-value, 646.46; Total degrees of freedom, 1368.

REFERENCES (PART 1)

1. S. D. Axen, O. Erbilgin, C. A. Kerfeld, A taxonomy of bacterial microcompartment loci constructed by a novel scoring method. *PLoS Comput. Biol.* 10, e1003898 (2014).
2. B. D. Rae, B. M. Long, M. R. Badger, G. D. Price, Functions, Compositions, and Evolution of the Two Types of Carboxysomes: Polyhedral Microcompartments That Facilitate CO2 Fixation in Cyanobacteria and Some Proteobacteria. *Microbiol. Mol. Biol. Rev.* 77, 357-379 (2013).

3. A. Turmo, C. R. Gonzalez-Esquer, C. A. Kerfeld, Carboxysomes: metabolic modules for CO2 fixation. *FEMS Microbiol. Lett.* 364 (2017), doi:10.1093/femsle/fnx176.
4. G. D. Price, M. R. Badger, Evidence for the role of carboxysomes in the cyanobacterial $CO_2$-concentrating mechanism. *Can. J. Bot.* 69, 963-973 (1991).
5. G. D. Price, M. R. Badger, F. J. Woodger, B. M. Long, Advances in understanding the cyanobacterial CO2-concentrating-mechanism (CCM): functional components, Ci transporters, diversity, genetic regulation and prospects for engineering into plants. *J. Exp. Bot.* 59, 1441-1461 (2008).
6. M. Dworkin, S. Falkow, E. Rosenberg, K.-H. Schleifer, E. Stackebrandt, Eds., *The Prokaryotes* (Springer New York, New York, NY, 2006; http://link.springer.com/10.1007/0-387-30742-7).
7. C. R. Gonzalez-Esquer, S. E. Newnham, C. A. Kerfeld, Bacterial microcompartments as metabolic modules for plant synthetic biology. *Plant J.* 87, 66-75 (2016).
8. B. M. Long et al., Carboxysome encapsulation of the CO2-fixing enzyme Rubisco in tobacco chloroplasts. *Nat. Commun.* 9, 3570 (2018).
9. J. C. Cameron, S. C. Wilson, S. L. Bernstein, C. A. Kerfeld, Biogenesis of a Bacterial Organelle: The Carboxysome Assembly Pathway. *Cell.* 155, 1131-1140 (2013).
10. H. Wang et al., Rubisco condensate formation by CcmM in β-carboxysome biogenesis. *Nature.* 566, 131-135 (2019).
11. H. C. Bernstein et al., Unlocking the Constraints of Cyanobacterial Productivity: Acclimations Enabling Ultrafast Growth. *M Bio.* 7, e00949-16 (2016).
12. A. M. Ruffing, T. J. Jensen, L. M. Strickland, Genetic tools for advancement of *Synechococcus* sp. PCC 7002 as a cyanobacterial chassis. *Microb. Cell Fact.* 15, (2016).
13. G. C. Gordon et al., CRISPR interference as a titratable, trans-acting regulatory tool for metabolic engineering in the cyanobacterium *Synechococcus* sp. strain PCC 7002. *Metab. Eng.* 38, 170-179 (2016).
14. A. L. Markley, M. B. Begemann, R. E. Clarke, G. C. Gordon, B. F. Pfleger, Synthetic Biology Toolbox for Controlling Gene Expression in the Cyanobacterium *Synechococcus* sp. strain PCC 7002. *ACS Synth. Biol.* 4, 595-603 (2015).
15. J. S. MacCready et al., Protein gradients on the nucleoid position the carbon-fixing organelles of cyanobacteria. *Elife.* 7 (2018), doi:10.7554/eLife.39723.
16. D. F. Savage, B. Afonso, A. H. Chen, P. A. Silver, Spatially ordered dynamics of the bacterial carbon fixation machinery. *Science.* 327, 1258-61 (2010).
17. M. Campos et al., A Constant Size Extension Drives Bacterial Cell Size Homeostasis. *Cell.* 159, 1433-1446 (2014).
18. C. Chowdhury, S. Sinha, S. Chun, T. O. Yeates, T. A. Bobik, Diverse bacterial microcompartment organelles. *Microbiol. Mol. Biol. Rev.* 78, 438-68 (2014).
19. C. M. Jakobson, D. Tullman-Ercek, Dumpster Diving in the Gut: Bacterial Microcompartments as Part of a Host-Associated Lifestyle. *PLoS Pathog.* 12, e1005558 (2016).
20. S. E. Stevens, C. O. P. Patterson, J. Myers, THE PRODUCTION OF HYDROGEN PEROXIDE BY BLUE-GREEN ALGAE: A SURVEY. *J. Phycol.* 9, 427-430 (1973).
21. K. Jaqaman et al., Robust single-particle tracking in live-cell time-lapse sequences. *Nat. Methods.* 5, 695-702 (2008).
22. R. Jonker, A. Volgenant, A shortest augmenting path algorithm for dense and sparse linear assignment problems. *Computing.* 38, 325-340 (1987).
23. D. G. Lowe, "Object Recognition from Local Scale-Invariant Features" (1999), (available at https://www.c-s.ubc.ca/~lowe/papers/iccv99.pdf).

Example 2—Multi-Generational Analysis and Manipulation of Chromosomes in a Polyploid Cyanobacterium Faithful replication and inheritance of genetic material is essential for life. Models of microbial DNA replication and inheritance are based on data from monoploid bacteria containing a single chromosome. However, emerging research on polyploid bacteria calls into question whether the established mechanisms of chromosome maintenance are conserved across the bacterial kingdom. We utilized time-lapse microscopy and computational image-analysis in conjunction with inducible CRISPR-interference to simultaneously modulate gene expression, track labeled chromosomes, and monitor physiology in a polyploid cyanobacterium for multiple generations at single cell resolution. We found that the chromosome number to cell size ratio was not impacted by manipulating cell growth, division, or septum placement. Surprisingly, diluting chromosomes over time resulted functional cells for multiple generations. We also demonstrate that rapid depletion of chromosomes vis mis-segregation also results in functional cells that lack chromosomes. These results indicate that polyploid cells may be especially resistant to disruptions in chromosome content.

Strict mechanisms have been described throughout all kingdoms of life to ensure that genetic material is reliably inherited in future generations (O'Donnell, Langston, & Stillman, 2013). These mechanisms include regulating how and when DNA is replicated and the process of symmetric DNA segregation to progeny. In bacterial cells, the vast majority of the work describing DNA replication and segregation machinery has occurred in a small number of well-studied model systems (Reyes-Lamothe, Nicolas, & Sherratt, 2012). However, model systems represent only a tiny fraction of microbial diversity, and it is now evident that this diversity plays a pivotal role in the macroscale world (Liu & Deutschbauer, 2018; Locey & Lennon, 2016). To expand mechanistic and functional understanding of these critical processes, chromosome dynamics was investigated in the cyanobacterium *Synechococcus* sp. PCC 7002 (hereafter "PCC 7002"), a polyploid photosynthetic bacterium.

Polyploidy, the presence of multiple, identical chromosome copies, is not often associated with bacteria. However, both industrially and medically relevant bacteria, as well as bacterially-derived organelles, such as mitochondria and chloroplasts, are polyploid (Clay Montier, Deng, & Bai, 2009; Sakamoto & Takami, 2018; Soppa, 2017). Polyploidy is distinct from mero-oligoploidy, which occurs in rapidly growing monoploid bacteria, such as *E. coli*, when multiple rounds of DNA replication initiation begin prior to termination (Cooper & Helmstetter, 1968). In contrast, polyploid bacteria obligately contain multiple complete copies of their chromosome. DNA replication in polyploid bacterial cells appears to be stochastic and is not correlated with cell division (Chen, Afonso, Silver, & Savage, 2012; Jain, Vijayan, & O'Shea, 2012). However, the mechanisms controlling DNA copy number and segregation are not well defined, nor is it well understood how ploidy levels in one generation affect future generations.

The physiological consequences of polyploidy in bacteria have not been thoroughly investigated. Increasing plasmid copy number in E. coli results in increased gene expression (Segall-Shapiro, Sontag, & Voigt, 2018). However, the effect of increasing chromosome copy number in bacterial cells is less clear, with recent evidence indicating that growth rate and limited translational machinery are the major regulators of constitutive gene expression (Bryant, Sellars, Busby, & Lee, 2014; Chandler & Pritchard, 1975). Additional consequences of polyploidy may include increased adaptability in extreme environments as has been shown for polyploid varieties of both plants and yeast (Selmecki et al., 2015; Van de Peer, Mizrachi, & Marchal, 2017), protection from DNA insults (Ohbayashi et al., 2019), or as nutrient storage (Zerulla et al., 2014). Increasing the understanding of both the mechanisms and consequences of polyploidy in bacteria is essential to gaining a broader perspective on the microbial world and its interactions with eukaryotes and the environment.

To address these gaps in knowledge, fluorescently labeled chromosomes were imaged in actively growing cells for multiple generations, while simultaneously collecting quantitative information on cellular physiology, including growth rate and gene expression data. Using this method, the effect of growth rate on chromosome copy number and protein expression in PCC 7002 was defined. Inducible CRISPR-interference was also used to determine the consequences of inhibiting essential cell functions, such as cell division and DNA replication, on chromosome homeostasis. Although polyploid cells are able to maintain a consistent chromosome to cell size ratio during changes in growth rate and manipulations of cell division, PCC 7002 is found to be surprisingly resilient to chromosome depletion or loss, indicating that they may be able to survive in conditions that result in decreased or damaged chromosomes.

Materials and Methods

Experimental Model and Subject Details

All Strains of Synechococcus sp. PCC 7002 were cultivated in A$^+$ media (Stevens, Patterson, & Myers, 1973) in an AL-41L4 Environmental Chamber (Percival Scientific, Perry, IA) maintained at 37° C. with atmospheric $CO_2$ conditions, with continuous illumination (~150 μmol photons $m^{-2}$ $s^{-1}$) provided by cool white fluorescent lamps. All strains were grown in 25 ml liquid cultures in baffled flasks (125 ml) contained with a foam stopper (Jaece identi-plug) and on an orbital shaker (200 rpm), or on medium solidified with Bacto Agar (1%; w/v). For maintenance, all 240x tetO-array:TetR-sfGFP strains were grown with 0.5 μg/mL anhydrotetracycline (aTC). Antibiotics were provided to solid medium for routine maintenance of mutants when necessary (km, 30 μg/ml; sp, 25 μg/ml; gm, 15 μg/ml).

Method Details

Strain and plasmid construction: All oligos, sgRNAs, plasmids, and strains used in this work are described in Tables 5-8. WT PCC 7002 is the background genotype for all strains described. To create strains in Table 8, noted plasmids, or amplicons containing homologous recombination arms and inserts, were transformed into WT or mutant backgrounds, and transformants were selected on the specified antibiotic(s). To transform, ~1 ug of plasmid or amplicon was mixed with day old cells and allowed to incubate for 4-14 hr before plating on 1% Bacto-agar plates with antibiotics. Plates also included 0.5 μg/mL aTC for all 240x tetO-array: TetR-sfGFP strains. Once individual colonies were detectable, they were patched to new plates with single or combined antibiotics and aTC. After ~48 hr of growth patches were checked for segregation and intact tetO arrays. Strains were considered segregated when no WT products could be detected from PCR using primers flanking the insert and/or gene specific primers (Table 5). All CRISPRi strains were freshly transformed for each experiment due to genetic instability of the constructs following repeated passaging. Strains were transformed in the following order: 1) 240x tetO array containing construct, 2) TetR-sfGFP containing construct, and 3) mOrange2, sgRNA, or deletion construct. In this system, the strand specificity of the TetR-sfGFP gene had an effect on tetO array stability, with negative strand constructs being more stable than positive stand constructs.

All plasmids described in Table 7, except KAMc0006, were created using gibson assembly of PCR amplified inserts and backbones from base plasmids described in the STAR Methods Resource Table or the PCC 7002 genome. mOrange2 was subcloned from mOrange2-pBAD, a gift from Michael Davidson, Nathan Shaner, and Roger Tsien (Addgene plasmid #54531). KAMc0006 was created with restriction digest cloning to insert the 240x tetO:GmR array from PRS316-240xtetO into the JCC257 backbone. PRS316-240xtetO was a gift from Narendra Maheshri (Addgene plasmid #44755).

Hoechst Staining: Cells were stained with Hoechst dye at specific growth phases. Cells were briefly centrifuged and resuspended in low salt (10% of normal) A+ media and mixed with 5 μg/mL 33342 Hoechst stain (Fisher, CAS #23491-52-3). Cells were then incubated in the dark for ~35 min before being washed twice in full salt A+ media. Cells were imaged using 395 nm excitation and collected light emitted between 425-477 nm.

Quantitative Real Time PCR (qRT-PCR): To determine average chromosome copy number from bulk culture, we followed the procedure described by Pecoraro et al., (2011) was followed. Briefly, either WT or scJC0147 cells were counted at the noted growth phase and then extracted DNA using phenol:chloroform extraction (Green, Sambrook, & Sambrook, 2012) after initial treatment with 5 mg/mL lysozyme for 1 hr shaking prior to SDS/proteinase K lysis. To create samples for a standard curve, we purified and quantified 1000 bp PCR products amplified from the PCC7002 genome. These fragments were serially diluted to create standards of known concentrations. The ThermoFisher QuantStudio6 platform was used to perform qRT-PCR. Samples were prepared with PerfeCTa SYBR Green SuperMix Reaction Mix (QuantasBio, Catalog #95056-500) and primers that annealed within our 1000 bp standards (Table 5). Samples were run in triplicate to control for pipetting error. The average chromosome copy number was determined by measuring the amount of DNA in each sample and dividing by original cell count. Averages and standard deviations were calculated from 2-3 biological replicates of each strain in each condition.

sgRNA design and CRISPR-interference: sgRNAs described in Table 6 were designed using the CRISPy-web platform (Blin, Pedersen, Weber, & Lee, 2016). sgRNAs were chosen based on guidelines described by Gordon et al., (2016). To create an inducible sgRNA construct that was compatible with our chromosome labeling, the sgRNA was placed downstream of the Isopropyl β-D-thiogalactopyranoside (IPTG) inducible cLac94 promoter (Markley et al., 2015). 5 mM IPTG (Fisher, CAS #367-93-1) was used to induce sgRNA expression. Strains were maintained in the absence of IPTG.

Quantitative Long-term Timelapse microscopy: We used a customized Nikon TiE inverted wide-field microscope setup equipped with a Near-IR-based Perfect Focus system, a custom Lexan environmental enclosure for temperature and $CO_2$ control, an individually controllable RGB LED light source for transillumination (Lida Light Engine, Lumincor, Beaverton, OR), a high-speed light source with customized filter sets for imaging (Spectra X Light Engine, Lumencor, Beverton, OR), and a synchronized and hardware-triggered motorized shutter for light control for all microscopy described. We specifically used 395 nm 470 nm, 555 nm, and 640 nm excitation wavelengths. Emissions were collected using standard BFP, FITC, mOrange2, or Cy5 filters. Images were acquired on an ORCA Flash4.0 V2+ Digital sCMOS camera (Hamamatsu) and a Nikon CFI60 Plan Apochromat Lamda 100× oil immersion objective (1.45 N.A.). NIS Elements Software was used with Jobs acquisition upgrade for image capture. Fiji (Schindelin et al., 2012) was used to crop and reformat images for publication.

For either single frame or time-lapse microscopy, ~2 μL of exponential-phase cells was spotted on A+ media pads (1% agarose w/v) and allowed them to air dry before inverting them on to 35 mm glass bottom dishes (Ibidi). Unless otherwise noted, all long-term imaging of strains with the tetO array was performed with 0.05 μg/mL aTC added to the imaging pad prior to solidification. Additionally, 5 mM IPTG was added to induce sgRNA expression, 1.25 μg/mL rifampicin (Fisher, CAS #13292-46-1) to inhibit transcription, or 3.4 μg/ml chloramphenicol (Fisher, CAS #591-50-4) to inhibit translation in noted experiments. For CRISPRi induction as well as rifampicin and chloramphenicol treatment, imaging pads were placed at 30° C. for ~1 hr before cells were spotted on to pads. Imaging was started ~15 min after spots air dried. For all other imaging, cells were acclimated to imaging conditions (30° C. and noted 640 nm transmitted light intensity) for ~1 hr prior to initial imaging. Images were taken at a 30 min frame rate for all experiments, except those described in FIG. 15A-D, where the frame rate was 10 min. Cells were continuously illuminated with 640 nm transmitted light except during fluorescent imaging.

Image Processing and Analysis: Image processing was carried out using custom MATLAB programs. From initial testing, segmentation was most reliable on brightfield images of the cell, but with the focus offset by 2 μm. In brief, cell identification (segmentation) was performed by thresholding this brightfield offset image. The threshold level was chosen by computing the intensity histogram of the image. Since the images contained both dark background and bright cells, the intensity histogram appeared bimodal, allowing the peak of the background intensity distribution to be identified. A Gaussian model was then fit to this background intensity. The threshold intensity was then chosen to be the mean+F * standard deviation of the fitted Gaussian. The threshold factor, F, was optimized for each set of images, and ranged from 2.0-3.5.

Once the threshold intensity was determined, an initial binary mask was created by setting pixels in the image which were brighter than the threshold to true, and all other pixels to false. This initial mask often contained connected cells that were physically close to each other. Individual cells were then separated using the watershed algorithm. Data from individual cells were then tracked over time using the linear assignment algorithm (Jaqaman et al., 2008). When necessary cell masks were corrected by hand to avoid obvious tracking and/or size errors.

To count chromosomes in the images, sfGFP labeled puncta were identified using the difference of Gaussians method (Lowe, 1999). Here, two Gaussian blur filters were applied to the original image, with standard deviations σ of 1.12 and 1.58 pixels. The difference between the two images was then computed, and puncta were identified by intensity thresholding. Individual puncta were then counted to obtain chromosome numbers in each cell.

Quantification and Statistical Analysis

During growth, the length of cells was assumed to be increasing exponentially. Hence, we obtained a growth rate by fitting the log of cell length over time to the linear function $$\ln(L(t)) = at + \ln(L_b),$$

where L(t) is the length of the cell at time t, a is the growth rate, and $L_b$ is the length at birth. Doubling times were calculated by dividing ln(2) by the growth rate a.

Corrected Chromosome Counting Algorithm: Because chromosome labeling is a dynamic process, an algorithm was developed based on both previous and future chromosome counts to create a more accurate representation of chromosome number during time lapse imaging. The following rules were used to define chromosome number:
1. Chromosome number could not decrease
2. Chromosome number only increased in the nth frame if the chromosome number in the n+1 frame was equal to or greater than the number recorded in the nth frame
3. For the final frame of a cell trace chromosome number only increased if the sum of chromosome counts in the two daughter cells was equal to or greater than the number recorded in the final frame Representations of original and corrected chromosome counts are displayed in FIG. 17.

Data and Statistics: The number of cells analyzed in each experiment is recorded in the figure descriptions. For analyses performed in FIGS. 11, 12, and 13G-H, unless otherwise noted, only cells with traces that both started and ended within the imaging time (i.e. not first or last generation cells) were analyzed. For analyses performed in FIGS. 13D-E and 14 analyses were performed on cells based on generation and with cell traces longer than 3 hrs. For cells with measured growth rates, only those with <0.3 norm of residuals between the data and the model were kept in the analysis. All long-term imaging experiments were performed at least twice to ensure reproducible phenotypes. However, only data from a single long-term imaging experiment is shown with the exception of FIG. 14F-G to ensure that enough cells were analyzed for all generations. Chromosome counts were verified by eye for 50-100 cells for each still or time lapse imaging experiment. For time-lapse experiments, chromosome counts were checked at multiple stages of imaging. Images displayed in figures have been smoothed to reduce background noise. However, all analyses were done on the original images. To normalize for variations in imaging cell intensity, measurements were smoothed over 120 min segments in FIGS. 15B (bottom panel) and D.

For FIGS. 12I-K and P-Q cells were categorized as growing predominantly in HL if they grew for at least 3 hr in HL conditions. Cells were categorized as growing predominantly in LL if they grew for at least 7 hr in LL conditions. To avoid grouping cells that grew in both light conditions cells in either group were analyzed only if they grew for less than 1 hr in the alternative light condition.

All boxplots denote the median (light gray line), the $25^{th}$ and $75^{th}$ quartiles of the data (dark gray boxes), and the most extreme values not considered outliers (whiskers). Whisker values correspond to approximately +/−2.7 σ and represent ~99.3% of the data, assuming normal distribution. For all histogram and single frame data, chromosome counts are only displayed for cells within 3 standard deviations of the mean of the data. To determine if the variation between cell populations was statistically significant, we used the two sample Kolmogorov-Smirnov test. Significance was determined using Bonferroni corrected p-values, which are denoted by *, , * to represent <0.01, 0.001, and 0.0001, respectively.

Chromosome Labeling and Computational Quantification in PCC 7002

Figure 16:
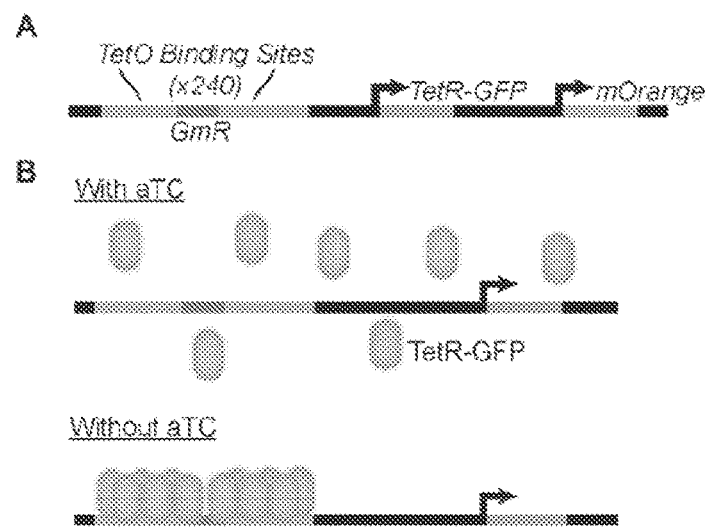
FIG. 16 is a pair of schematics of tetO array:TetR-sfGFP chromosome labeling system. (A) Depiction of mOrange2:: 240x tetO array::TetR-sfGFP genotype. sfGFP=super folder GFP. (B) Schematic of TetR-sfGFP binding to the tetO array with (top) and without (bottom) aTC.

To study polyploidy at the single cell level in PCC 7002, individual chromosomes were fluorescently labeled using a 240x tetO array—TetR-sfGFP (super folder GFP)-based approach adapted from previously described studies in yeast and bacteria (Chen et al., 2012; Jain et al., 2012; Michaelis, Ciosk, & Nasmyth, 1997). Because this system relies on inducible TetR-tetO binding we were able to modulate chromosome labeling with the small molecule anhydrotetracyclene (aTC) (FIG. 16A-B). We also genetically encoded the mOrange2 gene as a tool to study gene expression in these cells.

Figure 10:
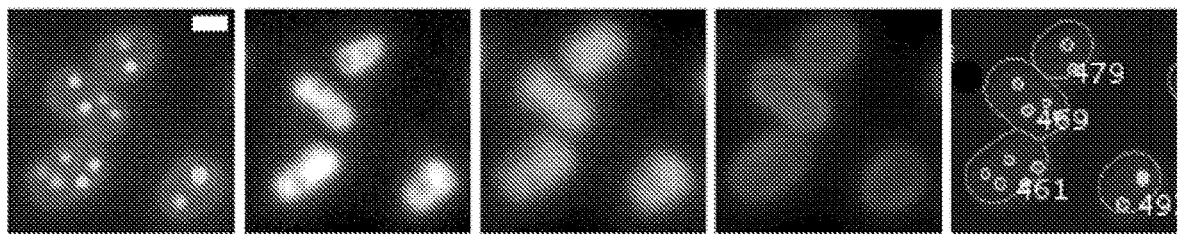
FIG. 10 is a set of images and graphs depicting chromosome labeling in PCC 7002. (A) From L-R: Representative images of sfGFP-labeled chromosomes, Hoechst staining, mOrange2 expression, endogenously fluorescent thylakoid membranes, and cell (magenta outlines) and chromosome (green outlines) masks from a population of mOrange2:: 240x tetO array::TetR-sfGFP cells. (B) The distribution of chromosome counts from the population of cells represented in FIG. 10A. (C)-(E) Length, Hoechst stain intensity, and mean mOrange2 expression (mOrange2 intensity/area), respectively, measured in cells with different chromosome number from the population of cells represented FIG. 10A. N=1933. Boxes represent the 25th-75th percentile of the data, with the median marked in light gray. Whiskers show the distribution of extreme values. (F) Representative images of chromosome labeling in cells from exponential (top panel) and linear (bottom panel) growth phase. (G) Distributions of chromosome numbers in the populations represented in FIG. 10F. $N_{Exp}$=240, $N_{Lin}$=506. (H) Representative images of Hoechst staining in cells from exponential (top panel) or stationary (bottom panel) growth phase. White outline indicates perimeter of cells. (I) Distributions of Hoechst staining divided into 8 groups by intensity values from the populations of cells represented in (H). These groups are not representative of chromosome number. $N_{Exp}$=967, $N_{Stat}$=1089. Scale Bar=1 µM.
Figure 10:
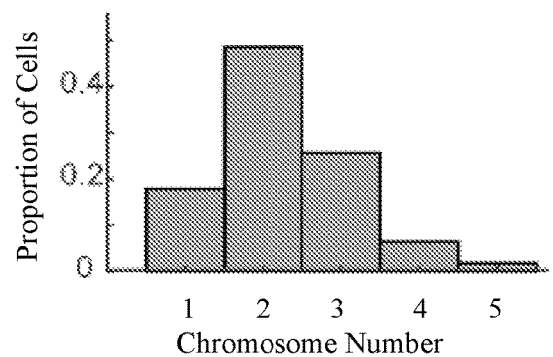
Figure 10:
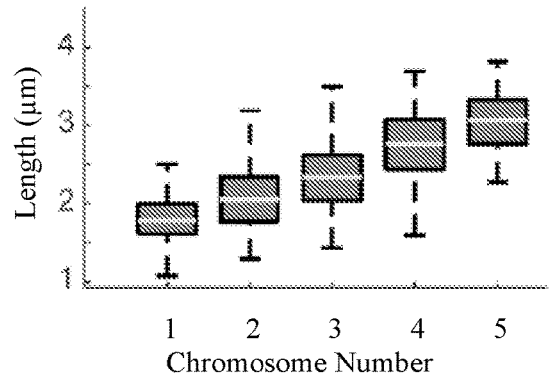
Figure 11:
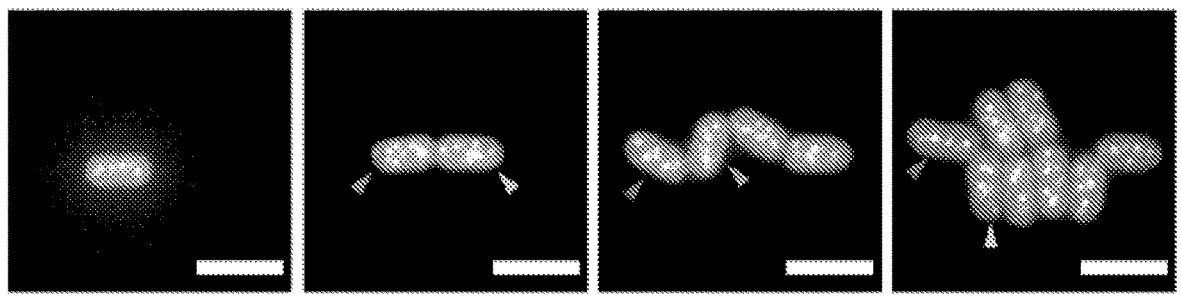
FIG. 11 is a set of images and graphs depicting multi-generational chromosome dynamics in PCC 7002. (A) Time-lapse images of labeled chromosomes from mOrange2::tetO array:: TetR-sfGFP cells grown in 150 µmol photons $m^{-2}$ $s^{-1}$ red light for 18.5 hours (hr). Arrows correspond to the traces in throughout FIG. 2. (B) Chromosome count over time for cells at the 2-cell, 4-cell and 8-cell colony stages. Only two representative traces are displayed for the 4- and 8-cell stages for the sake of clarity. Dotted lines indicate cell division events. (C) Cell length over time for cells at different growth stages of microcolony formation. An exponential model was used for length doubling time calculations, displayed as solid lines. (D-E) Chromosome count to cell area ratio, averaged over cell lifespan (D) and $\Delta$ chromosome count/hour (E) for all cells in the 2-, 4-, and 8-cell microcolony stages. $N_{2\text{-}cell}$=64, $N_{4\text{-}well}$=229, $N_{8\text{-}cell}$=332. (F) Average chromosome number calculated for cells at each microcolony position and stage. (G) Chromosome segregation from mother cells (chromosome count at division on X-axis) to daughter cells (chromosome count at birth on Y-axis). Spot size is proportional to the number of cells. $N_{mother}$=385, $N_{daughter}$=770. (H) mean mOrange2 intensity for cells with different chromosome numbers at the 4-cell microcolony stage. N=2488 single frames. (I) Total mOrange2 intensity measured over time for cells at the 2-, 4-, and 8-cell stages. Scale bar=5 µm.
Figure 11:
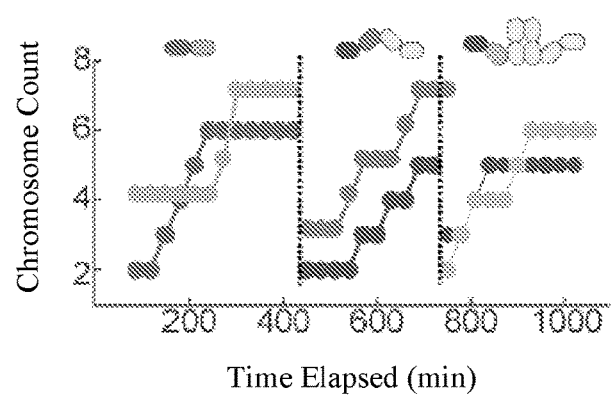
Figure 11:
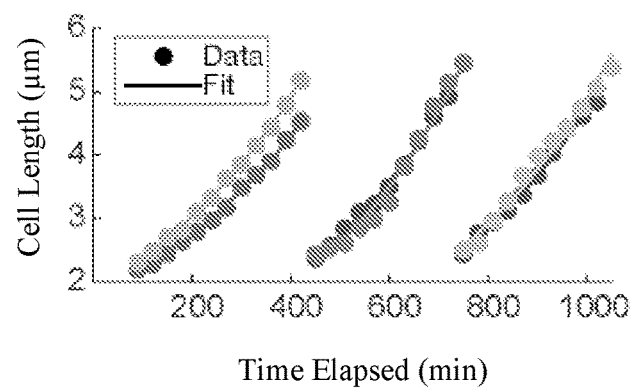
Figure 12:
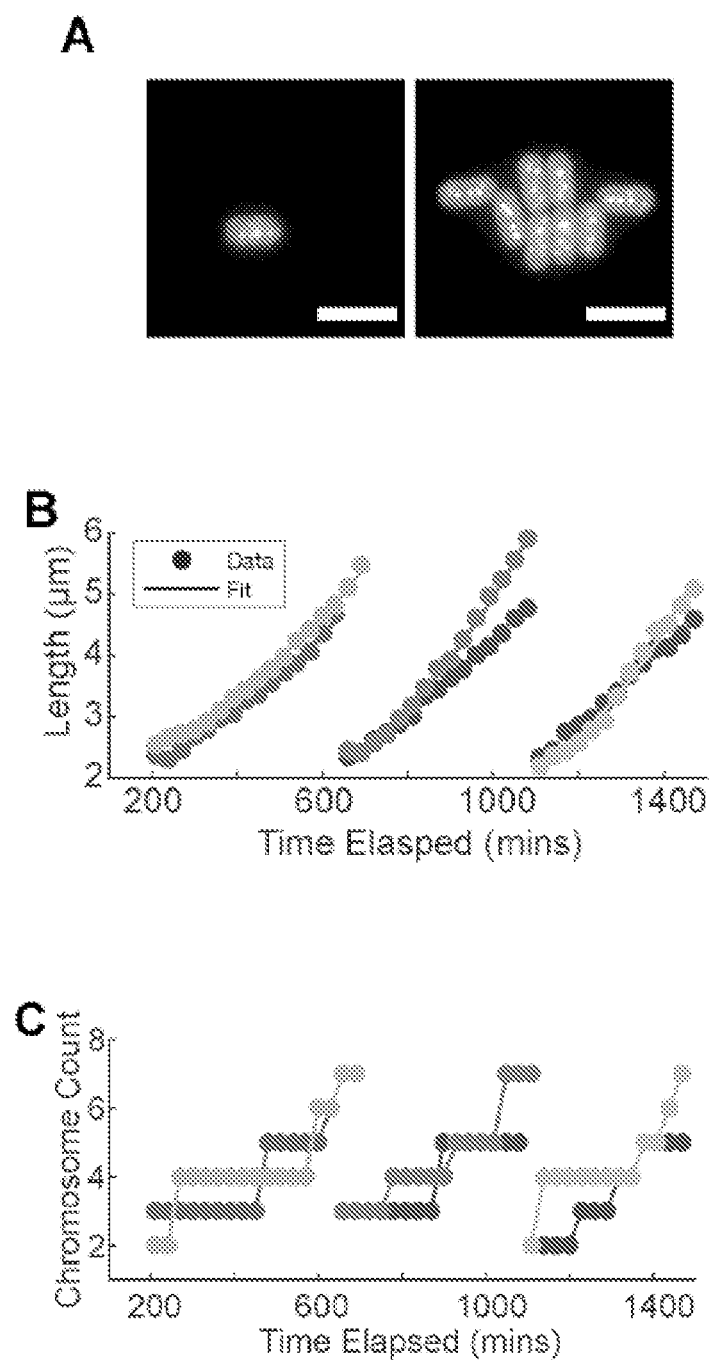
FIG. 12 is a set of images and graphs depicting the effect of growth rate on chromosome dynamics and protein expression and accumulation. (A) Time-lapse images of labeled chromosomes from mOrange2::tetO array::TetR-sfGFP cells grown in 45 µmol photons $m^{-2}$ $s^{-1}$ red light over 27 hr. (B-C) Length and chromosome count, respectively, at different stages of microcolony growth. (D) Chromosome count per area ratio, averaged over the lifespan of cells, grown in HL or LL. (E) mean mOrange2 intensity over time for cells grown in HL (top panel) or LL (bottom panel). (F-G) Cell length doubling time and mOrange2 intensity doubling time, respectively, for cells grown in HL and LL. Data from 4-cell stage displayed. $N_{HL}$=229, $N_{LL}$=216 for FIGS. 3D, F, and G. (H) Time-lapse images of labeled chromosomes in cells grown in HL for 6 hr followed by LL for 12 hr. (I-K) Length doubling time, $\Delta$ chromosome #/hr, and percentage change in mOrange2 intensity, respectively, for cells grown in HL and LL. Percentage change was measured by dividing the difference between mOrange2 intensity in the final and the first frame of a cell trace by the initial intensity, multiplied by 100. $N_{HL}$=98, $N_{LL}$=79. (L-N) Chromosome count, length, and mean mOrange2 intensity, respectively, over time for cells grown in HL (2-cell stage, orange traces) or during the light transition indicated by the arrow and dotted line (4-cell stage, purple traces). (0) Time-lapse images of labeled chromosomes in cells grown in LL for 16 hr followed by HL for 8 hr. (P-R) Length doubling time, Δ chromosome #/hr, and percentage change in mOrange2 intensity, respectively, for cells grown in LL and HL. $N_{LL}$=77, $N_{HL}$=77. (S-U) Chromosome count, length, and mean mOrange2 intensity, respectively, over time for cells grown during the light transition (4-cell stage, purple traces) and in HL (8-cell stage, green traces, only 4 traces shown for clarity). Scale bar=5 μm.

To analyze chromosome numbers in large populations of cells, we developed customized software to identify individual chromosomes, as well as measure gene expression via fluorescence intensity to generate quantitative data. FIG. 10 depicts representative images, from left to right, of chromosome labeling, DNA staining (with Hoechst dye), mOrange2 expression, thylakoid membrane fluorescence, and automated cell and chromosome identification masks from a population of flask grown cells. We observed a broad distribution of chromosome numbers within our population of cells (FIG. 10B). We also observed a strong correlation between cell length and chromosome number, as well as DNA staining intensity as measured by comparing Hoechst staining with chromosome number (FIG. 10C-D), indicating that the system was a reliable tool to measure chromosome content. Regardless of chromosome number, it was observed that mean mOrange2 expression (mOrange2 intensity normalized to cell area) remains consistent in all cells (FIG. 10E). In these experiments, mOrange2 expression was driven by the Pcpt promoter, which is unaffected by changes in light level in PCC 7002 (Markley, Begemann, Clarke, Gordon, & Pfleger, 2015).

To determine whether growth phase has an effect on chromosome number, as observed for other polyploid bacterial strains (Ohbayashi et al., 2019; Soppa, 2017), we grew chromosome labeled cells to either mid-exponential or late-linear phase and imaged cells. Due to the light-dependent autotrophic nature of cyanobacterial cell growth, as cells grow in batch culture they become light-limited due to self-shading. This nutrient limitation results in decreased growth rate following exponential phase, but prior to stationary phase. This phase is termed linear growth (Clark et al., 2018). Cells in exponential phase were both larger in size and had higher average chromosome numbers than cells in linear phase (FIGS. 10 F-G). We also grew Wild Type (WT) cells to either exponential or stationary phase and measured DNA content using Hoechst staining (FIG. 10H). A shift was observed toward increased staining in exponential cells compared to stationary phase cells (FIGS. 10 H-I), indicating that total DNA content decreases in slower growing WT cells, similar to what was observed for chromosome labeled cells. These observations were confirmed using a previously described quantitative-PCR based method (Table 4) (Pecoraro, Zerulla, Lange, & Soppa, 2011). Because of these differences we primarily utilized cells grown to mid-exponential phase for the following experiments.

Chromosome Dynamics are Consistent Over Multiple Generations

Figure 17:
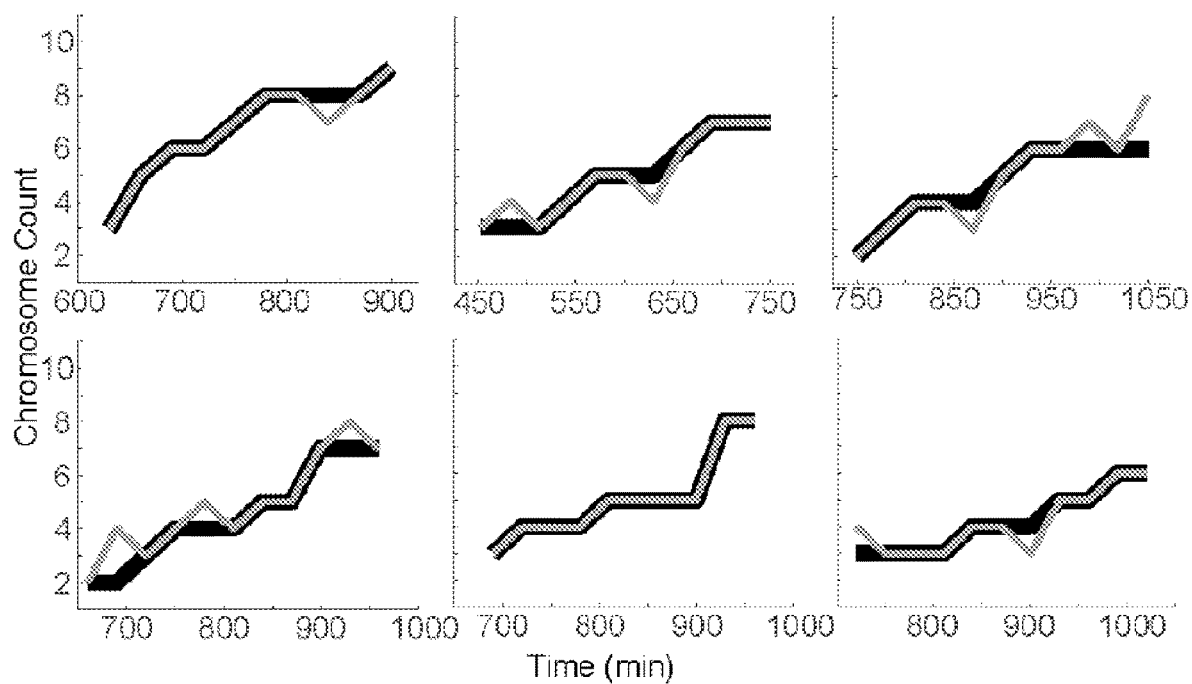
FIG. 17 is a set of graphs depicting representative traces of corrected and raw chromosome counts over time. Raw chromosome counts are traced in gray, corrected chromosome counts are traced in black. The X-axis represents time-elapsed from the first frame of time lapse imaging. See Methods Details for information regarding the chromosome correcting algorithm used.

We captured chromosome dynamics in growing cells by performing time-lapse microscopy of chromosome labeled strains. Unless otherwise noted cells were grown on 1% (w/v) agarose pads made with A+ media under 150 µmol photons $m^{-2}$ $s^{-1}$ of red light (640 nm) as previously described (Moore et al., 2020). Using this method, we were able to image chromosome labeled cells for ~24 hr with a 30 minute (min) frame rate allowing us to track lineages for 3-4 generations (FIG. 11A-B). Cells with labeled chromosomes grew similarly to WT cells as noted by the characteristic microcolony formation of PCC 7002 (Moore et al., 2020). Measured growth rates were also similar in chromosome labeled and WT cells, with median length doubling times of 266 and 245 min, respectively. Because of the dynamic nature of chromosome replication, which includes binding and release of DNA binding proteins, such as TetR, and the physical limitations of resolving diffraction-limited fluorescent foci in the cell, the number of puncta in a single-frame image of a cell may not represent the true number of chromosomes in that cell. To address this challenge, an algorithm was created to predict chromosome number based on previous and future frames for each cell. (FIG. 17 and methods section for details). These corrected values were used for all data analyses.

To quantify chromosome dynamics over we time, we calculated per frame chromosome number using the image analysis software (FIG. 11B), and were able to compare chromosome number to cell size at individual time points (FIG. 11C) as well as generate an average chromosome number to cell area ratio for each cell over its lifespan. These values remained consistent with minor differences in population distributions throughout multiple generations indicating that we were observing steady state chromosome dynamics (FIG. 11D). By comparing the difference in starting and ending chromosome number to the length of time between cell divisions we were also able to calculate the change in chromosome number per hour for each cell, a value that was again relatively consistent over multiple generations with a median increase of 0.73 chromosomes per hour resulting in 3-4 (median value 3.75) newly replicated chromosomes over the lifespan of a cell. (FIG. 11E).

Because the system enabled tracking information within single-cell derived lineages, we were able to determine whether total chromosome number or the ratio of chromosome number to cell area correlated with measured values for daughter cells. The average chromosome number over a cell lifespan varied between 2.6-7.2 with a median value of 4.7, and did not appear to depend on microcolony position or lineage (FIG. 11F, FIG. 18A). We also found no correlation between the ratio of chromosome number to cell area in mother and daughter cells (FIG. 18B) or between chromosome content in mother cells and gene expression in daughter cells (FIG. 18C-D). The absolute number of chromosomes at division is not consistent between mother cells, and not always an even number, indicating that daughter cells within a population, even those from the same mother cell, may not inherit the same amount of genetic material (FIG. 10G). These results indicate that differences in chromosome content in one generation do not have lasting physiological effects within a lineage under normal growth conditions.

As we and others have observed in non-time lapse imaged cells (FIG. 10E, Zheng & O'Shea, 2017), protein expression normalized to cell size was similar during growth for cells with different numbers of chromosomes under these conditions (FIG. 11H). Interestingly, no differences were detected in either growth rate, the total amount of mOrange2, or the rate of mOrange2 accumulation for cells with differential chromosome replication patterns (FIGS. 11B, C & I—center traces), indicating that variability in chromosome copy number does not lead to variability in growth rate nor in the amount or rate of constitutively expressed proteins under these conditions.

Growth Rate Dictates the Timing of Chromosome Replication and Protein Expression Because PCC 7002 can use photosynthesis as its sole energy source, growth rate can be controlled by varying growth light intensity. To determine how changing growth conditions affects chromosome replication and inheritance, cells were grown with 45 μmol photons $m^{-2}$ $s^{-1}$ of red light (low light—LL) rather than 150 μmol photons $m^{-2}$ $s^{-1}$ (high light—HL) as described above. Under these conditions cells still formed similar microcolony formations during growth, and had similar chromosome dynamics (FIG. 12A), but on a longer time scale (FIGS. 12B, C and F). The distributions of chromosome number to cell area ratio calculated for cells grown in HL or LL are extremely similar (FIG. 12D), indicating that increases in chromosome number must be slower in slower growing cells. These data are consistent with recent results generated from cells grown in batch culture (Ohbayashi et al., 2019), and is confirmed by the significantly lower value for change in chromosome number over time, median of 0.33 chromosome increase per hour, measured in cells growing in LL conditions.

Figure 19:
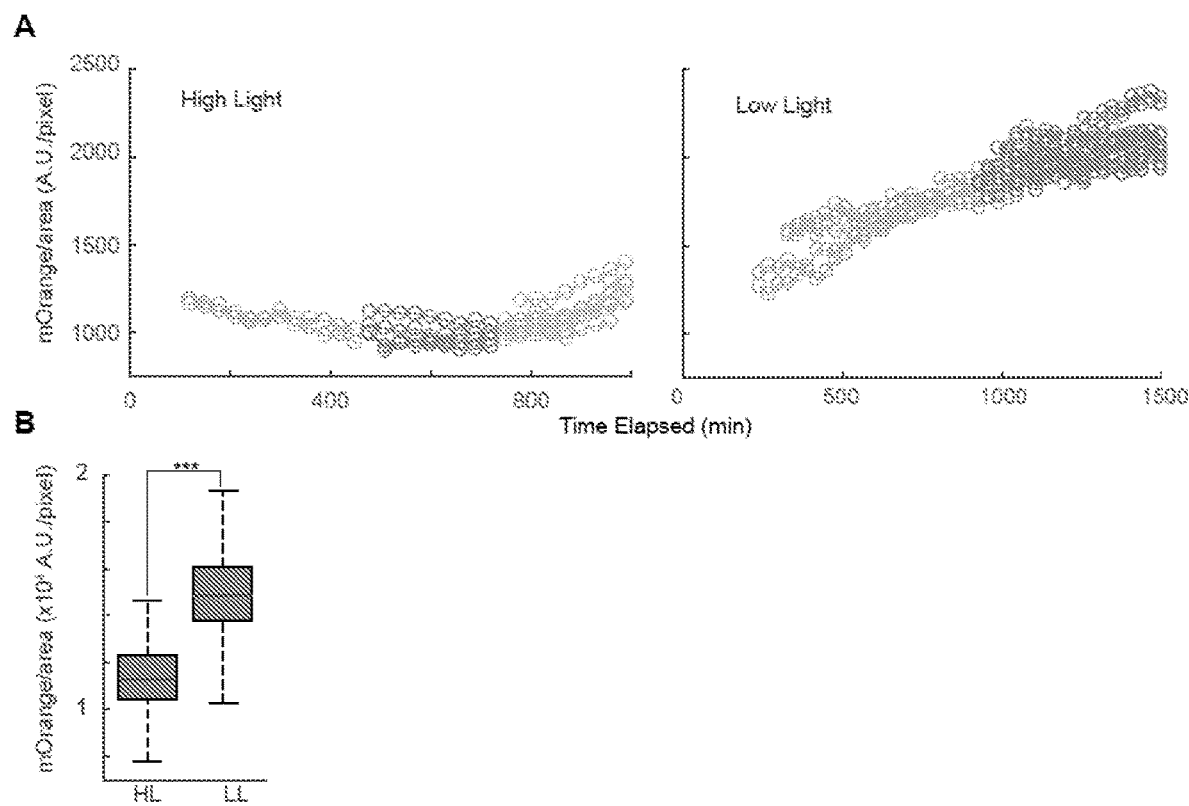
FIG. 19 is a set of graphs depicting (A) mean mOrange2 intensity driven by the pCpt promoter over time for cells grown in HL (left panel) or LL (right panel). (B) mean mOrange2 intensity driven by the BBa_J23119 promoter when cells were grown in batch culture overnight in either high light (HL) or low light (LL) environments. For this experiment white light was used for growth.

Interestingly, mean mOrange2 intensity increased in cells grown at low light (FIG. 12E—Bottom Panel), resulting in a two-fold increase in mOrange2 intensity at the end of the four-cell stage of growth compared to starting mOrange2 intensity. In comparison, mean mOrange2 intensity for cells grown in HL did not increase over the same cell-stages (FIG. 12E—Top Panel). To determine whether the rate of mOrange2 expression increased in LL conditions, the rate of mOrange2 expression was calculated to determine the amount of time it took for cells to double their total mOrange2 intensity when grown in either HL or LL (FIG. 12G). Slower growing cells have longer mOrange2 doubling times compared to fast growing cells indicating a decrease in the rate of gene expression in LL conditions. However, the differences in gene expression rate were smaller than the differences in physical growth rate; therefore, in LL, cells expressed mOrange2 more slowly than in HL, but accumulated more of it over their lifespan (compare doubling times FIGS. 12F and 12G). In these experiments mOrange2 expression was driven by the BBa_J23119 promoter, which is a strong constitutive promoter in both *E. coli* and PCC 7002 (Anderson, 2006; Markley et al., 2015). However, similar effects were observed when mOrange2 is expressed from the Pcpt promoter or when cells are grown in batch culture under differential light conditions prior to imaging (FIG. 19A-B).

To determine the time scale of the impacts of changing growth conditions cells were transitioned from either a HL to LL or LL to HL environment while continuously imaging (FIGS. 12H and O, respectively). Using this method, we were able to categorize cells as growing primarily in HL, LL, or that spanned the transition of growth environments. Regardless of whether cells transition from or to HL conditions, cells grown primarily in HL have shorter doubling times and more chromosome replication per hour compared to cells primarily grown in LL, although the difference in the change in chromosome number over time is modest for cells transitioning from LL to HL (FIGS. 12I-J and P-Q). HL cells also have similar patterns of mOrange2 accumulation to cells grown continuously in HL, in which there is little to no change between the mean mOrange2 value from the beginning to the end of a cell lifespan.

Conversely, for cells shifted either into or out of LL conditions, mean mOrange2 intensity was 30-50% higher in the final frame of the cell trace compared to the initial frame (FIGS. 12K and R). Together these results indicate that changes in growth rate, amount of chromosome replication, and gene expression can be observed in the next generation of cells grown in different environments.

Figure 18:
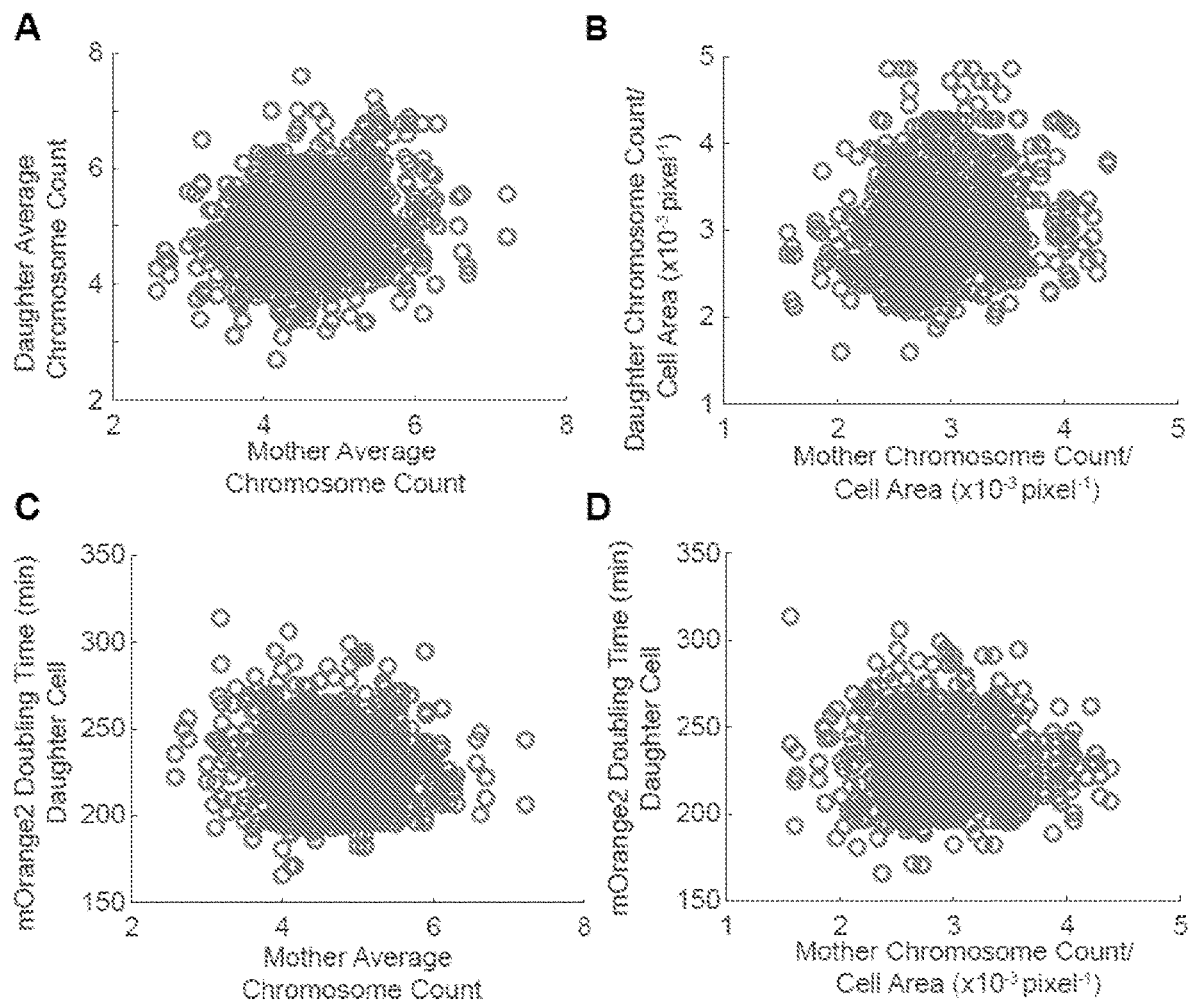
FIG. 18 is a set of graphs depicting analysis of mother-daughter lineage measurements. Comparisons of (A) average chromosome count over a cell lifespan between mother and daughter cells; (B) mean chromosome count per cell area over a cell lifespan between mother and daughter cells; (C) mOrange2 doubling time in daughter cells and average chromosome count in mothers; and (D) mOrange2 doubling time in daughter cells and mean chromosome count per cell area over a cell lifespan in mother cells.

To determine whether the impacts of transitioning growth conditions could be measured within a single generation, cells were observed with traces that spanned the light transition. A correlation between chromosome replication per hour and growth rate is immediately apparent when cells are shifted from HL to LL. These changes are evident within the first hour after the light transition (FIGS. 12L-M—dashed line marks first frame after transition). mOrange2 intensity also starts to increase as soon as cells are shifted to LL, further supporting the hypothesis that changes in growth rate rather than gene expression (which is expected to have a delayed effect) are responsible for increased accumulation of mOrange2 in these cells (FIG. 12N). After shifting cells from LL to HL, we did not observe a distinct change in chromosome replication over time (FIG. 18). However, shifts in both growth rate and mean mOrange2 intensity are observed immediately after the LL to HL transition (FIGS. 12T-U) indicating that these responses may occur on a faster time scale than regulation of chromosome replication for this light transition. Largely, this data supports the theory that polyploid cells are able to rapidly respond to their environment through regulated control of chromosome replication, growth rate, and gene expression resulting in cells with similar chromosome to cell size ratios regardless of growth conditions.

Chromosome Replication and Segregation are Dependent on Cell Size

To investigate the impact of manipulating genes that drive essential processes such as DNA replication and segregation, the CRISPR interference (CRISPRi) system described for PCC 7002 by Gordon et al., (2016) was modified to make an IPTG inducible guide RNA (sgRNA), and engineered it into a strain expressing dCas9, TetR-sfGFP, and the tetO array. This system allowed us to temporally control essential gene expression. Cells were grown in an uninduced state followed by addition of IPTG immediately prior to time-lapse imaging. With this platform we were able to observe the dynamics of chromosome replication and division as essential gene expression decreased over time.

Figure 13:
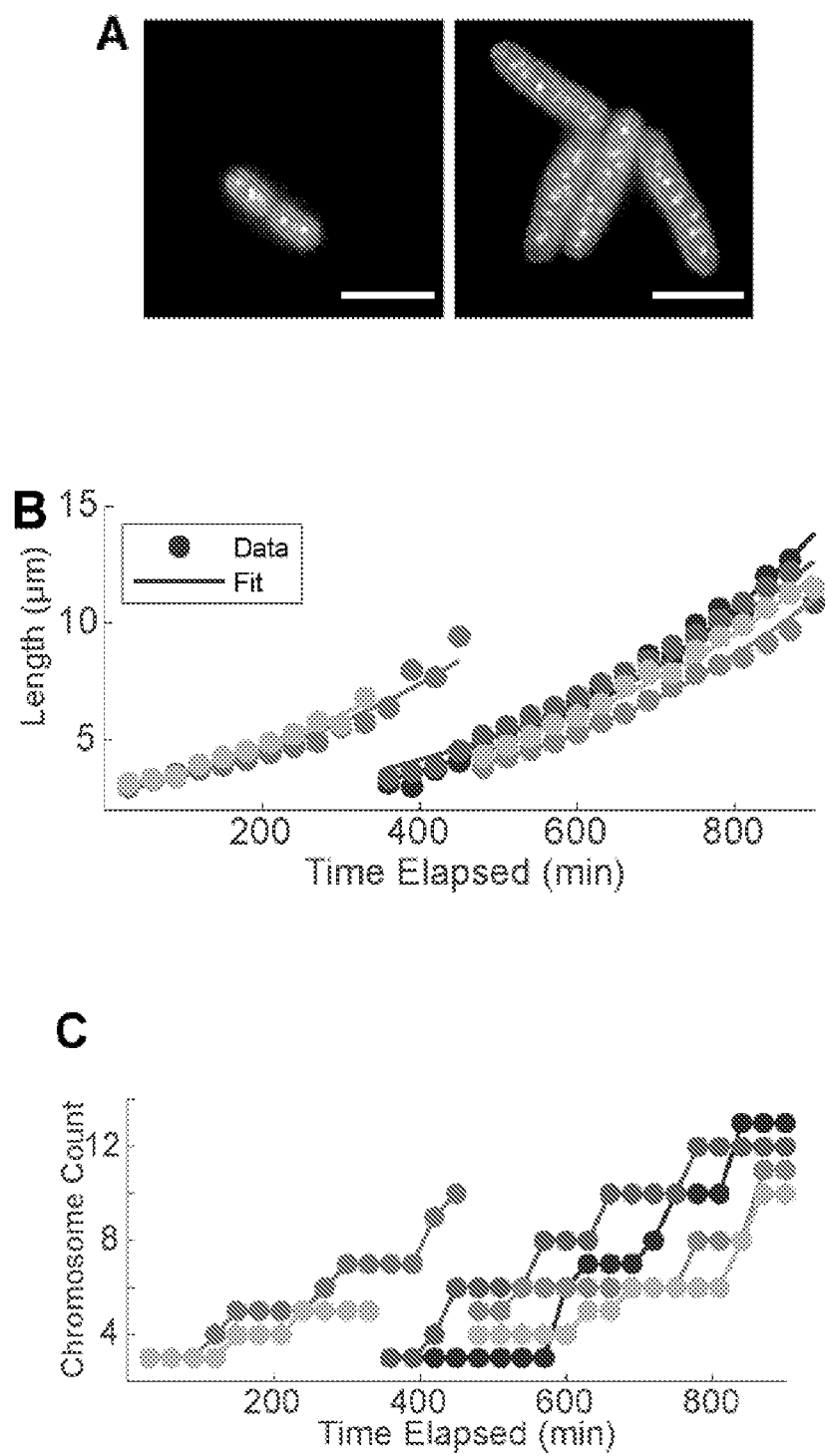
FIG. 13 is a set of images and graphs depicting the effect of cell division on chromosome dynamics. (A) Time-lapse images of labeled chromosomes in ftsZ sgRNA::tetO array:: TetR-sfGFP-dCas9 (CRISPRi) cells grown for 21.5 hr. For all CRISPRi time-lapse images, 5 mM IPTG was added to agarose imaging pad to induce sgRNA expression 15 minutes prior to the first image. (B-C) Cell length and chromosome count, respectively, in $1^{st}$ (orange) and $2^{nd}$ (purple) generation ftsZ-targeting CRISPRi cells. (D-E) Chromosome count per cell area averaged over the lifespan of the cell and Δ chromosome #/hr, respectively, for cells with or without an sgRNA targeting ftsZ (2nd generation and later). $N_{-sgRNA}$=315, $N_{ftsZ\ CRISPRi}$=93. (F) Left: schematic of the effect of MinD depletion on cell division. Right: 8-cell microcolony of minD sgRNA::TetO array::TetR-sfGFP-dCas9 (G) Chromosome segregation plot of minD sgRNA:: TetO array::TetR-sfGFP-dCas9. Only cells in the 3rd generation or later were analyzed. $N_{mother}$=43, $N_{daughter}$=86. (H) Chromosome Count to cell area ratio distributions for small cells (starting cell length <10th percentile of -sgRNA cells) and large cells (starting cell length >90th percentile of -sgRNA cells). $N_S$=125, $N_L$=175. Scale bar=5 μm.

Previous studies have noted that inhibiting cell division in monoploid bacteria does not immediately impact nucleoid number or spacing (Dai & Lutkenhaus, 1991). However, upon prolonged blockage of cell division, DNA replication is inhibited (Arjes et al., 2014). To determine whether cell division regulates DNA replication, resulting in disruption of the chromosome to cell area ratio observed in control PCC 7002 cells, cells were imaged for 20 hr after induction of an sgRNA targeting ftsZ, an essential gene for cell division (FIG. 13A). Uninduced cells grew similarly to cells lacking a guide RNA. However, within one generation of ftsZ CRISPRi induction, we observed an arrest of cell division was observed resulting in elongation of cells (FIG. 13B). Over the 20 hr imaging span (approximately the equivalent of 4-5 uninduced doublings), we did not observe any decrease in cell growth (FIG. 13B). During this period chromosome replication continued unimpeded (FIG. 13C), and the distribution of chromosome number to cell area ratios was marginally higher in ftsZ CRISPRi induced cells compared to control cells (FIG. 13D), indicating that chromosome replication is not inhibited by FtsZ depletion (FIG. 13E).

To determine whether uneven division of cells could result in disrupted chromosome to cell area ratios we depleted minD with CRISPRi. MinD depleted cells have irregular septum placement, resulting in both larger and smaller cells than control cells (FIG. 13F). As evident from both visual and quantitative analysis, it is clear that chromosomes were not split evenly into large and small cells, but rather that the number of chromosomes segregated into each daughter cell was proportional to cell size (FIG. 13G). MinD depleted cells provided us with an additional tool to study differences between large and small cells with very different absolute chromosome numbers. When cells were grouped into "small" or "large" cell classifications based on cell length at birth, we did not observe distinct differences in cell physiology. The distributions of chromosome to cell area ratio for the smallest and largest cells were also almost identical (FIG. 13H). These results indicate that chromosome segregation in PCC 7002 is based on chromosome localization and septum placement leading to consistent chromosome to cell area ratios.

Cell Growth is Independent of Chromosome Replication

Figure 20:
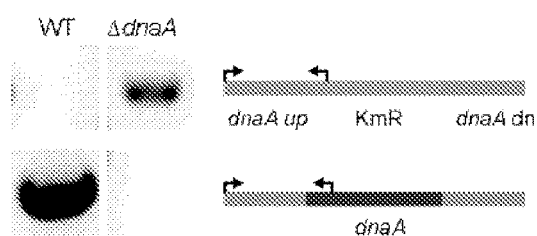
FIG. 20 is an image and a schematic showing the analysis of ΔdnaA (related to FIG. 14). PCR products confirming presence of KmR insert at the dnaA locus (top panel) and absence of WT product (bottom panel).

Previous work in several polyploid bacteria has indicated that current models of DNA replication, specifically the requirement for dnaA and a well-defined oriC site, may not be conserved across the bacterial kingdom, including in PCC 7002 (Gehring et al., 2017; Ohbayashi et al., 2020, 2016; Richter, Hagemann, & Messer, 1998). In further support of this assertion, we found that in PCC 7002, dnaA (Synpcc7002_A0001) was not required for DNA replication for any conditions tested (FIG. 14A-B). ΔdnaA cells with labeled chromosomes grow and have similar chromosome to area ratios as cells that are WT at the dnaA locus under standard growth conditions (FIG. 14C-D). dnaA deletion was confirmed by PCR (FIG. 20). There are no additional dnaA homologs within PCC 7002, and canonical clustering of DnaA binding sites is also absent from the genome, further indicating that the role of DnaA is not conserved across bacterial species.

Figure 14:
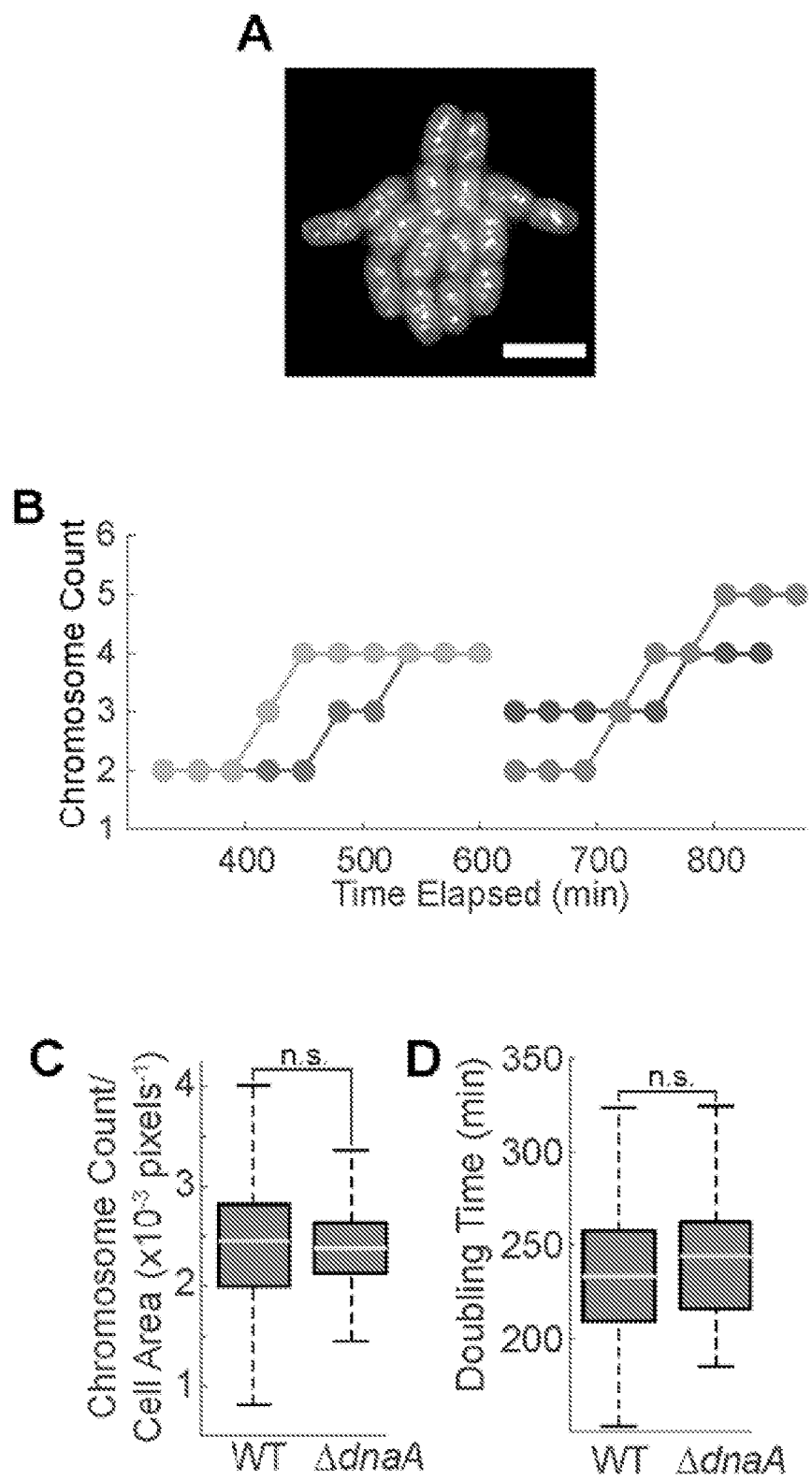
FIG. 14 is a set of images and graphs depicting chromosome replication in PCC 7002. (A) Labelled chromosomes at the 16-cell microcolony stage in ΔdnaA::TetO array:: TetR-sfGFP cells. Cells grown for 19.5 hr. (B) Chromosome count over time at the 2-cell (orange) and 4-cell (purple) stage of ΔdnaA::TetO array::TetR-sfGFP cells. (C-D) Chromosome count per cell area averaged over the lifespan of the cell and length doubling time, respectively, for cells WT or mutant at the dnaA locus. $N_{WT}$=272, $N_{ΔdnmA}$=124 (E) Time-lapse images of dnaX sgRNA::tetO array::TetR-sfGFP-dCas9 CRISPRi cells grown for 26 hr. Arrow colors correspond to graphs in H. (F) Chromosome count per cell area in mother cells (x-axis) vs. chromosome count per cell area in daughter cells (y-axis) in dnaX CRISPRi treated cells $N_{mother}$=357, $N_{daughter}$=711. (G) Chromosome count per cell area compared to doubling time. Dot color represents cell generation in lineage. Orange=$2^{nd}$ generation N=480, purple=$3^{rd}$ generation N=381, and green=$4^{th}$ generation N=159 dnaX CRISPRi cells. (H) Length over time for $1^{st}$ (orange), $2^{nd}$ (purple), and $3^{rd}$ (green) generation dnaX CRISPRi cells. (I) Time-lapse images of dnaX sgRNA::tetO array::TetR-sfGFP-dCas9 CRISPRi cells grown for 26 hr. White arrow indicates cell without chromosome. Scale bar=5 μm.

To determine the effects of inhibiting DNA replication on PCC 7002, we used CRISPRi to target dnaX, an essential component of the DNA polymerase holoenzyme (Blinkova et al., 1993). This method allowed us to visualize dilution of chromosomes over time (FIG. 14). Unlike control cells (FIG. 18B), we observed a proportional correlation between chromosome content in mother and daughter cells. We also observed that on average the chromosome per area ratio was lower in daughter cells than in mother cells as evidenced by a slope of 0.61 for the best fit linear model for the data (FIG. 14F). These data indicate that chromosome dilution occurs throughout a cell lineage, and that later generation cells will have experienced decreased chromosome per area ratios over extended periods of time.

Interestingly, decreased chromosome per area ratios do not appear to impact cells in early generations as growth rate for the majority of 2nd and 3 rd generation cells remain consistent even in cells with diluted chromosome content. Only in later generations or cells with extremely low chromosome to area ratios are slower growth rates commonly observed (FIG. 14G). Although cell growth was not immediately impacted by disruption of chromosome replication, we noted multiple instances of cells with delayed or arrested cell division resulting in cells that either grew and did not divide or cells that grew to an extended length before division (FIG. 14H, compare left and center traces). These results support a model in which dilution of chromosomes does not have immediate impacts on cell growth, but that extended depletion results in inhibited cell division and eventual growth arrest possibly because chromosome copy number has become limiting for gene expression.

Surprisingly in a very small percentage (~2%) of dnaX CRISPRi induced cell lineages, we observed cells in which chromosomes were only segregated into one of two daughter cells early in a lineage (FIG. 14I). However, these cells often continued to grow at similar rates as their sister cells containing chromosome puncta, indicating that chromosomeless cells can remain physiologically viable without a full complement of genetic material when chromosomes are rapidly depleted rather than slowly diluted as occurred in the majority of cell lineages.

Continued Growth and Division of PCC 7002 in Absence of Chromosomal DNA

Figure 15:
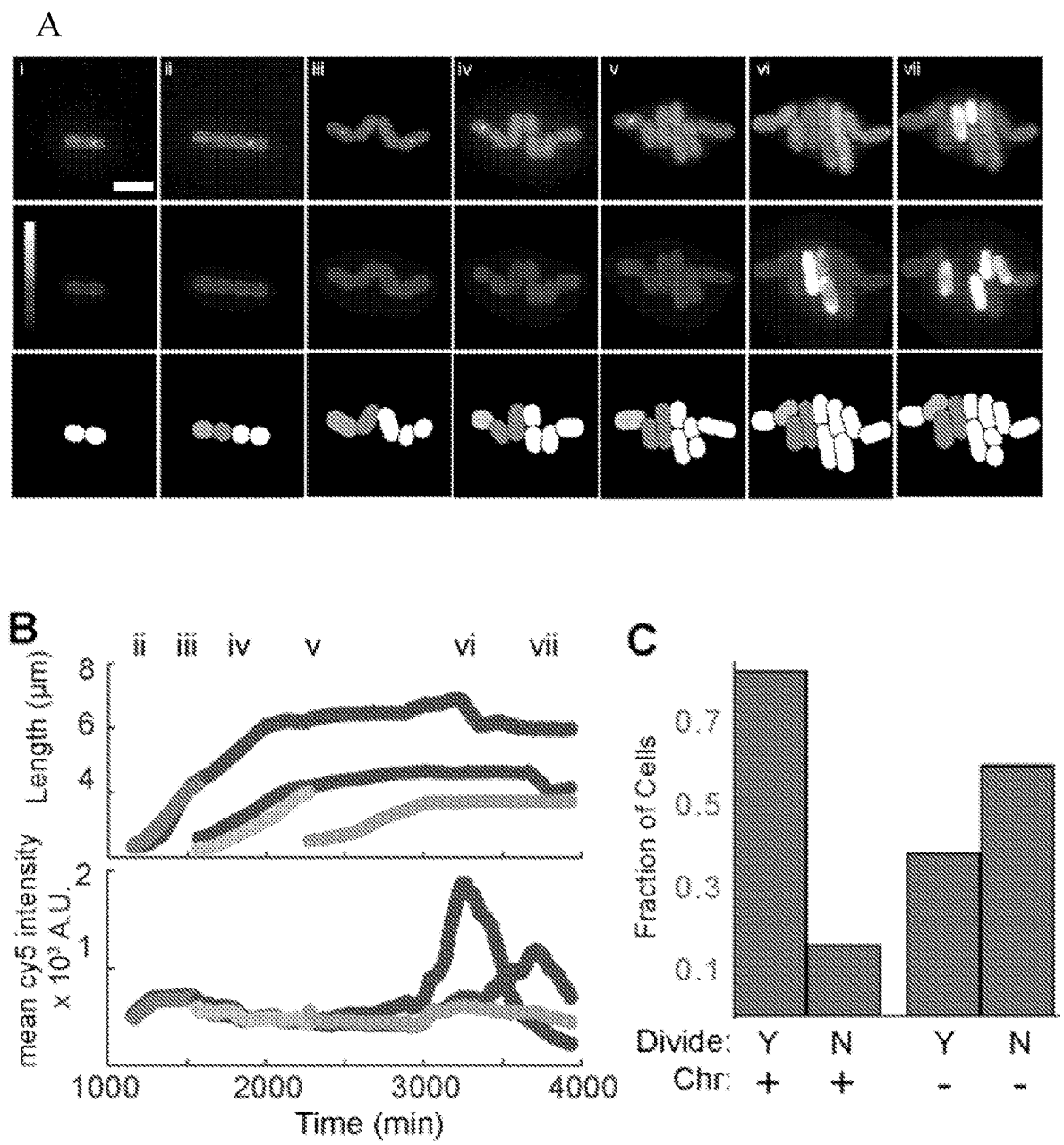
FIG. 15 is a set of images and graphs depicting rapid chromosome mis-segregation in PCC 7002. (A) Time-lapse images of labeled chromosomes (top panel) and endogenous fluorescence from thylakoid membranes (middle panel) without aTC for 65 hr. Bottom panel represents cell masks with colors corresponding to cell traces in B. Calibration bar represents intensities between 75-2450 A.U. (B) Cell length (top panel), and mean emission intensity after 640 nm excitation representing photosynthetic capacity (bottom panel), plotted over time. (C) The fraction of cells with at least one (Chr+) or without chromosomes (Chr−) that divide within 25 hr. N=310. (D) Heatmap of mean emission intensity after 640 nm excitation over time for cells with (left) or without (right) a chromosome spot. T0=first frame after division. Cells with only one chromosome spot that divided and cells without chromosomes that did not divide were analyzed. N=116. (E) Time-lapse images of mOrange2::tetO array::TetR-sfGFP cells treated with rifampicin to block transcription. (F) Time-lapse images of mOrange2::tetO array::TetR-sfGFP cells treated with chloramphenicol to block translation. For A Scale bar=5 μm. For E-F, scale bar=1 μm.

To further investigate the impacts of chromosome loss that occurred early in cell lineages, we took advantage of the extensive TetR binding to the tetO array that occurs in the absence of aTC, to disrupt chromosome replication and segregation, as previously observed in monoploid bacteria (Bernard, Marquis, & Rudner, 2010). Under standard growth and imaging procedures, we grew cells with aTC to ensure that chromosome dynamics were minimally perturbed. However, to determine whether excessive TetR binding could result in rapid mis-segregation of chromosome aggregates, chromosome labeled cells were grown to stationary phase without aTC in shaking flasks and cells were imaged on fresh media without aTC over a 65 hr time frame. Under these conditions, cells with single GFP-labeled puncta were observed, which may represent one or more chromosomes (FIG. 15A). Unlike stationary phase cells grown on fresh media in the presence of aTC, the number of chromosome puncta did not increase with growth in the vast majority of cells grown without aTC. This may be due to a block in chromosome replication, oligomerization of sfGFP bound to multiple chromosomes, or both.

Cells with single chromosome puncta grew, albeit at a slower rate than cells with normal chromosome dynamics. These cells also divided resulting in uneven segregation of the chromosome puncta between daughter cells (FIG. 15A). Similar to the results from dnaX treated cells that segregated individual chromosome punta, cells that did not receive a chromosome after division continued to grow (FIG. 15B, upper traces), and ~40% of these cells were able to divide at least once, indicating that the initial absence of a chromosome has minimal impact on cell physiology, and that neither the presence of a chromosome nor its replication is absolutely required for cell division in PCC 7002 (FIG. 15C).

After ~1-2 generation periods, cell division became impaired and eventually growth arrested in all cells lacking chromosomes. After ~24 hr, an increase in endogenous fluorescence was observed originating from the thylakoid membranes, evidenced by the increased emission after 640 nm excitation, indicating that the photosynthetic machinery had become dysfunctional. This is likely because repair of damaged photosystems requires de novo gene expression which is impossible without genetic inputs (Maxwell & Johnson, 2000) (FIG. 15A middle panel, B bottom panel and D right panel). Endogenous fluorescence has been pseudo-colored in the middle panel of FIG. 15A to better visualize changes in intensity. In contrast, endogenous fluorescence did not increase in cells that divided and contained at least one chromosome spot (FIG. 15D—Left panel), indicating that cells lacking chromosome puncta are physiologically different than cells with puncta, rather than an artifact of the experimental system. The relative consistency of the timing between chromosome loss and spikes in endogenous fluorescence (FIG. 15D), support a model in which cells have the capacity to grow, divide, and perform photosynthesis for multiple generation periods before genetic inputs become a limiting factor for cell viability.

To determine whether inhibiting transcription or translation resulted in similar effects on photosynthetic machinery, cells were treated with either rifampicin to block transcription or chloramphenicol to block translation. Similar increases in endogenous fluorescence were observed with both inhibitors indicating that the effect of blocking downstream mechanisms required for de novo gene expression results in similar cellular disfunction as chromosome loss. (FIG. 15E-F). Together these data support a model in which loss of genetic inputs leads to diminished gene expression resulting in dysfunctional cell division, similar to that observed in chromosome depleted cells, and the inability to repair photosynthetic damage.

Although the regulation of DNA replication and inheritance has been long-studied in model strains of monoploid bacteria, the results demonstrated herein raise questions about the fundamental understanding of these processes across bacterial species. Here, single-cell time-lapse imaging was used to demonstrate both conserved and variable characteristics of bacterial DNA regulation between traditionally studied monoploid bacteria and polyploid strains. The data herein support the theory that the ratio of chromosome content to cell size is preserved in polyploid strains under different growth conditions (FIG. 12D) similar to what has been observed in monoploid strains (Donachie & Begg, 1989; Sargent, 1975). However, chromosome replication does not depend on, nor does it cause cell growth or division, as evidenced by continuous chromosome replication when cell division is inhibited (FIG. 13A) and continued cell growth and division when DNA replication is impeded (FIG. 14E). These results support the theory that chromosome replication is regulated by cell growth leading to consistent chromosome to cell size ratios, but that this regulation is essentially uncoupled from cell division in polyploid bacteria.

In contrast to the canonical model of chromosome segregation we did not observe strictly even partitioning of chromosomes into daughter cells (FIG. 11G and FIG. 13F-G), indicating that inheritance of specific chromosomes is based solely on chromosome positioning at the time of cell division. In PCC 7002 we also did not observe specific linear patterning of chromosomes prior to division as was observed for in PCC 7942 (Chen et al., 2012), but did see relatively even spacing of chromosomes throughout the cell resulting in broadly consistent chromosome to cell size ratios for newly divided cells. The mechanisms (or lack thereof) regulating chromosome segregation remain an interesting topic for future studies.

In a move towards determining the consequences of polyploidy on cell physiology, we monitored constitutive gene expression in polyploid cells. We found that chromosome copy number is not a major factor in determining protein content within a cell or its progeny in polyploid bacteria (FIGS. 11B and I, FIG. 18C-D). Rather, growth rate appears to be the predominant driver of protein expressed from constitutive promoters in these cells (FIG. 12E-G). We observe that shifts in growth rate and constitutive gene expression occur rapidly within the same generation of environmental changes, indicating that these responses likely do not depend on transcriptional or translational "re-programming" of the cell (FIGS. 12L-N and S-U). In contrast, the effects of CRISPRi, which do rely on changes in transcription and translation are not apparent for at least a generation and in most cases two generations. Our results support the hypothesis that chromosome copy number is not the limiting factor in protein production in polyploid cells grown under standard conditions, and are consistent with predictions made by several recent models of gene expression (Klumpp, Zhang, & Hwa, 2009; Lin & Amir, 2018).

Gene expression in these experiments was driven by non-native promoters that are expected to be independent of growth light intensity and may respond differently than endogenous promoter systems. Furthermore, in polyploid cells, it is possible that heterozygous alleles may be present on different chromosomes. It will be interesting for future studies to determine whether copy number may in fact be important for relative gene expression from allelic variants in polyploid cells. A more thorough understanding of how chromosome copy number and growth rate affect nuanced types of gene expression, such as inducible and native promoter systems, in both monoploid and polyploid cells, will be essential for understanding general bacterial physiology, as well as for designing functional synthetic biology circuits in bacteria.

Lastly, we demonstrated that polyploid cells have the capacity to compensate for disruption to chromosome replication and even chromosome loss at points early in a cell lineage. Cells with excessively diminished chromosomes numbers and even those lacking chromosomes are able to grow and divide (FIGS. 14E and I and FIGS. 15A and C). Long-term dilution of chromosomes or complete chromosomal loss eventually inhibits both cell division and arrests cell growth, indicating that although polyploid cells can function with moderate disruptions to chromosome maintenance, prolonged depletion of chromosomes is detrimental for polyploid cells. This inability to sustain a continuously low numbers of chromosomes indefinitely may indicate that chromosome copy number can be limiting in these conditions. Consistent with this hypothesis, long-term dilution or lack of chromosomes results in photosynthetic damage (FIGS. 15A and D), which is a known consequence of inhibiting de novo gene expression, and also occurs after substantial DNA damage (Aro, Virgin, & Andersson, 1993; Sass, Spetea, Máté, Nagy, & Vass, 1997; Vass, Kós, Sass, Nagy, & Vass, 2013). These observations indicate that polyploid bacteria may be able to survive in conditions that result in decreased chromosome numbers or after moderate chromosomal insults, allowing them to function and replicate in a variety of suboptimal environments.

REFERENCES (PART 2)

Anderson, J. (2006). Registry of Standard Biological Parts. Retrieved Aug. 28, 2019, from http://parts.igem.org/Part: BBa_J23119

Arjes, H. A., Kriel, A., Sorto, N. A., Shaw, J. T., Wang, J. D., & Levin, P. A. (2014). Failsafe Mechanisms Couple Division and DNA Replication in Bacteria. *Current Biology*, 24(18), 2149— 2155.

Aro, E.-M., Virgin, I., & Andersson, B. (1993). Photoinhibition of Photosystem II. Inactivation, protein damage and turnover. *Biochimica et Biophysica Acta (BBA)—Bioenergetics*, 1143(2), 113-134.

Bernard, R., Marquis, K. A., & Rudner, D. Z. (2010). Nucleoid occlusion prevents cell division during replication fork arrest in *Bacillus subtilis*. *Molecular Microbiology*, 78(4), 866-882.

Blin, K., Pedersen, L. E., Weber, T., & Lee, S. Y. (2016). CRISPy-web: An online resource to design sgRNAs for CRISPR applications. *Synthetic and Systems Biotechnology*, 1(2), 118-121.

Blinkova, A., Hervas, C., Stukenberg, P. T., Onrust, R., O'Donnell, M. E., & Walker, J. R. (1993). The *Escherichia coli* DNA polymerase III holoenzyme contains both products of the dnaX gene, tau and gamma, but only tau is essential. *Journal of Bacteriology*, 175(18), 6018-6027. Retrieved from Bryant, J. A., Sellars, L. E., Busby, S. J. W., & Lee, D. J. (2014). Chromosome position effects on gene expression in *Escherichia coli* K-12. *Nucleic Acids Research*, 42(18), 11383-11392.

Chandler, M. G., & Pritchard, R. H. (1975). *The Effect of Gene Concentration and Relative Gene Dosage on Gene Output in Escherichia coli* (Vol. 138). Springer-Verlag.

Chen, A. H., Afonso, B., Silver, P. A., & Savage, D. F. (2012). Spatial and Temporal Organization of Chromosome Duplication and Segregation in the Cyanobacterium *Synechococcus elongatus* PCC 7942. *PLoS ONE*, 7(10), 1-10.

Clark, R. L., McGinley, L. L., Purdy, H. M., Korosh, T. C., Reed, J. L., Root, T. W., & Pfleger, B. F. (2018). Light-optimized growth of cyanobacterial cultures: Growth phases and productivity of biomass and secreted molecules in light-limited batch growth. *Metabolic Engineering*, 47, 230-242.

Clay Montier, L. L., Deng, J. J., & Bai, Y. (2009). Number matters: control of mammalian mitochondrial DNA copy number. *Journal of Genetics and Genomics*, 36(3), 125-131.

Cooper, S., & Helmstetter, C. E. (1968). Chromosome replication and the division cycle of *Escherichia coli* Br. *Journal of Molecular Biology*, 31(3), 519-540.

Dai, K., & Lutkenhaus, J. (1991). *ftsZ Is an Essential Cell Division Gene in Escherichia coli*. JOURNAL OF BACTERIOLOGY (Vol. 173).

Davies, F. K., Work, V. H., Beliaev, A. S., & Posewitz, M. C. (2014). Engineering Limonene and Bisabolene Production in Wild Type and a Glycogen-Deficient Mutant of *Synechococcus* sp. PCC 7002. *Frontiers in Bioengineering and Biotechnology*, 2, 21.

Donachie, W. D., & Begg, K. J. (1989). Cell length, nucleoid separation, and cell division of rod-shaped and spherical cells of *Escherichia coli*. *Journal of Bacteriology*, 171(9), 4633-4639.

Gehring, A. M., Astling, D. P., Matsumi, R., Burkhart, B. W., Kelman, Z., Reeve, J. N., Santangelo, T. J. (2017). Genome Replication in *Thermococcus kodakarensis* Independent of Cdc6 and an Origin of Replication. *Frontiers in Microbiology*, 8, 2084.

Green, M. R. (Michael R., Sambrook, J., & Sambrook, J. (2012). *Molecular cloning: a laboratory manual*. Cold Spring Harbor Laboratory Press.

Jain, I. H., Vijayan, V., & O'Shea, E. K. (2012). Spatial ordering of chromosomes enhances the fidelity of chromosome partitioning in cyanobacteria. *Proceedings of the National Academy of Sciences*, 109(34), 13638-13643.

Jaqaman, K., Loerke, D., Mettlen, M., Kuwata, H., Grinstein, S., Schmid, S. L., & Danuser, G. (2008). Robust single-particle tracking in live-cell time-lapse sequences. *Nature Methods*, 5(8), 695-702.

Klumpp, S., Zhang, Z., & Hwa, T. (2009). Growth Rate-Dependent Global Effects on Gene Expression in Bacteria. *Cell*, 139(7), 1366-1375.

Lin, J., & Amir, A. (2018). Homeostasis of protein and mRNA concentrations in growing cells. *Nature Communications*, 9(1), 4496.

Liu, H., & Deutschbauer, A. M. (2018). Rapidly moving new bacteria to model-organism status. *Current Opinion in Biotechnology*, 51, 116-122.

Locey, K. J., & Lennon, J. T. (2016). Scaling laws predict global microbial diversity. *Proceedings of the National Academy of Sciences of the United States of America*, 113(21), 5970-5975.

Lowe, D. G. (1999). Object recognition from local scale-invariant features. In *Proceedings of the Seventh IEEE International Conference on Computer Vision* (pp. 1150-1157 vol.2). IEEE.

Markley, A. L., Begemann, M. B., Clarke, R. E., Gordon, G. C., & Pfleger, B. F. (2015). Synthetic biology toolbox for controlling gene expression in the cyanobacterium *Synechococcus* sp. strain PCC 7002. *ACS Synthetic Biology*, 4(5), 595-603.

Maxwell, K., & Johnson, G. N. (2000). Chlorophyll fluorescence—a practical guide. *Journal of Experimental Botany*, 51(345), 659-668.

Michaelis, C., Ciosk, R., & Nasmyth, K. (1997). Cohesins: Chromosomal Proteins that Prevent Premature Separation of Sister Chromatids. *Cell*, 91(1), 35-45.

Moore, K. A., Altus, S., Tay, J. W., Meehl, J. B., Johnson, E. B., Bortz, D. M., & Cameron, J. C. (2020). Mechanical regulation of photosynthesis in cyanobacteria. *Nature Microbiology*, 5(5), 757-767.

O'Donnell, M., Langston, L., & Stillman, B. (2013). Principles and concepts of DNA replication in bacteria, archaea, and eukarya. *Cold Spring Harbor Perspectives in Biology*, 5(7).

Ohbayashi, R., Hirooka, S., Onuma, R., Kanesaki, Y., Hirose, Y., Kobayashi, Y., Miyagishima, S. Y. (2020). Evolutionary Changes in DnaA-Dependent Chromosomal Replication in Cyanobacteria. *Frontiers in Microbiology*, 11.

Ohbayashi, R., Nakamachi, A., Hatakeyama, T. S., Watanabe, S., Kanesaki, Y., Chibazakura, T., Miyagishima, S.-Y. (2019). Coordination of Polyploid Chromosome Replication with Cell Size and Growth in a Cyanobacterium. *M Bio*, 10(2), e00510-19.

Ohbayashi, R., Watanabe, S., Ehira, S., Kanesaki, Y., Chibazakura, T., & Yoshikawa, H. (2016). Diversification of DnaA dependency for DNA replication in cyanobacterial evolution. *The ISME Journal*, 10(5), 1113-1121.

Pecoraro, V., Zerulla, K., Lange, C., & Soppa, J. (2011). Quantification of ploidy in proteobacteria revealed the existence of monoploid, (mero-)oligoploid and polyploid species. *PLoS ONE*, 6(1).

Reyes-Lamothe, R., Nicolas, E., & Sherratt, D. J. (2012). Chromosome Replication and Segregation in Bacteria. *Annual Review of Genetics*, 46(1), 121-143.

Richter, S., Hagemann, M., & Messer, W. (1998). Transcriptional analysis and mutation of a dnaA-like gene in *Synechocystis* sp. strain PCC 6803. *Journal of Bacteriology*, 180(18), 4946-4949.

Sakamoto, W., & Takami, T. (2018). Chloroplast DNA Dynamics: Copy Number, Quality Control and Degradation. *Plant and Cell Physiology*, 59(6), 1120-1127.

Sargent, M. G. (1975). Control of cell length in *Bacillus subtilis*. *Journal of Bacteriology*, 123(1), 7-19.

Sass, L., Spetea, C., Mate, Z., Nagy, F., & Vass, I. (1997). *Repair of UV-B induced damage of Photosystem II via de novo synthesis of the D1 and D2 reaction centre subunits in Synechocystis sp. PCC 6803. Photosynthesis Research* (Vol. 54). Kluwer Academic Publishers.

Schindelin, J., Arganda-Carreras, I., Frise, E., Kaynig, V., Longair, M., Pietzsch, T., Cardona, A. (2012). Fiji: an open-source platform for biological-image analysis. *Nature Methods*, 9(7), 676-682.

Segall-Shapiro, T. H., Sontag, E. D., & Voigt, C. A. (2018). Engineered promoters enable constant gene expression at any copy number in bacteria. *Nature Biotechnology*, 36(4), 352-358.

Selmecki, A. M., Maruvka, Y. E., Richmond, P. A., Guillet, M., Shoresh, N., Sorenson, A. L., . . . Pellman, D. (2015). Polyploidy can drive rapid adaptation in yeast. *Nature*, 519(7543), 349-351.

Soppa, J. (2017). Polyploidy and community structure. *Nature Microbiology*, 2 (January), 1-2.

Stevens, S. E., Patterson, C. O. P., & Myers, J. (1973). THE PRODUCTION OF HYDROGEN PEROXIDE BY BLUE-GREEN ALGAE: A SURVEY. *Journal of Phycology*, 9(4), 427-430.

Van de Peer, Y., Mizrachi, E., & Marchal, K. (2017). The evolutionary significance of polyploidy. *Nature Reviews Genetics*, 18(7), 411-424.

Vass, I.-Z., Kós, P. B., Sass, L., Nagy, C. I., & Vass, I. (2013). The Ability of Cyanobacterial Cells to Restore UV-B Radiation Induced Damage to Photosystem II is Influenced by Photolyase Dependent DNA Repair. *Photochemistry and Photobiology*, 89(2), 384-390.

Zerulla, K., Chimileski, S., Nather, D., Gophna, U., Papke, R. T., & Soppa, J. (2014). DNA as a phosphate storage polymer and the alternative advantages of polyploidy for growth or survival. *PLoS ONE*, 9(4).

Zheng, X. yu, & O'Shea, E. K. (2017). Cyanobacteria Maintain Constant Protein Concentration despite Genome Copy-Number Variation. *Cell Reports*, 19(3), 497-504

Definitions

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

TABLE 1

Strains used in this study.

| Name | Number | Description | Resistance |
|---|---|---|---|
| WT | — | Wild-type *Synechococcus* sp. PCC 7002 | None |
| RbcL-GFP | scJC0029 | WT cells transformed with sJC0028 | Gm |
| Δccm | scJC0062 | RbcL-GFP cells transformed with sJC0103 | Km, Gm |
| Δccm⁺ | scJC0138 | Δccm cells transformed with sJC0187 | Km, Gm, Spec |

TABLE 2

Plasmids used in this study.

| Name | Number | Description | Neutral Site |
|---|---|---|---|
| RbcL-GFP_Gm | sJC0028 | pK2-RbcL-sfGFP downstream of Gm cassette | glpK |
| ΔccmOp_Km | sJC0103 | Km cassette flanked by ccm operon upstream and downstream homology arms | — |
| cLac_ccmOp | sJC0187 | lac promoter-controlled ccm operon, upstream of lac repressor and spec cassette | acsA |

TABLE 3

Primers used in this study.

| Name | Description | Sequence (5'-3') |
|---|---|---|
| NCH17F_seq | To test via colony PCR for presence of RbcL-GFP insert in PCC 7002 genome | agcctggcccgtgaaggtaa [SEQ ID NO: 1] |
| NCH_10r | To test via colony PCR for presence of RbcL-GFP insert in PCC 7002 genome | gtcttttttaaattcaatgggttttacgttagag [SEQ ID NO: 2] |
| KAMo0034 | To test via colony PCR for presence of glpK neutral site in PCC 7002 genome | taaccaagattccggtacgc [SEQ ID NO: 3] |
| EBJp0091 | To test via colony PCR for presence of glpK neutral site in PCC 7002 genome | gatgctgtaggcaagag [SEQ ID NO: 4] |
| KAMo0113 | To test via colony PCR for presence of Δccm insert in PCC 7002 genome | cgactgaatccggtgagaat [SEQ ID NO: 5] |
| EBJp0006 | To test via colony PCR for presence of native ccm operon in PCC 7002 genome | ataggttctgaattgttctacttcttcggtgt [SEQ ID NO: 6] |
| EBJp0048 | To use in colony PCR with both KAMo0113 and EBJp0006 | cggtggagacgatgatccg [SEQ ID NO: 7] |
| PET_218 | To test via colony PCR for presence of Δccm$^+$ insert in PCC 7002 genome | gtttctggaaatcacagaggatgcgtg [SEQ ID NO: 8] |
| EBJp0181 | To test via colony PCR for presence of acsA neutral site in PCC 7002 genome | tcatcctctataccagc [SEQ ID NO: 9] |
| EBJp0092 | To use in colony PCR with both PET_218 and EBJp0181 | atgaatcgggtcaacag [SEQ ID NO: 10] |
| NCH92F_V | Vector amplification of pALM179 (14) derivative, containing acsA neutral sites with cLac143 promoter, LacI, and spec resistance cassette | tgagccttagcgagggcggtgctttgg [SEQ ID NO: 11] |
| NCH92R_V | Vector amplification of pALM179 (14) derivative, containing acsA neutral sites with cLac143 promoter, LacI, and spec resistance cassette | ctcgcttatcacttgactttatgagttgg tgtgtgaaat [SEQ ID NO: 12] |
| NCH93F_F | Insert amplification of ccm operon from PCC 7002 genome | aaagtcaagtgataagcgaggataaa ttagatgcctattgcag [SEQ ID NO: 13] |
| NCH93R_F | Insert amplification of ccm operon from PCC 7002 genome | accgccctcgctaaggctcatctggtt gatttgg [SEQ ID NO: 14] |

TABLE 4

Figure 9:
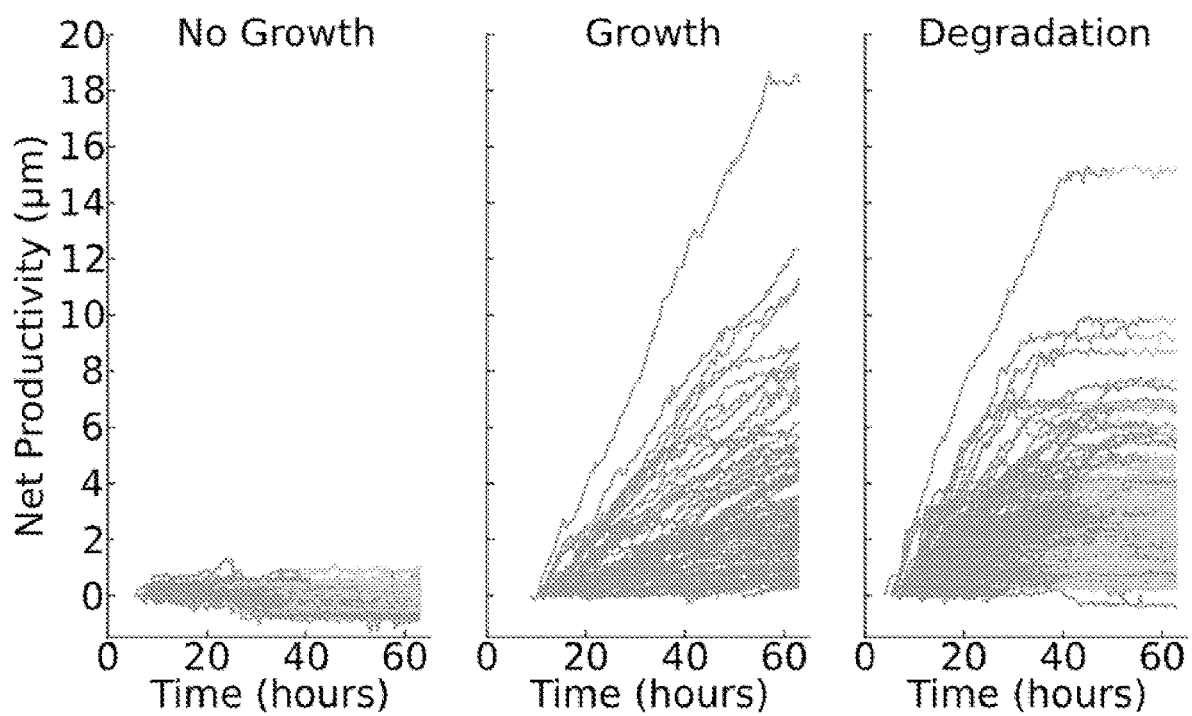
FIG. 9 is a set of graphs depicting clustering of single-carboxysome trees. All single-carboxysome trees that included a carboxysome present for at least 13 hours (n=431) were clustered into the 'No Growth', 'Growth', or 'Degradation' clusters. Dark gray and light gray shading indicate 1 or 0 carboxysomes present in the net productivity trace, respectively.

Average chromosome counts from bulk culture (related to FIG. 9).

| Strain | Growth Phase | Average Chromosome Number | Standard Deviation |
|---|---|---|---|
| scJC0147 | Exponential | 3.8 | +/−0.4 |
| scJC0147 | Stationary | 1.8 | +/−0.3 |
| PCC 7002 | Exponential | 3.3 | +/−0.6 |
| PCC 7002 | Stationary | 2.3 | +/−0.1 |

Average chromosome counts from bulk culture mOrange2::240x tetO array::TetR-sfGFP (scJC0147) or WT PCC 7002 cells grown to exponential or stationary phase. mOrange2::240x tetO array::TetR-sfGFP cultures were resupplied with 0.5 μg/mL every 48 hr.

TABLE 5

| Oligo Name | Description | Sequence 5'-3' | Used For |
|---|---|---|---|
| JCC388 | F glpK upstream | CAATGGCGAAGGTTTTCTGT [SEQ ID NO: 15] | glpK insertion and segregation |
| JCC389 | R glpK downstream | GGGAGATGCTGTAGGCAAGA [SEQ ID NO: 16] | glpK insertion and segregation |
| KAMo0252 | F NSI upstream | CAAGTGGGCAGCAACTGTAG [SEQ ID NO: 17] | NSI insertion and segregation |
| KAMo0061 | R NSI downstream | CTGCATGTCAACAACCACAA [SEQ ID NO: 18] | NSI insertion and segregation |

TABLE 5-continued

| Oligo Name | Description | Sequence 5'-3' | Used For |
|---|---|---|---|
| EBJp0180 | F acsA internal | GTAATCATCACACCACC [SEQ ID NO: 19] | acsA segregation |
| EBJp0181 | R acsA internal | TCATCCTCTATACCAGC [SEQ ID NO: 20] | acsA segregation |
| EBJp0087 | R GmR | CGGCAGAATGCTTAATG [SEQ ID NO: 21] | GmR insertion |
| EBJp0083 | R KmR | CTAGAGCAAGACGTTTC [SEQ ID NO: 22] | KmR insertion |
| EBJp0178 | F glpK internal | CTTGGGCAAGATCATTC [SEQ ID NO: 23] | glpK segregation |
| EBJp0179 | R glpK internal | GATCACAGTAATGCCAG [SEQ ID NO: 24] | glpK segregation |
| EBJp0060 | F parA upstream | TCGAGCTCGGTACCCGGGTGCGTCGAGGGTG CCTTG [SEQ ID NO: 25] | ΔparA insertion and segregation |
| EBJp0103 | R parA internal | GGCGAGATTGACTACTG [SEQ ID NO: 26] | ΔparA segregation |
| KAMo0575 | F dnaA upstream | ACGGCCAGTGAATTCGAGCTAGCAGGACTTC ATTGCATCG [SEQ ID NO: 27] | ΔdnaA insertion and segregation |
| KAMo0579 | R dnaA internal | AAGTGAGGCGTACCTTAACG [SEQ ID NO: 28] | ΔdnaA segregation |
| KAMo0398 | F PCC7002 1000 bp | TTGTTCTCGCGAGCGATCG [SEQ ID NO: 29] | qPCR standard curve |
| KAMo0499 | R PCC7002 1000 bp | GCACAAACATCGCACTGATC [SEQ ID NO: 30] | qPCR standard curve |
| KAMo0143 | F PCC7002 200 bp | GATCTCTGGCCTACCGATGA [SEQ ID NO: 31] | qPCR |
| KAMo0145 | R PCC7002 200 bp | TGTTGGCGCATCAAATACAT [SEQ ID NO: 32] | qPCR |

Strain Segmentation and qPCR Oligonucleotides. PCC 7002 gene names are italicized. NSI is a neutral site described by Davies, Work, Beliaev, & Posewitz, 2014)

TABLE 6

| Gene Name | Protein ID | sgRNA sequence 5'-3' |
|---|---|---|
| ftsZ | ACA98042.1 | UGCGACUUCGGCGACGAUGG [SEQ ID NO: 33] |
| dnaX | ACA99693.1 | ACCAACUGCGCAAAAGUCUG [SEQ ID NO: 34] |
| minD | ACA98521.1 | GCCGACGCCUCCUUUUCCGG [SEQ ID NO: 35] |
| murE | ACA98136.1 | UUGACAACUUGCUGUAGCAU [SEQ ID NO: 36] |
| mreB | ACA99516.1 | CUACAACAGACGGUUCCUGG [SEQ ID NO: 37] |

Gene name, protein ID, and sgRNA sequences.

TABLE 7

| Plasmid Name | Description | Neutral Site |
|---|---|---|
| KAMc0006 | 120x tetO-array flanking GmR Cassette | glpK |
| KAMc0064 | pJ23113:tetR-sfGFP:SpR cassette | acsA |
| KAMc0084 | pJ23113:tetR-sfGFP:dCas9:SpR cassette | acsA |
| KAMc0131 | pCpt:mOrange2:KmR cassette | NSI |
| KAMc0189 | pJ23119:mOrange2:KmR cassette | NSI |
| KAMc0197 | dnaA upstream and downstream regions flanking KmR cassette | N/A |
| KAMc0205 | cLac94:ftsZ-sgRNA3:LacI:KmR cassette | NSI |
| KAMc0208 | cLac94:dnaX-sgRNA:LacI:KmR cassette | NSI |
| KAMc0211 | cLac94:minD-sgRNA:LacI:KmR cassette | NSI |
| KAMc0217 | cLac94:murE-sgRNA:LacI:KmR cassette | NSI |
| KAMc0223 | cLac94:mreB-sgRNA2:LacI:KmR cassette | NSI |
| EBJc0022 | parA upstream and downstream regions flanking KmR cassette | N/A |

Plasmids used in this study. GmR=gentamycin resistance. KmR=kanamycin resistance, SpR=spectinomycin resistance. NSI is a neutral site described by Davies et al., 2014. PCC7002 gene names are italicized.

TABLE 8

| Strain Name | Description | Transformed Plasmids | Ab Resistance |
|---|---|---|---|
| Wild Type (WT) | Synechococcus PCC 7002 | None | None |
| scJC0134 | ΔglpK:240x tetO array:GmR:: ΔacsA:tetR-sfGFP:SpR | KAMc0006, KAMc0064 | Gm, Sp |
| scJC0147 | ΔglpK:240x tetO array:GmR:: ΔacsA:tetR-sfGFP:SpR::ΔNS1:pCpt-mOrange2:KmR | KAMc0006, KAMc0064, KAMc0131 | Gm, Sp, Km |
| scJC0164 | ΔglpK:240x tetO array:GmR:: ΔacsA:tetR-sfGFP:dCas9:SpR | KAMc0006, KAMc0084 | Gm, Sp |
| scJC0182 | ΔglpK:240x tetO array:GmR:: ΔacsA:tetR-sfGFP:SpR::ΔNS1: pJ23119-mOrange2:KmR | KAMc0006, KAMc0064, KAMc0189 | Gm, Sp, Km |

TABLE 8-continued

| Strain Name | Description | Transformed Plasmids | Ab Resistance |
|---|---|---|---|
| scJC0189 | ΔglpK:240x tetO array:GmR::ΔacsA:tetR-sfGFP:SpR::ΔdnaA:KmR | KAMc0006, KAMc0064, KAMc0197 | Gm, Sp, Km |
| KAMs0003 | ΔglpK:240x tetO array:GmR::ΔacsA:tetR-sfGFP:SpR::ΔparA:KmR | KAMc0006, KAMc0064, EBJc0022 | Gm, Sp, Km |

PCC7002 derived strains. Plasmid descriptions can be found in Table S4. GmR—gentamycin resistance, Gm—gentamycin, KmR—kanamycin resistance, Km—kanamycin, SpR—spectinomycin resistance, Sp—spectinomycin. Genotypes are italicized.

What is claimed is:

1. A method of controlling growth, expression, or carboxysome number in a bacterial strain comprising the steps of:

provided a bacterial strain having a ccm operon under the control of an inducible promoter;

contacting the bacterial strain with an agent that induces the promoter, whereby inducing the promoter increases growth, expression, or carboxysome number;

removing the agent from the bacterial strain; and maintaining the bacterial strain in ambient $CO_2$ or other $CO_2$ concentration wherein carboxysome expression is inhibited, whereby continued growth and division of the bacterial strain results in a decrease in the number of carboxysomes in progeny cells.

2. The method of controlling growth, expression, or carboxysome number in a bacterial strain according to claim 1 wherein all or a portion of the native ccm operon has been deleted.

3. The method of controlling growth, expression, or carboxysome number in a bacterial strain according to claim 1 further comprising the step of maintaining the bacterial strain in ambient $CO_2$ or other $CO_2$ concentration wherein carboxysome expression is inhibited, prior to the step of contacting the bacterial strain with the agent that induces the promoter.

4. A method of controlling carboxysome number, growth, or expression in a bacterial strain comprising the steps of:
providing a bacterial strain having a labeled carbon-fixation enzyme and genetically-engineered to have all or a portion of a ccm operon of the bacterial strain under the control of an inducible promoter;
maintaining a population of the bacterial strain in ambient $CO_2$ or other concentration of $CO_2$ wherein production of carboxysomes in the population is inhibited and expression from the ccm operon in the bacterial strain is not induced;
contacting the population of the bacterial strain with an agent that induces the inducible promoter of the ccm operon, wherein inducing the promoter increases expression from the ccm operon whereby increasing expression from the ccm operon increases carboxysome numbers in the population;
removing the agent from the population of the bacterial strain;
maintaining the population of the bacterial strain in ambient $CO_2$ or other $CO_2$ concentration wherein expression from the ccm operon is inhibited, whereby continued growth and division of the population of bacterial strain results in a decrease on the number of carboxysomes in progeny cells in the population;
detecting puncta in the population of cells resulting from labeled enzymes within in the carboxysomes of the bacterial strain, whereby punctum correspond to single carboxysomes;
identifying a bacterial cell within the population containing only one punctum per cell; and
following the identified bacterial cell through a plurality of timepoints.

5. The method of controlling carboxysome number, growth, or expression in a bacterial strain according to claim 4 further comprising the step of measuring the growth of the cell at two or more timepoints, wherein the growth is an indicator of carboxysome activity.

6. The method of controlling carboxysome number, growth, or expression in a bacterial strain according to claim 4 wherein all or a portion of the native ccm operon has been deleted.

7. The method of controlling carboxysome number, growth, or expression in a bacterial strain according to claim 4 further comprising the step of measuring one or more parameters of the identified bacterial cells at a plurality of timepoints.

8. The method of controlling carboxysome number, growth, or expression in a bacterial strain according to claim 7 wherein one of the measured parameters is cell length.

9. The method of controlling carboxysome number, growth, or expression in a bacterial strain according to claim 8 further comprising the step of contacting the cell with one or more agents and comparing the measured parameter to the parameter in an uncontacted control.

10. The method of controlling carboxysome number, growth, or expression in a bacterial strain according to claim 4 wherein puncta are detected by visualization.

11. The method of controlling carboxysome number, growth, or expression in a bacterial strain according to claim 10 wherein visualization is facilitated by fluorescence of the label.

12. The method of controlling carboxysome number, growth, or expression in a bacterial strain according to claim 4 wherein following the identified bacterial cell is performed by time-lapse fluorescence microscopy to facilitate tracking of fluorescently-labeled carboxysomes.

13. The method of controlling carboxysome number, growth, or expression in a bacterial strain according to claim 4 wherein the carbon-fixation enzyme is 1, 5-bisphosphate carboxylase/oxygenase (RuBisCO).

14. A method of controlling bacterial growth, expression, or microcompartment number in a bacterial strain comprising the steps of:
providing a population of the bacterial strain genetically-engineered to have all or a portion of a ccm operon of the bacterial strain under the control of an inducible promoter;
contacting the population of the bacterial strain with an agent that induces the inducible promoter of the ccm operon, wherein inducing the promoter increases expression from the ccm operon whereby increasing expression from the ccm operon increases carboxysome numbers in the population;
removing the agent from the population of the bacterial strain;
maintaining the population of the bacterial strain in ambient $CO_2$ or other $CO_2$ concentration wherein expression from the ccm operon is inhibited, whereby continued growth and division of the population of bacterial strain results in a decrease on the number of carboxysomes in progeny cells in the population; and
following the identified bacterial cell through a plurality of timepoints.

* * * * *

```
                        SEQUENCE LISTING

<160> NUMBER OF SEQ ID NOS: 37

<210> SEQ ID NO 1
<211> LENGTH: 20
<212> TYPE: DNA
<213> ORGANISM: Artificial Sequence
<220> FEATURE:
<223> OTHER INFORMATION: Primer sequence

<400> SEQUENCE: 1
agcctggccc gtgaaggtaa                                              20

<210> SEQ ID NO 2
<211> LENGTH: 33
<212> TYPE: DNA
<213> ORGANISM: Artificial Sequence
<220> FEATURE:
<223> OTHER INFORMATION: Primer sequence

<400> SEQUENCE: 2 gtcttttta aattcaatgg gtttacgtta gag                                33

<210> SEQ ID NO 3
<211> LENGTH: 20
<212> TYPE: DNA
<213> ORGANISM: Artificial Sequence
<220> FEATURE:
<223> OTHER INFORMATION: Primer sequence

<400> SEQUENCE: 3
taaccaagat tccggtacgc                                              20

<210> SEQ ID NO 4
<211> LENGTH: 17
<212> TYPE: DNA
<213> ORGANISM: Artificial Sequence
<220> FEATURE:
<223> OTHER INFORMATION: Primer sequence

<400> SEQUENCE: 4
gatgctgtag gcaagag                                                 17

<210> SEQ ID NO 5
<211> LENGTH: 20
<212> TYPE: DNA
<213> ORGANISM: Artificial Sequence
<220> FEATURE:
<223> OTHER INFORMATION: Primer sequence

<400> SEQUENCE: 5
```

```
cgactgaatc cggtgagaat                                              20

<210> SEQ ID NO 6
<211> LENGTH: 32
<212> TYPE: DNA
<213> ORGANISM: Artificial Sequence
<220> FEATURE:
<223> OTHER INFORMATION: Primer sequence

<400> SEQUENCE: 6
ataggttctg aattgttcta cttcttcggt gt                                32

<210> SEQ ID NO 7
<211> LENGTH: 19
<212> TYPE: DNA
<213> ORGANISM: Artificial Sequence
<220> FEATURE:
<223> OTHER INFORMATION: Primer sequence

<400> SEQUENCE: 7
cggtggagac gatgatccg                                               19

<210> SEQ ID NO 8
<211> LENGTH: 27
<212> TYPE: DNA
<213> ORGANISM: Artificial Sequence
<220> FEATURE:
<223> OTHER INFORMATION: Primer sequence

<400> SEQUENCE: 8
gtttctggaa atcacagagg atgcgtg                                      27

<210> SEQ ID NO 9
<211> LENGTH: 17
<212> TYPE: DNA
<213> ORGANISM: Artificial Sequence
<220> FEATURE:
<223> OTHER INFORMATION: Primer sequence

<400> SEQUENCE: 9
tcatcctcta taccagc                                                 17

<210> SEQ ID NO 10
<211> LENGTH: 17
<212> TYPE: DNA
<213> ORGANISM: Artificial Sequence
<220> FEATURE:
<223> OTHER INFORMATION: Primer sequence

<400> SEQUENCE: 10
atgaatcggg tcaacag                                                 17

<210> SEQ ID NO 11
<211> LENGTH: 27
<212> TYPE: DNA
<213> ORGANISM: Artificial Sequence
<220> FEATURE:
<223> OTHER INFORMATION: Primer sequence

<400> SEQUENCE: 11
tgagccttag cgagggcggt gctttgg                                      27

<210> SEQ ID NO 12
<211> LENGTH: 39
<212> TYPE: DNA
```

```
<213> ORGANISM: Artificial Sequence
<220> FEATURE:
<223> OTHER INFORMATION: Primer sequence

<400> SEQUENCE: 12
ctcgcttatc acttgactttt atgagttggt gtgtgaaat                              39

<210> SEQ ID NO 13
<211> LENGTH: 43
<212> TYPE: DNA
<213> ORGANISM: Artificial Sequence
<220> FEATURE:
<223> OTHER INFORMATION: Primer sequence

<400> SEQUENCE: 13
aaagtcaagt gataagcgag gataaattag atgcctattg cag                         43

<210> SEQ ID NO 14
<211> LENGTH: 34
<212> TYPE: DNA
<213> ORGANISM: Artificial Sequence
<220> FEATURE:
<223> OTHER INFORMATION: Primer sequence

<400> SEQUENCE: 14
accgccctcg ctaaggctca tctggttgat ttgg                                    34

<210> SEQ ID NO 15
<211> LENGTH: 20
<212> TYPE: DNA
<213> ORGANISM: Artificial Sequence
<220> FEATURE:
<223> OTHER INFORMATION: Primer sequence

<400> SEQUENCE: 15
caatggcgaa ggttttctgt                                                   20

<210> SEQ ID NO 16
<211> LENGTH: 20
<212> TYPE: DNA
<213> ORGANISM: Artificial Sequence
<220> FEATURE:
<223> OTHER INFORMATION: glpK insertion and segregation

<400> SEQUENCE: 16
gggagatgct gtaggcaaga                                                   20

<210> SEQ ID NO 17
<211> LENGTH: 20
<212> TYPE: DNA
<213> ORGANISM: Artificial Sequence
<220> FEATURE:
<223> OTHER INFORMATION: NSI insertion and segregation

<400> SEQUENCE: 17
caagtgggca gcaactgtag                                                   20

<210> SEQ ID NO 18
<211> LENGTH: 20
<212> TYPE: DNA
<213> ORGANISM: Artificial Sequence
<220> FEATURE:
<223> OTHER INFORMATION: NSI insertion and segregation

<400> SEQUENCE: 18
ctgcatgtca acaaccacaa                                                   20
```

<210> SEQ ID NO 19
<211> LENGTH: 17
<212> TYPE: DNA
<213> ORGANISM: Artificial Sequence
<220> FEATURE:
<223> OTHER INFORMATION: acsA segregation

<400> SEQUENCE: 19
gtaatcatca caccacc                                                17

<210> SEQ ID NO 20
<211> LENGTH: 17
<212> TYPE: DNA
<213> ORGANISM: Artificial Sequence
<220> FEATURE:
<223> OTHER INFORMATION: acsA segregation

<400> SEQUENCE: 20
tcatcctcta taccagc                                                17

<210> SEQ ID NO 21
<211> LENGTH: 17
<212> TYPE: DNA
<213> ORGANISM: Artificial Sequence
<220> FEATURE:
<223> OTHER INFORMATION: GmR insertion

<400> SEQUENCE: 21
cggcagaatg cttaatg                                                17

<210> SEQ ID NO 22
<211> LENGTH: 17
<212> TYPE: DNA
<213> ORGANISM: Artificial Sequence
<220> FEATURE:
<223> OTHER INFORMATION: KmR insertion

<400> SEQUENCE: 22
ctagagcaag acgtttc                                                17

<210> SEQ ID NO 23
<211> LENGTH: 17
<212> TYPE: DNA
<213> ORGANISM: Artificial Sequence
<220> FEATURE:
<223> OTHER INFORMATION: glpK segregation

<400> SEQUENCE: 23
cttgggcaag atcattc                                                17

<210> SEQ ID NO 24
<211> LENGTH: 17
<212> TYPE: DNA
<213> ORGANISM: Artificial Sequence
<220> FEATURE:
<223> OTHER INFORMATION: glpK segregation

<400> SEQUENCE: 24
gatcacagta atgccag                                                17

<210> SEQ ID NO 25
<211> LENGTH: 36
<212> TYPE: DNA
<213> ORGANISM: Artificial Sequence
<220> FEATURE:

```
<223> OTHER INFORMATION: glpK segregation

<400> SEQUENCE: 25
tcgagctcgg tacccgggtg cgtcgagggt gccttg                              36

<210> SEQ ID NO 26
<211> LENGTH: 17
<212> TYPE: DNA
<213> ORGANISM: Artificial Sequence
<220> FEATURE:
<223> OTHER INFORMATION: parA insertion and segregation

<400> SEQUENCE: 26
ggcgagattg actactg                                                   17

<210> SEQ ID NO 27
<211> LENGTH: 40
<212> TYPE: DNA
<213> ORGANISM: Artificial Sequence
<220> FEATURE:
<223> OTHER INFORMATION: dnaA insertion and segregation

<400> SEQUENCE: 27
acggccagtg aattcgagct agcaggactt cattgcatcg                          40

<210> SEQ ID NO 28
<211> LENGTH: 20
<212> TYPE: DNA
<213> ORGANISM: Artificial Sequence
<220> FEATURE:
<223> OTHER INFORMATION: dnaA segregation

<400> SEQUENCE: 28
aagtgaggcg taccttaacg                                                20

<210> SEQ ID NO 29
<211> LENGTH: 19
<212> TYPE: DNA
<213> ORGANISM: Artificial Sequence
<220> FEATURE:
<223> OTHER INFORMATION: qPCR standard curve

<400> SEQUENCE: 29
ttgttctcgc gagcgatcg                                                 19

<210> SEQ ID NO 30
<211> LENGTH: 19
<212> TYPE: DNA
<213> ORGANISM: Artificial Sequence
<220> FEATURE:
<223> OTHER INFORMATION: qPCR standard curve

<400> SEQUENCE: 30
ttgttctcgc gagcgatcg                                                 19

<210> SEQ ID NO 31
<211> LENGTH: 20
<212> TYPE: DNA
<213> ORGANISM: Artificial Sequence
<220> FEATURE:
<223> OTHER INFORMATION: qPCR

<400> SEQUENCE: 31
gatctctggc ctaccgatga                                                20
```

```
<210> SEQ ID NO 32
<211> LENGTH: 20
<212> TYPE: DNA
<213> ORGANISM: Artificial Sequence
<220> FEATURE:
<223> OTHER INFORMATION: qPCR

<400> SEQUENCE: 32
tgttggcgca tcaaatacat                                               20

<210> SEQ ID NO 33
<211> LENGTH: 20
<212> TYPE: RNA
<213> ORGANISM: Artificial Sequence
<220> FEATURE:
<223> OTHER INFORMATION: sgRNA sequence

<400> SEQUENCE: 33
ugcgacuucg gcgacgaugg                                               20

<210> SEQ ID NO 34
<211> LENGTH: 20
<212> TYPE: RNA
<213> ORGANISM: Artificial Sequence
<220> FEATURE:
<223> OTHER INFORMATION: sgRNA sequence

<400> SEQUENCE: 34
accaacugcg caaaagucug                                               20

<210> SEQ ID NO 35
<211> LENGTH: 20
<212> TYPE: RNA
<213> ORGANISM: Artificial Sequence
<220> FEATURE:
<223> OTHER INFORMATION: sgRNA sequence

<400> SEQUENCE: 35
gccgacgccu ccuuuuccgg                                               20

<210> SEQ ID NO 36
<211> LENGTH: 20
<212> TYPE: RNA
<213> ORGANISM: Artificial Sequence
<220> FEATURE:
<223> OTHER INFORMATION: sgRNA sequence

<400> SEQUENCE: 36
uugacaacuu gcuguagcau                                               20

<210> SEQ ID NO 37
<211> LENGTH: 20
<212> TYPE: RNA
<213> ORGANISM: Artificial Sequence
<220> FEATURE:
<223> OTHER INFORMATION: sgRNA sequence

<400> SEQUENCE: 37
cuacaacaga cgguuccugg                                               20
```